United States Patent
Renner et al.

(10) Patent No.: US 7,229,624 B2
(45) Date of Patent: *Jun. 12, 2007

(54) ORDERED MOLECULAR PRESENTATION OF ANTIGENS, METHOD OF PREPARATION AND USE

(75) Inventors: Wolfgang A. Renner, Zürich (CH); Frank Hennecke, Zürich (CH); Lars Nieba, Winterthur (CH); Martin Bachmann, Winterthur (CH)

(73) Assignee: Cytos Biotechnology AG, Zürich-Schlieren (CH)

( * ) Notice: Subject to any disclaimer, the term of this patent is extended or adjusted under 35 U.S.C. 154(b) by 556 days.

This patent is subject to a terminal disclaimer.

(21) Appl. No.: 10/733,582

(22) Filed: Dec. 12, 2003

(65) Prior Publication Data

US 2004/0136962 A1 Jul. 15, 2004

Related U.S. Application Data

(63) Continuation of application No. 09/449,631, filed on Nov. 30, 1999, now abandoned.

(60) Provisional application No. 60/110,414, filed on Nov. 30, 1998, provisional application No. 60/142,788, filed on Jul. 8, 1999.

(51) Int. Cl.
*A61K 39/385* (2006.01)

(52) U.S. Cl. .............................. 424/196.11; 435/235.1; 424/184.1; 424/185.1; 424/204.1; 424/205.1

(58) Field of Classification Search ............... 424/400, 424/196.11, 199.1, 275.1; 435/235.1; 530/403
See application file for complete search history.

(56) References Cited

U.S. PATENT DOCUMENTS

| | | | |
|---|---|---|---|
| 4,722,840 A | 2/1988 | Valenzuela et al. ............ 424/88 |
| 5,071,651 A | 12/1991 | Sabara et al. .................. 424/89 |
| 5,143,726 A | 9/1992 | Thornton et al. ............. 424/88 |
| 5,334,394 A | 8/1994 | Kossovsky et al. ......... 424/494 |
| 5,374,426 A | 12/1994 | Sabara et al. ............... 530/403 |
| 5,698,424 A * | 12/1997 | Mastico et al. .............. 435/477 |
| 5,739,026 A | 4/1998 | Garoff et al. ............ 435/240.2 |
| 5,766,602 A | 6/1998 | Xiong et al. ............. 424/218.1 |
| 5,770,380 A | 6/1998 | Hamilton et al. ............ 435/7.1 |
| 5,789,245 A | 8/1998 | Dubensky, Jr. et al. .. 435/320.1 |
| 5,792,462 A | 8/1998 | Johnston et al. ......... 424/199.1 |
| 5,814,482 A | 9/1998 | Dubensky, Jr. et al. .... 435/69.3 |
| 5,871,747 A | 2/1999 | Gengoux-Sedlik et al. ........................ 424/208.1 |
| 5,916,818 A * | 6/1999 | Irsch et al. .................. 436/548 |
| 6,004,763 A | 12/1999 | Gengoux et al. ........... 435/7.24 |
| 6,180,771 B1 * | 1/2001 | Thomas et al. ............. 536/23.5 |
| 6,827,937 B2 * | 12/2004 | Murray ..................... 424/193.1 |
| 6,964,769 B2 * | 11/2005 | Sebbel et al. ............ 424/189.1 |

FOREIGN PATENT DOCUMENTS

| | | | |
|---|---|---|---|
| EP | 0 259 149 A2 | 3/1988 |
| EP | 0 385 610 A1 | 9/1990 |
| EP | 0 425 082 A1 | 5/1991 |
| EP | 0 465 081 B1 | 1/1992 |
| JP | 09202735 A * | 8/1997 |
| WO | WO 92/11291 A1 | 7/1992 |
| WO | WO 94/06472 A1 | 3/1994 |
| WO | WO 94/15585 A1 | 7/1994 |
| WO | WO 96/05293 A1 | 2/1996 |
| WO | WO 96/30523 A2 | 10/1996 |
| WO | WO 97/31948 A1 | 9/1997 |
| WO | WO 98/15631 A1 | 4/1998 |
| WO | WO 9828624 * | 7/1998 |
| WO | WO 99/07839 A2 | 2/1999 |
| WO | WO 99/40934 A1 | 8/1999 |
| WO | WO 99/67293 A1 | 12/1999 |

OTHER PUBLICATIONS

Ormstad et al. Clinical and Experimental Allergy 28:702-708, 1998.*
Harris et al. international Immunology 9:273-280, 1997.*
Miescher et al (Molecular Aspects of Medicing 23:413-462, 2002).*
Baba, T. W., et al., "Pathogenicity of Live, Attenuated SIV After Mucosal Infection of Neonatal Macaques," *Science* 267:1820-1825 (1995), American Association for the Advancement of Science.

(Continued)

*Primary Examiner*—Shanon Foley
*Assistant Examiner*—Stuart W. Snyder
(74) *Attorney, Agent, or Firm*—Sterne, Kessler, Goldstein & Fox P.L.L.C.

(57) ABSTRACT

The invention provides compositions and processes for the production of ordered and repetitive antigen or antigenic determinant arrays. The compositions of the invention are useful for the production of vaccines for the prevention of infectious diseases, the treatment of allergies and the treatment of cancers. Various embodiments of the invention provide for a virus, virus-like particle, viral capsid particle, phage or recombinant form thereof coated with any desired antigen in a highly ordered and repetitive fashion as the result of specific interactions. In one specific embodiment, a versatile new technology based on a cassette-type system (AlphaVaccine Technology) allows production of antigen coated viral particles. Other specific embodiments allow the production of antigen coated hepatitis B virus-like particles or antigen coated Measles virus-like particles.

43 Claims, 7 Drawing Sheets

OTHER PUBLICATIONS

Bachmann, M. F., et al., "Dendritic cells process exogenous viral proteins and virus-like particles for class I presentation to CD8+ cytotoxic T lymphocytes," *Eur. J. Immunol.* 26:2595-2600 (1996), VCH Verlagsgesellschaft mbH.

Bachmann, M. F. and Zinkemagel, R. M., "The influence of virus structure on antibody responses and virus serotype formation," *Immunol. Today* 17: 553-558 (1996). Elsevier Science Ltd.

Bachmann, M. F. and Zinkernagel, R. M., "Neutralizing Antiviral B Cell Responses," *Annu. Rev. Immunol.* 15:235-270 (Apr. 1997), Annual Reviews Inc.

Borisova, G., et al., "Hybrid Hepatitis B Virus Nucleocapsid Bearing an Immunodominant Region from Hepatitis B Virus Surface Antigen," *J. Virol.* 67:3696-3701 (1993), American Society for Microbiology.

Cesareni, G., "Peptide display on filamentous phage capsids," *FEBS Lett.* 307:66-70 (1992), Elsevier Science Publishers B.V.

Clark, H. F., et al., "Comparative Characterization of a C-Type Virus-Producing Cell Line (VSW) and a Virus-Free Cell Line (VH2) from *Vipera russelli*," *J. Natl. Cancer Inst.* 51:645-657 (1973), Oxford University Press.

Connor, R. I., et al., "Immunological and Virological Analyses of Persons Infected by Human Immunodeficiency Virus Type 1 while Participating in Trials of Recombinant gp120 Subunit Vaccines," *J. Virol.* 72:1552-1576 (Feb. 1998), American Society for Microbiology.

Crameri, R. and Suter, M., "Display of biologically active proteins on the surface of filamentous phages: a cDNA cloning system for selection of functional gene products linked to the genetic information responsible for their production," *Gene* 137:69-75 (1993), Elsevier Science Publishers B.V.

Daniel, M. D., et al., "Protective Effects of a Live Attenuated SIV Vaccine with a Deletion in the *nef*Gene," *Science* 258:1938-1941 (1992), American Association for the Advancement of Science.

Davis, N. L., et al., "*In Vitro* Synthesis of Infectious Venezuelan Equine Encephalitis Virus RNA from a cDNA Clone: Analysis of a Viable Deletion Mutant," *Virology* 171:189-204 (1989), Academic Press Inc.

de la Cruz, V. F., et al., "Immunogenicity and Epitope Mapping of Foreign Sequences via Genetically Engineered Filamentous Phage," *J. Biol. Chem.* 263:4318-4322 (1988). The American Society for Biochemistry and Molecular Biology Inc.

Donnelly, J. J., et al., "DNA Vaccines," *Annu. Rev. Immunol.* 15:617-648 (Apr. 1997), Annual Reviews Inc.

Fehr, T., et al., "Role of Repetitive Antigen Patterns for Induction of Antibodies Against Antibodies," *J. Exp. Med.* 185:1785-1792 (May 1997), The Rockefeller University Press.

Förster, E., et al., "Natural and recombinant enzymatically active or inactive bee venom phospholipase $A_2$ has the same potency to release histamine from basophils in patients with Hymenoptera allergy," *J. Allergy Clin. Immunol.* 95:1229-1235 (1995), Mosby-Year Book, Inc.

Fujiwara, K., et al., "Novel Preparation Method of Immunogen for Hydrophobic Hapten, Enzyme Immunoassay for Daunomycin and Adriamycin," *J. Immunol. Meth.* 45:195-203 (1981), Elsevier/North Holland Biomedical Press.

Gilbert, S. C., et al., "A protein particle vaccine containing multiple malaria epitomes," *Nature Biotechnol.* 15:1280-1284 (Nov. 1997), Nature Publishing Group.

Greenstone, H. L., et al., "Chimeric papillomavirus virus-like particles elicit antitumor immunity against the E7 oncoprotein in an HPV16 tumor model," *Proc. Natl. Acad. Sci. USA* 95:1800-1805 (Feb. 1998), The National Academy of Sciences.

Hahn, C. S., et al., "Infectious Sindbis virus transient expression vectors for studying antigen processing and presentation," *Proc. Natl. Acad. Sci. USA* 89:2679-2683 (1992), National Academy Press.

Harding, C. V. and Song, R., "Phagocytic Processing of Exogenous Particulate Antigens by Macrophages for Presentation by Class I MHC Molecules," *J. Immunol.* 153:4925-4933 (1994), The American Association of Immunologists.

Hilleman, M. R., "Six decades of vaccine development—a personal history," *Nature Med. Vaccine Suppl.* 4:507-514 (May 1998), Nature Publishing Group.

Iannolo, G., et al., "Construction, Exploitation and Evolution of a New Peptide Library Displayed at High Density by Fusion to the Major Coat Protein of Filamentous Phage," *Biol. Chem.* 378:517-521 (Jun. 1997), Walter de Gruyter & Company.

Iannolo, G., et al., "Modifying Filamentous Phage Capsid: Limits in the Size of the Major Capsid Protein," *J. Mol. Biol.* 248:835-844 (1995), Academic Press Limited.

Jiang, X., et al., "Norwalk Virus Genome Cloning and Characterization," *Science* 250:1580-1583 (1990), American Association for the Advancement of Science.

Kovacsovics-Bankowski, M., et al., "Efficient major histocampatibility complex class I presentation of exogenous antigen upon phagocytosis by macrophage," *Proc. Natl. Acad. Sci. USA* 90: 4942-4946 (1993), National Academy Press.

Kratz, P. A., et al., "Native display of complete foreign protein domains on the surface of hepatitis B virus capsids," *Proc. Natl. Acad. Sci. USA* 96:1915-1920 (Mar. 1999). National Academy Press.

Landschulz, W. H., et al., "The Leucine Zipper: A Hypothetical Structure Common to a New Class of DNA Binding Proteins," *Science* 240:1759-1764 (1988), American Association for the Advancement of Science.

Leake, C. J., et al., "Cytopathic Effect and Plaque Formation by Arboviruses in a Continuous Cell Line (XTC-2) from the Toad *Xenopus laevis*," *J. Gen. Virol.* 35:335-339 (1977), Society for General Microbiology.

Lee, K. H., et al., "Two-Dimensional Electrophoresis of Proteins as a Tool in the Metabolic Engineering of Cell Cycle Regulation," *Biotech. and Bioeng.* 50:336-340 (1996), John Wiley & Sons, Inc.

Liljeström, P. and Garoff, H., "A New Generation of Animal Cell Expression Vectors Based on the Semliki Forest Virus Replicon," *Bio/technology* 9:1356-1361 (1991), Nature Publishing Group.

Liljeström, P., "Alphavirus expression systems," *Curr. Opin. Biotech.* 5:495-500 (1994), Current Biology Ltd.

Lo-Man, R., et al., "A recombinant virus-like particle system derived from parvovirus as an efficient antigen carrier to elicit a polarized Th1 immune response without adjuvant," *Eur. J. Immunol.* 28:1401-1407 (Apr. 1998), Wiley-VCH Verlag GmbH.

López, O., et al., "Direct formation of mixed micelles in the solubilization of phospholipid liposomes by Triton X-100," *FEBS Lett.* 426:314-318 (Apr. 1998), Elsevier Science B.V. for Federation of European Biochemical Societies.

Lundstrom, K., "Alphaviruses as expression vectors," *Curr. Opin. Biotech.* 8:578-582 (Oct. 1997), Current Biology Ltd.

Matsui, S. M., et al., "The Isolation and Characterization of a Norwalk Virus-specific cDNA," *J. Clin. Invest.* 87:1456-1461 (1991), American Society for Clinical Investigation Inc.

Minenkova, O. O., et al., "Design of specific immunogens using filamentous phage as the carrier," *Gene* 128:85-88 (1993), Elsevier Science Publishers B.V.

Morein, B., et al., "Iscom, a novel structure for antigenic presentation of membrane proteins from enveloped viruses," *Nature* 308:457-460 (1984), Nature Publishing Group.

Neurath, A. R., et al., "Hepatitis B Virus Surface Antigen (HBsAg) As Carrier for Synthetic Peptides Having An Attached Hydrophobic Tail," *Mol. Immunol.* 26:53-62 (1989), Pergamon Press.

O'Shea, E. K., et al., "Mechanism of Specificity in the Fos-Jun Oncoprotein Heterodimer," *Cell* 68:699-708 (1992), Cell Press.

Perham, R. N., et al., "Engineering a peptide epitope display system on filamentous bacteriophage," *FEMS Microbiol. Rev.* 17:25-31 (1995), Elsevier Science Publishers on behalf of the Federation of European Microbiological Societies.

Petrenko, V. A., et al, "A library of organic landscapes on filamentous phage," *Protein Eng.* 9:797-801 (1996), Oxford University Press.

Pumpens, P. and Grens, E., "Hepatitis B core particles as a universal display model: a structure-function basis for development," *FEBS Lett.* 442:1-6 (Jan. 1999), Elsevier Science B.V., for Federation of European Biochemical Societies.

Raychaudhuri, S. and Rock, K. L., "Fully mobilizing host defense: Building better vaccines," *Nature Biotechnol. 16*:1025-1031 (Nov. 1998), Nature America Inc.

Redfield, R. R., et al., "Dissminated Vaccinia in a Military Recruit with Human Immunodeficiency Virus (HIV) Disease," *N. Eng. J. Med. 316*:673-676 (1987), Massachusetts Medical Society.

Renner, W. A., et al., "Recombinant Cyclin E Expression Activates Proliferation and Obviates Surface Attachment of Chinese Hamster Ovary (CHO) Cells in Protein-Free Medium," *Biotech. Bioeng. 47*:476-482 (1995), John Wiley & Sons Inc.

Romagnani, S., "The Th1/Th2 paradigm," *Immunol. Today 18*:263-266 (Jun. 1997), Elsevier-Science Ltd.

Schlesinger, S., Alphaviruses—vectors for the expression of heterologous genes, *TIBTECH 11*:18-22 (1993), Elsevier Science Publishers Ltd. (UK).

Sedlik, C., et al., "Recombinant parvovirus-like particles as an antigen carrier: A novel nonreplicative exogenous antigen to elicit protective antiviral cyctotoxic T cells," *Proc. Natl. Acad. Sci. USA 94*:7503-7508 (Jul. 1997), National Academy of Sciences.

Shen, L., et al., "Recombinant Virus Vaccine-Induced SIV-Specific CD8+ Cytotoxic T Lymphocytes," *Science 252*:440-443 (1991), American Association for the Advancement of Science.

Stollar, V., "Togaviruses In Cultured Arthropod Cells," in *The Togaviruses: Biology, Structure, Replication*, Schlesinger, R. W. (ed.), Academic Press, New York, NY, pp. 612-615 (1980).

Strauss, J. H. and Strauss, E. G., "The Alphaviruses: Gene Expression, Replication, and Evolution," *Microbiol. Rev. 58*:491-562 (1994), American Society for Microbiology.

Tanimori, H., et al., "Enzyme Immunoassay of Neocarzinostatin Using ꓱ-Galactosidase as Label," *J. Pharm. Dyn. 4*:812-819 (1981), Blackwell Publishing, Inc.

Topchieva, I. and Karezin, K., "Self-Assembled Supramolecular Micellar Structures Based on Non-ionic Surfactants and Cyclodextrins," *J. Colloid Interface Sci. 213*:29-35 (May 1999), Academic Press.

Townsend, A. and Bodmer, H., "Antigen Recognition by Class I-Restricted T Lymphocytes," *Ann. Rev. Immunol. 7*:601-624 (1989), Annual Reviews Inc.

Twomey, T., et al., "Structure and immunogenicity of experimental foot-and-mouth disease and poliomyelitis vaccines," *Vaccine 13*:1603-1610 (1995), Elsevier Science Ltd.

Ulrich, R., et al., "Core Particles of Hepatitis B Virus as Carrier for Foreign Epitopes," *Adv. in Virus Res. 50*:141-182 (Jan. 1998), Academic Press.

VanCott, T. C., et al., "Antibodies with Specificity to Native gp120 and Neutralization Activity against Primary Human Immunodeficiency Virus Type 1 Isolates Elicited by Immunization with Oligomeric gp160," *J. Virol. 71*:4319-4330 (Jun. 1997), American Society for Microbiology.

Warnes, A., et al., "Expression of the measles virus nucleoprotein gene in *Escherichia coli* and assembly of nucleocapsid-like structures," *Gene 160*:173-178 (1995), Elsevier Science B.V.

Watson, E., et al., "Structure determination of the intact major sialylated oligosaccharide chains of recombinant human erythropoietin expressed in Chinese hamster ovary cells," *Glycobiology 4*:227-237 (1994), Oxford University Press.

Xiong, C., et al., "Sindbis Virus: An Efficient, Broad Host Range Vector for Gene Expression in Animal Cells," *Science 243*:1188-1191 (1989), The American Association for the Advancement of Science.

Zang, M., et al., "Production of Recombinant Proteins in Chinese Hamster Ovary Cells Using a Protein-Free Cell Culture Medium," *Bio/technology 13*:389-392 (1995), Nature Publishing Company.

Invitrogen Manual, "Sindbis Expression System Version E," Catalog No. K750-01, Life Technologies (Apr. 2002).

Boorsma, M., et al., "A temperature-regulated replicon-based DNA expression system," *Nature Biotechnol. 18*:429-432 (Apr. 2000), Nature America Inc.

Esposito, G., et al., "Conformational study of a short *Pertussis* toxin T cell epitope incorporated in a multiple antigen peptide template by CD and two-dimensional NMR. Analysis of the structural effects on the activity of synthetic immunogens," *Eur. J. Biochem. 217*:171-187 (1993), Blackwell Science Ltd on behalf of the Federation of European Biochemical Societies.

Frolov, I., et al., "Alphavirus-based expression vectors: Strategies and applications," *Proc. Natl. Acad. Sci. USA 93*:11371-11377 (1996), National Academy Press.

Ebina, S., et al., "Chemical Modification of Bovine Pancreatic Trypsin Inhibitor for Single Site Coupling of Immunogenic Peptides for NMR Conformational Analysis," *J. Biol. Chem. 264*:7882-7888, American Society for Biochemistry and Molecular Biology, Inc. (1989).

Hui, E.K.-W., et al., "Hepatitis B viral core proteins with an N-terminal extension can assemble into core-like particles but cannot be enveloped," *J. Gen. Virol. 80*:2647-2659, Society for General Microbiology (Oct. 1999).

Lo, K.K.-W., et al., "Surface-modified mutants of cytochrome P450$_{cam}$:enzymatic properties and electrochemistry," *FEBS Lett. 451*:342-346, Elsevier Science B.V. (May 1999).

Rudolf, M.P., et al., "Molecular Basis for Nonanaphylactogenicity of a Monoclonal Anti-IgE Antibody," *J. Immunol. 165*:813-819, American Association of Immunologists (Jul. 2000).

Willis, A.E., et al., "Immunological properties of foreign peptides in multiple display on a filamentous bacteriophage," *Gene 128*:79-83, Elsevier Science Publishers B.V. (1993).

Zhou, S., and Standring, D.N., "Cys Residues of the Hepatitis B Virus Capsid Protein Are Not Essential for the Assembly of Viral Core Particles but Can Influence Their Stability," *J. Virol. 66*:5393-5398, American Society for Microbiology (1992).

International Preliminary Examination Report for International Application No. PCT/IB99/01925, search completed on Aug. 18, 2000, European Patent Office, Munich.

International Search Report for International Application No. PCT/IB99/01925, mailed on Jun. 29, 2000, European Patent Office, The Hague, Netherlands.

\* cited by examiner

SEQUENCE LISTING

<160> NUMBER OF SEQ ID NOS: 88

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 1
ggggacgcgt gcagcaggta accaccgtta aagaaggcac c     41

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 2
cggtggttac ctgctgcacg cgttgcttaa gcgacatgta gcgg     44

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
ccatgaggcc tacgatgccc     20

<210> SEQ ID NO 4
<211> LENGTH: 25

```
<212> TYPE: DNA
<213> ORGANISM: Artificial Sequence
<220> FEATURE:
<223> OTHER INFORMATION: Description of Artificial Sequence: Primer

<400> SEQUENCE: 4
ggcactcacg gcgcgcttta caggc                                          25

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 5
ccttctttaa cggtggttac ctgctggcaa ccaacgtggt tcatgac                  47

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 6
aagcatgctg cacgcgtgtg cggtggtcgg atcgcccggc                          40

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence: Primer

<400> SEQUENCE: 7
gggtctagat tcccaaccat tcccttatcc aggctttttg acaacgctat gctccgcgcc   60
catcgtctgc accagctggc ctttgacacc                                     90

<210> SEQ ID NO 8
<211> LENGTH: 108
<212> TYPE: DNA
<213> ORGANISM: Artificial Sequence
<220> FEATURE:
<223> OTHER INFORMATION: Description of Artificial Sequence: Primer

<400> SEQUENCE: 8
gggtctagaa ggaggtaaaa aacgatgaaa aagacagcta tcgcgattgc agtggcactg   60
gctggtttcg ctaccgtagc gcaggccttc ccaaccattc ccttatcc                108

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 9
cccgaattcc tagaagccac agctgccctc c                                   31

<210> SEQ ID NO 10
<211> LENGTH: 24
<212> TYPE: DNA
<213> ORGANISM: Artificial Sequence
<220> FEATURE:
```

<223> OTHER INFORMATION: Description of Artificial Sequence: Primer

<400> SEQUENCE: 10
cctgcggtgg tctgaccgac accc                                    24

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 11
ccgcggaaga gccaccgcaa ccaccgtgtg ccgccaggat g                  41

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 12
ctatcatcta gaatgaatag aggattcttt aac                           33

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:
    Modified ribosome binding site

<400> SEQUENCE: 13
aggaggtaaa aaacg                                              15

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence:
    signal peptide

<400> SEQUENCE: 14

Met Lys Lys Thr Ala Ile Ala Ile Ala Val Ala Leu Ala Gly Phe Ala
 1               5                  10                  15

Thr Val Ala Gln Ala
            20

<210> SEQ ID NO 15
<211> LENGTH: 46
<212> TYPE: PRT
<213> ORGANISM: Artificial Sequence
<220> FEATURE:
<223> OTHER INFORMATION: Description of Artificial Sequence:
    modified Fos construct

<400> SEQUENCE: 15

Cys Gly Gly Leu Thr Asp Thr Leu Gln Ala Glu Thr Asp Gln Val Glu
 1               5                  10                  15

Asp Glu Lys Ser Ala Leu Gln Thr Glu Ile Ala Asn Leu Leu Lys Glu
            20                  25                  30

Lys Glu Lys Leu Glu Phe Ile Leu Ala Ala His Gly Gly Cys
        35                  40                  45

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:
      peptide linker

<400> SEQUENCE: 16

Ala Ala Ala Ser Gly Gly
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:
      peptide linker

<400> SEQUENCE: 17

Gly Gly Ser Ala Ala Ala
 1               5

<210> SEQ ID NO 18
<211> LENGTH: 256
<212> TYPE: DNA
<213> ORGANISM: Artificial Sequence
<220> FEATURE:
<223> OTHER INFORMATION: Description of Artificial Sequence:
      Fos fusion construct

<400> SEQUENCE: 18
gaattcagga ggtaaaaaac gatgaaaaag acagctatcg cgattgcagt ggcactggct      60
ggtttcgcta ccgtagcgca ggcctgggtg ggggcggccg cttctggtgg ttgcggtggt     120
ctgaccgaca ccctgcaggc ggaaaccgac caggtggaag acgaaaaatc cgcgctgcaa     180
accgaaatcg cgaacctgct gaaagaaaaa gaaaagctgg agttcatcct ggcggcacac     240
ggtggttgct aagctt                                                     256

<210> SEQ ID NO 19
<211> LENGTH: 52
<212> TYPE: PRT
<213> ORGANISM: Artificial Sequence
<220> FEATURE:
<223> OTHER INFORMATION: Description of Artificial Sequence:
      Fos fusion construct

<400> SEQUENCE: 19

Ala Ala Ala Ser Gly Gly Cys Gly Gly Leu Thr Asp Thr Leu Gln Ala
 1               5                  10                  15

Glu Thr Asp Gln Val Glu Asp Glu Lys Ser Ala Leu Gln Thr Glu Ile
            20                  25                  30

Ala Asn Leu Leu Lys Glu Lys Glu Lys Leu Glu Phe Ile Leu Ala Ala
        35                  40                  45

His Gly Gly Cys
    50

<210> SEQ ID NO 20
<211> LENGTH: 261
<212> TYPE: DNA
<213> ORGANISM: Artificial Sequence
<220> FEATURE:
<223> OTHER INFORMATION: Description of Artificial Sequence: Fos fusion
      construct
<220> FEATURE:
<221> NAME/KEY: CDS
<222> LOCATION: (22)..(240)

<400> SEQUENCE: 20

```
gaattcagga ggtaaaaaac g atg aaa aag aca gct atc gcg att gca gtg         51
                        Met Lys Lys Thr Ala Ile Ala Ile Ala Val
                         1               5                  10 gca ctg gct ggt ttc gct acc gta gcg cag gcc tgc ggt ggt ctg acc         99
Ala Leu Ala Gly Phe Ala Thr Val Ala Gln Ala Cys Gly Gly Leu Thr
             15                  20                  25 gac acc ctg cag gcg gaa acc gac cag gtg gaa gac gaa aaa tcc gcg        147
Asp Thr Leu Gln Ala Glu Thr Asp Gln Val Glu Asp Glu Lys Ser Ala
         30                  35                  40 ctg caa acc gaa atc gcg aac ctg ctg aaa gaa aaa gaa aag ctg gag        195
Leu Gln Thr Glu Ile Ala Asn Leu Leu Lys Glu Lys Glu Lys Leu Glu
     45                  50                  55 ttc atc ctg gcg gca cac ggt ggt tgc ggt ggt tct gcg gcc gct            240
Phe Ile Leu Ala Ala His Gly Gly Cys Gly Gly Ser Ala Ala Ala
 60                  65                  70 gggtgtgggg atatcaagct t                                                 261
```

<210> SEQ ID NO 21
<211> LENGTH: 73
<212> TYPE: PRT
<213> ORGANISM: Artificial Sequence
<220> FEATURE:
<223> OTHER INFORMATION: Description of Artificial Sequence: Fos fusion
      construct

<400> SEQUENCE: 21

```
Met Lys Lys Thr Ala Ile Ala Ile Ala Val Ala Leu Ala Gly Phe Ala
 1               5                  10                  15

Thr Val Ala Gln Ala Cys Gly Gly Leu Thr Asp Thr Leu Gln Ala Glu
             20                  25                  30

Thr Asp Gln Val Glu Asp Glu Lys Ser Ala Leu Gln Thr Glu Ile Ala
         35                  40                  45

Asn Leu Leu Lys Glu Lys Glu Lys Leu Glu Phe Ile Leu Ala Ala His
     50                  55                  60

Gly Gly Cys Gly Gly Ser Ala Ala Ala
 65                  70
```

<210> SEQ ID NO 22
<211> LENGTH: 196
<212> TYPE: DNA
<213> ORGANISM: Artificial Sequence
<220> FEATURE:
<223> OTHER INFORMATION: Description of Artificial Sequence: Fos fusion
      construct
<220> FEATURE:
<221> NAME/KEY: CDS
<222> LOCATION: (34)..(189)

<400> SEQUENCE: 22

```
gaattcagga ggtaaaaaga tatcgggtgt ggg gcg gcc gct tct ggt ggt tgc        54
                                 Ala Ala Ala Ser Gly Gly Cys
                                  1               5 ggt ggt ctg acc gac acc ctg cag gcg gaa acc gac cag gtg gaa gac        102
Gly Gly Leu Thr Asp Thr Leu Gln Ala Glu Thr Asp Gln Val Glu Asp
         10                  15                  20
```

```
gaa aaa tcc gcg ctg caa acc gaa atc gcg aac ctg ctg aaa gaa aaa    150
Glu Lys Ser Ala Leu Gln Thr Glu Ile Ala Asn Leu Leu Lys Glu Lys
         25                  30                  35 gaa aag ctg gag ttc atc ctg gcg gca cac ggt ggt tgc taagctt        196
Glu Lys Leu Glu Phe Ile Leu Ala Ala His Gly Gly Cys
 40                  45                  50
```

<210> SEQ ID NO 23
<211> LENGTH: 52
<212> TYPE: PRT
<213> ORGANISM: Artificial Sequence
<220> FEATURE:
<223> OTHER INFORMATION: Description of Artificial Sequence: Fos fusion
      construct

<400> SEQUENCE: 23

```
Ala Ala Ala Ser Gly Gly Cys Gly Gly Leu Thr Asp Thr Leu Gln Ala
 1               5                  10                  15

Glu Thr Asp Gln Val Glu Asp Glu Lys Ser Ala Leu Gln Thr Glu Ile
             20                  25                  30

Ala Asn Leu Leu Lys Glu Lys Glu Lys Leu Glu Phe Ile Leu Ala Ala
         35                  40                  45

His Gly Gly Cys
     50
```

<210> SEQ ID NO 24
<211> LENGTH: 204
<212> TYPE: DNA
<213> ORGANISM: Artificial Sequence
<220> FEATURE:
<223> OTHER INFORMATION: Description of Artificial Sequence: Fos fusion
      construct

<400> SEQUENCE: 24

```
gaattcagga ggtaaaaaac gatggcttgc ggtggtctga ccgacaccct gcaggcggaa     60
accgaccagg tggaagacga aaatccgcg ctgcaaaccg aaatcgcgaa cctgctgaaa    120 gaaaagaaa agctggagtt catcctggcg gcacacggtg gttgcggtgg ttctgcggcc    180
gctgggtgtg gggatatcaa gctt                                          204
```

<210> SEQ ID NO 25
<211> LENGTH: 56
<212> TYPE: PRT
<213> ORGANISM: Artificial Sequence
<220> FEATURE:
<223> OTHER INFORMATION: Description of Artificial Sequence: Fos fusion
      construct

<400> SEQUENCE: 25

```
Lys Thr Met Ala Cys Gly Gly Leu Thr Asp Thr Leu Gln Ala Glu Thr
 1               5                  10                  15

Asp Gln Val Glu Asp Glu Lys Ser Ala Leu Gln Thr Glu Ile Ala Asn
             20                  25                  30

Leu Leu Lys Glu Lys Glu Lys Leu Glu Phe Ile Leu Ala Ala His Gly
         35                  40                  45

Gly Cys Gly Gly Ser Ala Ala Ala
     50                  55
```

<210> SEQ ID NO 26
<211> LENGTH: 26
<212> TYPE: PRT
<213> ORGANISM: Homo sapiens

```
<400> SEQUENCE: 26

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 27
<211> LENGTH: 262
<212> TYPE: DNA
<213> ORGANISM: Artificial Sequence
<220> FEATURE:
<223> OTHER INFORMATION: Description of Artificial Sequence: Fos fusion
      construct

<400> SEQUENCE: 27
gaattcaggc ctatggctac aggctcccgg acgtccctgc tcctggcttt tggcctgctc      60
tgcctgccct ggcttcaaga gggcagcgct gggtgtgggg cggccgcttc tggtggttgc     120
ggtggtctga ccgacaccct gcaggcggaa accgaccagg tggaagacga aaaatccgcg     180
ctgcaaaccg aaatcgcgaa cctgctgaaa gaaaagaaa agctggagtt catcctggcg     240
gcacacggtg gttgctaagc tt                                              262

<210> SEQ ID NO 28
<211> LENGTH: 52
<212> TYPE: PRT
<213> ORGANISM: Artificial Sequence
<220> FEATURE:
<223> OTHER INFORMATION: Description of Artificial Sequence: Fos fusion
      construct

<400> SEQUENCE: 28

Ala Ala Ala Ser Gly Gly Cys Gly Gly Leu Thr Asp Thr Leu Gln Ala
                5                   10                  15

Glu Thr Asp Gln Val Glu Asp Glu Lys Ser Ala Leu Gln Thr Glu Ile
            20                  25                  30

Ala Asn Leu Leu Lys Glu Lys Glu Lys Leu Glu Phe Ile Leu Ala Ala
        35                  40                  45

His Gly Gly Cys
    50

<210> SEQ ID NO 29
<211> LENGTH: 261
<212> TYPE: DNA
<213> ORGANISM: Artificial Sequence
<220> FEATURE:
<223> OTHER INFORMATION: Description of Artificial Sequence: Fos fusion
      construct
<220> FEATURE:
<221> NAME/KEY: CDS
<222> LOCATION: (7)..(240)

<400> SEQUENCE: 29 gaattc atg gct aca ggc tcc cgg acg tcc ctg ctc ctg gct ttt ggc        48
       Met Ala Thr Gly Ser Arg Thr Ser Leu Leu Leu Ala Phe Gly
       1               5                   10 ctg ctc tgc ctg ccc tgg ctt caa gag ggc agc gct tgc ggt ggt ctg       96
Leu Leu Cys Leu Pro Trp Leu Gln Glu Gly Ser Ala Cys Gly Gly Leu
15                  20                  25                  30 acc gac acc ctg cag gcg gaa acc gac cag gtg gaa gac gaa aaa tcc      144
Thr Asp Thr Leu Gln Ala Glu Thr Asp Gln Val Glu Asp Glu Lys Ser
                35                  40                  45 gcg ctg caa acc gaa atc gcg aac ctg ctg aaa gaa aaa gaa aag ctg      192
```

```
                                                    -continued

Ala Leu Gln Thr Glu Ile Ala Asn Leu Leu Lys Glu Lys Glu Lys Leu
            50                  55                  60 gag ttc atc ctg gcg gca cac ggt ggt tgc ggt ggt tct gcg gcc gct      240
Glu Phe Ile Leu Ala Ala His Gly Gly Cys Gly Gly Ser Ala Ala Ala
            65                  70                  75 gggtgtggga ggcctaagct t                                              261

<210> SEQ ID NO 30
<211> LENGTH: 78
<212> TYPE: PRT
<213> ORGANISM: Artificial Sequence
<220> FEATURE:
<223> OTHER INFORMATION: Description of Artificial Sequence: Fos fusion
      construct

<400> SEQUENCE: 30

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Cys Gly Gly Leu Thr Asp
            20                  25                  30

Thr Leu Gln Ala Glu Thr Asp Gln Val Glu Asp Glu Lys Ser Ala Leu
            35                  40                  45

Gln Thr Glu Ile Ala Asn Leu Leu Lys Glu Lys Glu Lys Leu Glu Phe
        50                  55                  60

Ile Leu Ala Ala His Gly Gly Cys Gly Gly Ser Ala Ala Ala
 65                 70                  75

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 31
cctgggtggg ggcggccgct tctggtggtt gcggtggtct gacc                      44

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 32
ggtgggaatt caggaggtaa aaagatatcg ggtgtggggc ggcc                      44

<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 33
ggtgggaatt caggaggtaa aaaacgatgg cttgcggtgg tctgacc                   47

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 34
gcttgcggtg gtctgacc                                                    18

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 35
ccaccaagct tagcaaccac cgtgtgc                                          27

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 36
ccaccaagct tgatatcccc acacccagcg ccgcagaac caccgcaacc accg            54

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 37
ccaccaagct taggcctccc acacccagcg gc                                    32

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 38
ggtgggaatt caggaggtaa aaaacgatg                                        29

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 39
ggtgggaatt caggcctatg gctacaggct cc                                    32

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 40
ggtgggaatt catggctaca ggctccc                                          27

<210> SEQ ID NO 41
<211> LENGTH: 59
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 41
gggtctagaa tggctacagg ctcccggacg tccctgctcc tggcttttgg cctgctctg      59

<210> SEQ ID NO 42
<211> LENGTH: 58
<212> TYPE: DNA
<213> ORGANISM: Artificial Sequence
<220> FEATURE:
<223> OTHER INFORMATION: Description of Artificial Sequence: Primer

<400> SEQUENCE: 42
cgcaggcctc ggcactgccc tcttgaagcc agggcaggca gagcaggcca aaagccag       58

<210> SEQ ID NO 43
<211> LENGTH: 402
<212> TYPE: DNA
<213> ORGANISM: Artificial Sequence
<220> FEATURE:
<223> OTHER INFORMATION: Description of Artificial Sequence:
      Modified bee venom phospholipase A2
<220> FEATURE:
<221> NAME/KEY: CDS
<222> LOCATION: (1)..(402)

<400> SEQUENCE: 43 atc atc tac cca ggt act ctg tgg tgt ggt cac ggc aac aaa tct tct      48
Ile Ile Tyr Pro Gly Thr Leu Trp Cys Gly His Gly Asn Lys Ser Ser
 1               5                  10                  15 ggt ccg aac gaa ctc ggc cgc ttt aaa cac acc gac gca tgc tgt cgc      96
Gly Pro Asn Glu Leu Gly Arg Phe Lys His Thr Asp Ala Cys Cys Arg
            20                  25                  30 acc cag gac atg tgt ccg gac gtc atg tct gct ggt gaa tct aaa cac     144
Thr Gln Asp Met Cys Pro Asp Val Met Ser Ala Gly Glu Ser Lys His
        35                  40                  45 ggg tta act aac acc gct tct cac acg cgt ctc agc tgc gac tgc gac     192
Gly Leu Thr Asn Thr Ala Ser His Thr Arg Leu Ser Cys Asp Cys Asp
    50                  55                  60 gac aaa ttc tac gac tgc ctt aag aac tcc gcc gat acc atc tct tct     240
Asp Lys Phe Tyr Asp Cys Leu Lys Asn Ser Ala Asp Thr Ile Ser Ser
65                  70                  75                  80 tac ttc gtt ggt aaa atg tat ttc aac ctg atc gat acc aaa tgt tac     288
Tyr Phe Val Gly Lys Met Tyr Phe Asn Leu Ile Asp Thr Lys Cys Tyr
                85                  90                  95 aaa ctg gaa cac ccg gta acc ggc tgc ggc gaa cgt acc gaa ggt cgc     336
Lys Leu Glu His Pro Val Thr Gly Cys Gly Glu Arg Thr Glu Gly Arg
            100                 105                 110 tgc ctg cac tac acc gtt gac aaa tct aaa ccg aaa gtt tac cag tgg     384
Cys Leu His Tyr Thr Val Asp Lys Ser Lys Pro Lys Val Tyr Gln Trp
        115                 120                 125 ttc gac ctg cgc aaa tac                                              402
Phe Asp Leu Arg Lys Tyr
    130

<210> SEQ ID NO 44
<211> LENGTH: 134
<212> TYPE: PRT
<213> ORGANISM: Artificial Sequence
<220> FEATURE:
<223> OTHER INFORMATION: Description of Artificial Sequence:
      Modified bee venom phospholipase A2
```

<400> SEQUENCE: 44

| | | | | | | | | | | | | | | | |
|---|---|---|---|---|---|---|---|---|---|---|---|---|---|---|---|
|Ile|Ile|Tyr|Pro|Gly|Thr|Leu|Trp|Cys|Gly|His|Gly|Asn|Lys|Ser|Ser|
|1| | | |5| | | |10| | | |15| | | |

Gly Pro Asn Glu Leu Gly Arg Phe Lys His Thr Asp Ala Cys Cys Arg
            20                  25                  30

Thr Gln Asp Met Cys Pro Asp Val Met Ser Ala Gly Glu Ser Lys His
        35                  40                  45

Gly Leu Thr Asn Thr Ala Ser His Thr Arg Leu Ser Cys Asp Cys Asp
    50                  55                  60

Asp Lys Phe Tyr Asp Cys Leu Lys Asn Ser Ala Asp Thr Ile Ser Ser
65                  70                  75                  80

Tyr Phe Val Gly Lys Met Tyr Phe Asn Leu Ile Asp Thr Lys Cys Tyr
                85                  90                  95

Lys Leu Glu His Pro Val Thr Gly Cys Gly Glu Arg Thr Glu Gly Arg
            100                 105                 110

Cys Leu His Tyr Thr Val Asp Lys Ser Lys Pro Lys Val Tyr Gln Trp
        115                 120                 125

Phe Asp Leu Arg Lys Tyr
    130

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 45
ccatcatcta cccaggtac                                              19

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 46
cccacaccca gcggccgcgt atttgcgcag gtcg                             34

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 47
cggtggttct gcggccgcta tcatctaccc aggtac                           36

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 48
ttagtatttg cgcaggtcg                                              19

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 49
ccggctccat cggtgcag                                                 18

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 50
accaccagaa gcggccgcag gggaaacaca tctgcc                             36

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 51
cggtggttct gcggccgctg gctccatcgg tgcag                              35

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 52
ttaaggggaa acacatctgc c                                             21

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 53
actagtctag aatgagagtg aaggagaaat atc                                33

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 54
tagcatgcta gcaccgaatt tatctaattc caataattct tg                      42

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence: Primer -continued

```
<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 56
caaagctcct attcccactg ccagtttctc gagctgggta gctttcag                    48

<210> SEQ ID NO 57
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 57
ttcggtgcta gcggtggctg cggtggtctg accgac                                 36

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 58
gatgctgggc ccttaaccgc aaccaccgtg tgccgcc                                37

<210> SEQ ID NO 59
<211> LENGTH: 46
<212> TYPE: PRT
<213> ORGANISM: Artificial Sequence
<220> FEATURE:
<223> OTHER INFORMATION: Description of Artificial Sequence:
      JUN amino acid sequence

<400> SEQUENCE: 59

Cys Gly Gly Arg Ile Ala Arg Leu Glu Glu Lys Val Lys Thr Leu Lys
 1               5                  10                  15

Ala Gln Asn Ser Glu Leu Ala Ser Thr Ala Asn Met Leu Arg Glu Gln
            20                  25                  30

Val Ala Gln Leu Lys Gln Lys Val Met Asn His Val Gly Cys
        35                  40                  45

<210> SEQ ID NO 60
<211> LENGTH: 46
<212> TYPE: PRT
<213> ORGANISM: Artificial Sequence
<220> FEATURE:
<223> OTHER INFORMATION: Description of Artificial Sequence:  FOS amino
      acid sequence

<400> SEQUENCE: 60

Cys Gly Gly Leu Thr Asp Thr Leu Gln Ala Glu Thr Asp Gln Val Glu
 1               5                  10                  15

Asp Glu Lys Ser Ala Leu Gln Thr Glu Ile Ala Asn Leu Leu Lys Glu
            20                  25                  30

Lys Glu Lys Leu Glu Phe Ile Leu Ala Ala His Gly Gly Cys
        35                  40                  45
```

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 61
ccggaattca tgtgcggtgg tcggatcgcc cgg                               33

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 62
gtcgctaccc gcggctccgc aaccaacgtg gttcatgac                         39

<210> SEQ ID NO 63
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 63
gttggttgcg gagccgcggg tagcgacatt gacccttata aagaatttgg             50

<210> SEQ ID NO 64
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 64
cgcgtcccaa gcttctacgg aagcgttgat aggatagg                          38

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 65
ctagccgcgg gttgcggtgg tcggatcgcc cgg                               33

<210> SEQ ID NO 66
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 66
cgcgtcccaa gcttttagca accaacgtgg ttcatgac                          38

<210> SEQ ID NO 67
<211> LENGTH: 31
<212> TYPE: DNA
<213> ORGANISM: Artificial Sequence
<220> FEATURE:

<223> OTHER INFORMATION: Description of Artificial Sequence: Primer

<400> SEQUENCE: 67
ccggaattca tggacattga cccttataaa g                            31

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 68
ccgaccaccg caacccgcgg ctagcggaag cgttgatagg atagg             45

<210> SEQ ID NO 69
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 69
ctaatggatc cggtgggggc tgcggtggtc ggatcgcccg gctcgag           47

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 70
gtcgctaccc gcggctccgc aaccaacgtg gttcatgac                    39

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 71
ccggaattca tggacattga cccttataaa g                            31

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 72
ccgaccaccg cagcccccac cggatccatt agtacccacc caggtagc          48

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 73
gttggttgcg gagccgcggg tagcgaccta gtagtcagtt atgtc             45

<210> SEQ ID NO 74
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 74
cgcgtcccaa gcttctacgg aagcgttgat aggatagg                    38

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 75
ctagccgcgg gttgcggtgg tcggatcgcc cgg                          33

<210> SEQ ID NO 76
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 76
cgcgtcccaa gcttttagca accaacgtgg ttcatgac                    38

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 77
ccggaattca tggccacact tttaaggagc                              30

<210> SEQ ID NO 78
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 78
cgcgtcccaa gcttttagca accaacgtgg ttcatgac                    38

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 79
ccggaattca tggacattga cccttataaa g                           31

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 80
cctagagcca cctttgccac catcttctaa attagtaccc acccaggtag c            51

<210> SEQ ID NO 81
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 81
gaagatggtg gcaaaggtgg ctctagggac ctagtagtca gttatgtc               48

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 82
cgcgtcccaa gcttctaaac aacagtagtc tccggaag                          38

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 83
gccgaattcc tagcagctag caccgaattt atctaa                            36

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 84
ggttaagtcg acatgagagt gaaggagaaa tat                               33

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 85
taaccgaatt caggaggtaa aaagatatgg                                   30

<210> SEQ ID NO 86
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 86
gaagtaaagc ttttaaccac cgcaaccacc agaag                             35

<210> SEQ ID NO 87
<211> LENGTH: 33

```
<212> TYPE: DNA
<213> ORGANISM: Artificial Sequence
<220> FEATURE:
<223> OTHER INFORMATION: Description of Artificial Sequence: Primer

<400> SEQUENCE: 87
tcgaatgggc cctcatcttc gtgtgctagt cag                                    33

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Fos fusion
      construct

<400> SEQUENCE: 88

Glu Phe Arg Arg
  1
```

ORDERED MOLECULAR PRESENTATION OF ANTIGENS, METHOD OF PREPARATION AND USE

CROSS REFERENCE TO RELATED APPLICATIONS

This application is a continuation of U.S. patent application Ser. No. 09/449,631, filed Nov. 30, 1999 now abandoned; which claims the benefit of the filing date of provisional applications 60/142,788, filed on Jul. 8, 1999; and 60/110,414, filed on Nov. 30, 1998; all of which are herein incorporated by reference.

BACKGROUND OF THE INVENTION

1. Field of the Invention

The present invention is related to the fields of molecular biology, virology, immunology and medicine. The invention provides a composition comprising an ordered and repetitive antigen or antigenic determinant array. The invention also provides a process for producing an antigen or antigenic determinant in an ordered and repetitive array. The ordered and repetitive antigen or antigenic determinant is useful in the production of vaccines for the treatment of infectious diseases, the treatment of allergies and as a pharmaccine to prevent or cure cancer and to generate defined self-specific antibodies.

2. Related Art

Vaccine development for the prevention of infectious disease has had the greatest impact on human health of any medical invention. It is estimated that three million deaths per year are prevented worldwide by vaccination (Hillemann, *Nature Medicine* 4:507 (1998)). The most common vaccination strategy, the use of attenuated (i.e. less virulent) pathogens or closely related organisms, was first demonstrated by Edward Jenner in 1796, who vaccinated against smallpox by the administration of a less dangerous cowpox virus. Although a number of live attenuated viruses (e.g. measles, mumps, rubella, varicella, adenovirus, polio, influenza) and bacteria (e.g. bacille Calmette-Guerin (BCG) against tuberculosis) are successfully administered for vaccination, there is a risk for the development of serious complications related to a reversion to virulence and infection by the 'vaccine' organism, in particular in immunocompromised individuals.

The specific design of attenuated viruses is now enabled by recombinant DNA technology (i.e., genetic engineering) through the generation of deletion or mutation variants. For example, the administration of an engineered Simian Immunodeficiency Virus (SIV) with a deletion within the nef gene was shown to protect macaques from subsequent infection with a pathogenic SIV strain (Daniel et al., *Science* 258: 1938–1941 (1992)). However, the progression of acquired immunodeficiency syndrome (AIDS)-like symptoms in animals administered attenuated SIV raises safety concerns (Baba et al., *Science* 267:1820–1825 ((1995)).

As an alternative approach, attenuated viruses or bacteria may be used as carriers for the antigen-encoding genes of a pathogen that is considered too unsafe to be administered in an attenuated form (e.g., Human Immunodeficiency Virus (HIV)). Upon delivery of the antigen-encoding gene to the host, the antigen is synthesized in situ. Vaccinia and related avipox viruses have been used as such carriers for various genes in preclinical and clinical studies for a variety of diseases (e.g., Shen et al., *Science* 252:440 (1991)). One disadvantage of this vaccination strategy is that it does not mimic the virion surface, because the recombinant protein is expressed on the surface of the host cell. Additionally, complications may develop in immunocompromised individuals, as evidenced by life-threatening disseminated vaccinia infections (Redfield, *N. Eng. J. Med.* 316:673 ((1998)).

A fourth vaccination approach involves the use of isolated components of a pathogen, either purified from the pathogen grown in vitro (e.g. influenza hemagglutinin or neuraminidase) or after heterologous expression of a single viral protein (e.g. hepatitis B surface antigen). For example, recombinant, mutated toxins (detoxified) are used for vaccination against diphtheria, tetanus, cholera and pertussis toxins (Levine et al., *New generation vaccines*, 2nd edn., Marcel Dekker, Inc., New York 1997), and recombinant proteins of HIV (gp120 and full-length gp160) were evaluated as a means to induce neutralizing antibodies against HIV with disappointing results (Connor et al., *J. Virol.* 72:1552 (1998)). Recently, promising results were obtained with soluble oligomeric gp160, that can induce CTL response and elicit antibodies with neutralizing activity against HIV-1 isolates (Van Cortt et al., *J. Virol.* 71:4319 (1997)). In addition, peptide vaccines may be used in which known B- or T-cell epitopes of an antigen are coupled to a carrier molecule designed to increase the immunogenicity of the epitope by stimulating T-cell help. However, one significant problem with this approach is that it provides a limited immune response to the protein as a whole. Moreover, vaccines have to be individually designed for different MHC haplotypes. The most serious concern for this type of vaccine is that protective antiviral antibodies recognize complex, three-dimensional structures that cannot be mimicked by peptides.

A more novel vaccination strategy is the use of DNA vaccines (Donnelly et al., *Ann. Rev. Immunol.* 15:617 (1997)), which may generate MHC Class I-restricted CTL responses (without the use of a live vector). This may provide broader protection against different strains of a virus by targeting epitopes from conserved internal proteins pertinent to many strains of the same virus. Since the antigen is produced with mammalian post-translational modification, conformation and oligomerization, it is more likely to be similar or identical to the wild-type protein produced by viral infection than recombinant or chemically modified proteins. However, this distinction may turn out to be a disadvantage for the application of bacterial antigens, since non-native post-translational modification may result in reduced immunogenicity. In addition, viral surface proteins are not highly organized in the absence of matrix proteins.

In addition to applications for the prevention of infectious disease, vaccine technology is now being utilized to address immune problems associated with allergies. In allergic individuals, antibodies of the IgE isotype are produced in an inappropriate humoral immune response towards particular antigens (allergens). The treatment of allergies by allergy immunotherapy requires weekly administration of successively increasing doses of the particular allergen over a period of up to 3–5 years. Presumably, 'blocking' IgG antibodies are generated that intercept allergens in nasal or respiratory secretions or in membranes before they react with IgE antibodies on mast cells. However, no constant relationship exists between IgG titers and symptom relief. Presently, this is an extremely time- and cost-consuming process, to be considered only for patients with severe symptoms over an extended period each year.

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen.

Unlike isolated proteins, viruses induce prompt and efficient immune responses in the absence of any adjuvants both with and without T-cell help (Bachmann & Zinkernagel, *Ann. Rev. Immunol.* 15:235–270 (1997)). Although viruses often consist of few proteins, they are able to trigger much stronger immune responses than their isolated components. For B cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann & Zinkernagel, *Immunol. Today* 17:553–558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann & Zinkemagel, *Ann. Rev. Immunol.* 15:235–270 (1997)). Viral structure is even linked to the generation of anti-antibodies in autoimmune disease and as a part of the natural response to pathogens (see Fehr, T., et al., *J. Exp. Med.* 185:1785–1792 (1997)). Thus, antigens on viral particles that are organized in an ordered and repetitive array are highly immunogenic since they can directly activate B cells.

In addition to strong B cell responses, viral particles are also able to induce the generation of a cytotoxic T cell response, another crucial arm of the immune system. These cytotoxic T cells are particularly important for the elimination of non-cytopathic viruses such as HIV or hepatitis B virus and for the eradication of tumors. Cytotoxic T cells do not recognize native antigens but rather recognize their degradation products in association with MHC class I molecules (Townsend & Bodmer, *Ann. Rev. Immunol.* 7:601–624 (1989)). Macrophages and dendritic cells are able to take up and process exogenous viral particles (but not their soluble, isolated components) and present the generated degradation product to cytotoxic T cells, leading to their activation and proliferation (Kovacsovics-Bankowski et al., *Proc. Natl. Acad. Sci. USA* 90:4942–4946 (1993); Bachmann et al., *Eur. J. Immunol.* 26:2595–2600 (1996)).

Viral particles as antigens exhibit two advantages over their isolated components: (1) Due to their highly repetitive surface structure, they are able to directly activate B cells, leading to high antibody titers and long-lasting B cell memory; and (2) Viral particles but not soluble proteins are able to induce a cytotoxic T cell response, even if the viruses are non-infectious and adjuvants are absent.

Several new vaccine strategies exploit the inherent immunogenicity of viruses. Some of these approaches focus on the particulate nature of the virus particle; for example see Harding, C. V. and Song, R., (*J. Immunology* 153:4925 (1994)), which discloses a vaccine consisting of latex beads and antigen; Kovacsovics-Bankowski, M., et al. (*Proc. Natl. Acad. Sci. USA* 90:4942–4946 (1993)), which discloses a vaccine consisting of iron oxide beads and antigen; U.S. Pat. No. 5,334,394 to Kossovsky, N., et al., which discloses core particles coated with antigen; U.S. Pat. No. 5,871,747, which discloses synthetic polymer particles carrying on the surface one or more proteins covalently bonded thereto; and a core particle with a non-covalently bound coating, which at least partially covers the surface of said core particle, and at least one biologically active agent in contact with said coated core particle (see, e.g., WO/94/15585).

However, a disadvantage of these viral mimicry systems is that they are not able to recreate the ordered presentation of antigen found on the viral surface. Antigens coupled to a surface in a random orientation are found to induce CTL response and no or only weak B-cell response. For an efficient vaccine, both arms of the immune system have to be strongly activated, as described above and in Bachmann & Zinkemagel, *Ann. Rev. Immunol.* 15:235 (1997).

In another example, recombinant viruses are being utilized for antigen delivery. Filamentous phage virus containing an antigen fused to a capsid protein has been found to be highly immunogenic (see Perham R. N., et al., *FEMS Microbiol. Rev.* 17:25–31 (1995); Willis et al., *Gene* 128: 85–88 (1993); Minenkova et al., *Gene* 128:85–88 (1993)). However, this system is limited to very small peptides (5 or 6 amino acid residues) when the fusion protein is expressed at a high level (Iannolo et al., *J. Mol. Biol.* 248:835–844 (1995)) or limited to the low level expression of larger proteins (de la Cruz et al., *J. Biol. Chem.* 263:4318–4322 (1988)). For small peptides, so far only the CTL response is observed and no or only weak B-cell response.

In yet another system, recombinant alphaviruses are proposed as a means of antigen delivery (see U.S. Pat. Nos. 5,766,602; 5,792,462; 5,739,026; 5;789,245 and 5,814,482). Problems with the recombinant virus systems described so far include a low density expression of the heterologous protein on the viral surface and/or the difficulty of successfully and repeatedly creating a new and different recombinant viruses for different applications.

In a further development, virus-like particles (VLPs) are being exploited in the area of vaccine production because of both their structural properties and their non-infectious nature. VLPs are supermolecular structures built in a symmetric manner from many protein molecules of one or more types. They lack the viral genome and, therefore, are non-infectious. VLPs can often be produced in large quantities by heterologous expression and can be easily be purified.

Examples of VLPs include the capsid proteins of hepatitis B virus (Ulrich, et al., *Virus Res.* 50:141–182 (1998)), measles virus (Wames, et al., *Gene* 160:173–178 (1995)), Sindbis virus, rotavirus (U.S. Pat. Nos. 5,071,651 and 5,374, 426), foot-and-mouth-disease virus (Twomey, et al., Vaccine 13: 1603–1610, (1995)), Norwalk virus (Jiang, X., et al., *Science* 250:1580–1583 (1990); Matsui, S. M., et al., *J. Clin. Invest.* 87:1456–1461 (1991)), the retroviral GAG protein (PCT Patent Appl. No. WO 96/30523), the retrotransposon Ty protein p1, the surface protein of Hepatitis B virus (WO 92/11291) and human papilloma virus (WO 98/15631). In some instances, recombinant DNA technology may be utilized to fuse a heterologous protein to a VLP protein (Kratz, P. A., et al., *Proc. Natl. Acad. Sci. USA* 96: 19151920 (1999)).

Thus, there is a need in the art for the development of new and improved vaccines that promote a strong CTL and B-cell immune response as efficiently as natural pathogens.

SUMMARY OF THE INVENTION

The invention provides a versatile new technology that allows production of particles coated with any desired antigen. The technology allows the creation of highly efficient vaccines against infectious diseases and for the creation of vaccines for the treatment of allergies and cancers.

In a first embodiment, the invention provides a novel composition comprising (A) a non-natural molecular scaffold and (B) an antigen or antigenic determinant.

The non-natural molecular scaffold comprises (i) a core particle selected from the group consisting of (1) a core particle of non-natural origin and (2) a core particle of natural origin; and (ii) an organizer comprising at least one first attachment site, wherein said organizer is connected to said core particle by at least one covalent bond.

The antigen or antigenic determinant has at least one second attachment site which is selected from the group consisting of (i) an attachment site not naturally occurring with said antigen or antigenic determinant; and (ii) an attachment site naturally occurring with said antigen or antigenic determinant.

The invention provides for an ordered and repetitive antigen array through an association of the second attachment site to the first attachment site by way of at least one non-peptide bond. Thus, the antigen or antigenic determinant and the non-natural molecular scaffold are brought together through this association of the first and the second attachment site to form an ordered and repetitive antigen array.

In another embodiment, the core particle of the aforementioned composition comprises a virus, a virus-like particle, a bacteriophage, a viral capsid particle or a recombinant form thereof. Alternatively, the core particle may be a synthetic polymer or a metal.

In a particular embodiment, the organizer may comprise at least one first attachment site. The first and the second attachment sites are particularly important elements of the composition of the invention. In various embodiments of the invention, the first and/or the second attachment site may be an antigen and an antibody or antibody fragment thereto; biotin and avidin; strepavidin and biotin; a receptor and its ligand; a ligand-binding protein and its ligand; interacting leucine zipper polypeptides; an amino group and a chemical group reactive thereto; a carboxyl group and a chemical group reactive thereto; a sulfhydryl group and a chemical group reactive thereto; or a combination thereof.

In a more preferred embodiment, the invention provides the coupling of almost any antigen of choice to the surface of a virus, bacteriophage, virus-like particle or viral capsid particle. By bringing an antigen into a quasi-crystalline 'virus-like' structure, the invention exploits the strong antiviral immune reaction of a host for the production of a highly efficient immune response, i.e., a vaccination, against the displayed antigen.

In one preferred embodiment, the core particle may be selected from the group consisting of: recombinant proteins of Rotavirus, recombinant proteins of Norwalkvirus, recombinant proteins of Alphavirus, recombinant proteins of Foot and Mouth Disease virus, recombinant proteins of Retrovirus, recombinant proteins of Hepatitis B virus, recombinant proteins of Tobacco mosaic virus, recombinant proteins of Flock House Virus, and recombinant proteins of human Papilomavirus.

In another preferred embodiment, the antigen may be selected from the group consisting of: (1) a protein suited to induce an immune response against cancer cells; (2) a protein suited to induce an immune response against infectious diseases; (3) a protein suited to induce an immune response against allergens; and (4) a protein suited to induce an immune response in farm animals.

In a particularly preferred embodiment of the invention, the first attachment site and/or the second attachment site comprise an interacting leucine zipper polypeptide. In most preferred embodiment, the first attachment site and/or the second attachment site are selected from the group comprising: (1) the JUN leucine zipper protein domain; and (2) the FOS leucine zipper protein domain.

In another preferred embodiment, the first attachment site and/or the second attachment site are selected from the group comprising: (1) a genetically engineered lysine residue and (2) a genetically engineered cysteine residue, two residues that may be chemically linked together.

Other embodiments of the invention include processes for the production of the compositions of the invention and a methods of medical treatment using said compositions.

It is to be understood that both the foregoing general description and the following detailed description are exemplary and explanatory only and are intended to provide further explanation of the invention as claimed.

DETAILED DESCRIPTION OF THE PREFERRED EMBODIMENTS

1. Definitions

Figure 1:
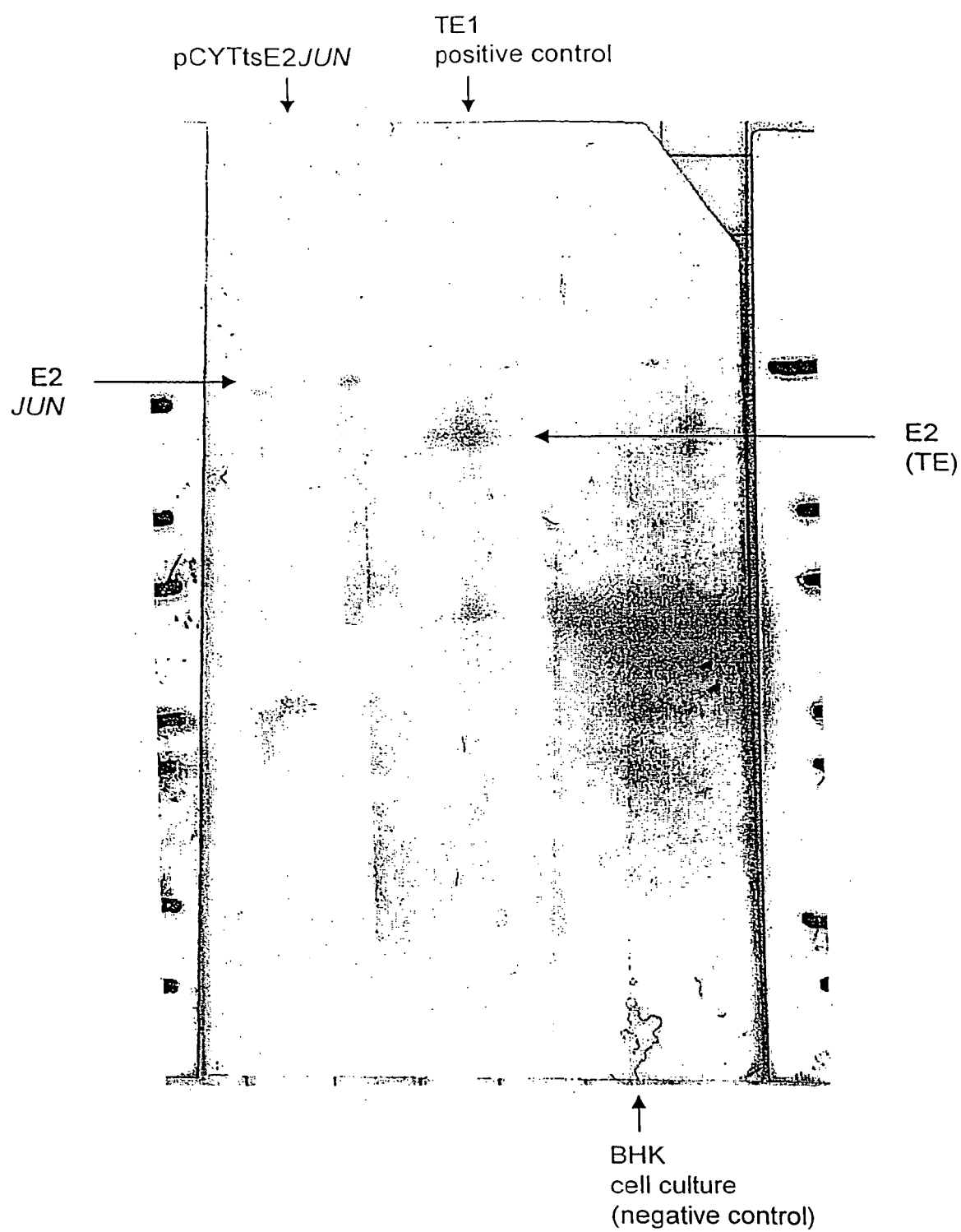
FIG. 1 Western blot demonstrating the production of viral particles containing the E2-JUN fusion protein using the pCYTts::E2JUN expression vector.

The following definitions are provided to clarify the subject matter which the inventors consider to be the present invention.

Alphavirus: As used herein, the term "alphavirus" refers to any of the RNA viruses included within the genus Alphavirus. Descriptions of the members of this genus are contained in Strauss and Strauss, *Microbiol. Rev.*, 58:491–562 (1994). Examples of alphaviruses include Aura virus, Bebaru virus, Cabassou virus, Chikungunya virus, Easter equine encephalomyelitis virus, Fort morgan virus, Getah virus, Kyzylagach virus, Mayoaro virus, Middleburg virus, Mucambo virus, Ndumu virus, Pixuna virus, Tonate virus, Triniti virus, Una virus, Western equine encephalomyelitis virus, Whataroa virus, Sindbis virus (SIN), Semliki forest virus (SFV), Venezuelan equine encephalomyelitis virus (VEE), and Ross River virus.

Antigen: As used herein, the term "antigen" is a molecule capable of being bound by an antibody. An antigen is additionally capable of inducing a humoral immune response and/or cellular immune response leading to the production of B- and/or T-lymphocytes. An antigen may have one or more epitopes (B- and T-epitopes). The specific reaction referred to above is meant to indicate that the antigen will react, in a highly selective manner, with its corresponding antibody and not with the multitude of other antibodies which may be evoked by other antigens.

Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors.

Association: As used herein, the term "association" as it applies to the first and second attachment sites, is used to refer to at least one non-peptide bond. The nature of the association may be covalent, ionic, hydrophobic, polar or any combination thereof.

Attachment Site, First: As used herein, the phrase "first attachment site" refers to an element of the "organizer", itself bound to the core particle in a non-random fashion, to which the second attachment site located on the antigen or antigenic determinant may associate. The first attachment site may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. Multiple first attachment sites are present on the surface of the non-natural molecular scaffold in a repetitive configuration.

Attachment Site, Second: As used herein, the phrase "second attachment site" refers to an element associated with the antigen or antigenic determinant to which the first attachment site of the "organizer" located on the surface of the non-natural molecular scaffold may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant.

Core particle: As used herein, the term "core particle" refers to a rigid structure with an inherent repetitive organization that provides a foundation for attachment of an "organizer". A core particle as used herein may be the product of a synthetic process or the product of a biological process.

Cis-acting: As used herein, the phrase "cis-acting" sequence refers to nucleic acid sequences to which a replicase binds to catalyze the RNA-dependent replication of RNA molecules. These replication events result in the replication of the full-length and partial RNA molecules and, thus, the alpahvirus subgenomic promoter is also a "cis-acting" sequence. Cis-acting sequences may be located at or near the 5' end, 3' end, or both ends of a nucleic acid molecule, as well as internally.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Heterologous sequence: As used herein, the term "heterologous sequence" refers to a second nucleotide sequence present in a vector of the invention. The term "heterologous sequence" also refers to any amino acid or RNA sequence encoded by a heterologous DNA sequence contained in a vector of the invention. Heterologous nucleotide sequences can encode proteins or RNA molecules normally expressed in the cell type in which they are present or molecules not normally expressed therein (e.g., Sindbis structural proteins).

Isolated: As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

Immunotherapeutic: As used herein, the term "immunotherapeutic" is a composition for the treatment of diseases or disorders. More specifically, the term is used to refer to a method of treatment for allergies or a method of treatment for cancer.

Individual: As used herein, the term "individual" refers to multicellular organisms and includes both plants and animals. Preferred multicellular organisms are animals, more preferred are vertebrates, even more preferred are mammals, and most preferred are humans.

Low or undetectable: As used herein, the phrase "low or undetectable," when used in reference to gene expression level, refers to a level of expression which is either significantly lower than that seen when the gene is maximally induced (e.g., at least five fold lower) or is not readily detectable by the methods used in the following examples section.

Lectin: As used herein, proteins obtained particularly from the seeds of leguminous plants, but also from many other plant and animal sources, that have binding sites for specific mono- or oligosaccharides. Examples include concanavalin A and wheat-germ agglutinin, which are widely used as analytical and preparative agents in the study of glycoproteins.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Non-natural molecular scaffold: As used herein, the phrase "non-natural molecular scaffold" refers to any product made by the hand of man that may serve to provide a rigid and repetitive array of first attachment sites. Ideally but not necessarily, these first attachment sites are in a geometric order. The non-natural molecular scaffold may be organic or non-organic and may be synthesized chemically or through a biological process, in part or in whole. The non-natural molecular scaffold is comprised of: (a) a core particle, either of natural or non-natural origin; and (b) an organizer, which itself comprises at least one first attachment site and is connected to a core particle by at least one covalent bond. In a particular embodiment, the non-natural molecular scaffold may be a virus, virus-like particle, a virus capsid particle, a phage, a recombinant form thereof, or synthetic particle.

Ordered and repetitive antigen or antigenic determinant array: As used herein, the term "ordered and repetitive antigen or antigenic determinant array" generally refers to a repeating pattern of antigen or antigenic determinant, characterized by a uniform spacial arrangement of the antigens or antigenic determinants with respect to the scaffold. In one embodiment of the invention, the repeating pattern may be a geometric pattern. An ideal ordered and repetitive antigen or antigenic determinant array will possess a strictly repetitive paracrystalline order of antigen or antigenic determinant with a spacing of 5 to 15 nanometers.

Organizer: As used herein, the term "organizer" is used to refer to an element bound to a core particle in a non-random fashion that provides a nucleation site for creating an ordered and repetitive antigen array. An organizer is any element comprising at least one first attachment site that is bound to a core particle by at least one covalent bond. An organizer may be a protein, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof.

Permissive temperature: As used herein, the phrase "permissive temperature" refers to temperatures at which an enzyme has relatively high levels of catalytic activity.

Purified: As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules.

Receptor: As used herein, the term "receptor" refers to proteins or glycoproteins or fragments thereof capable of interacting with another molecule, called the ligand. The ligand may belong to any class of biochemical or chemical compounds. The receptor need not necessarily be a membrane-bound protein. Soluble protein, like e.g. maltose binding protein or retinol binding protein are receptors as well.

Residue. As used herein, the term "residue" is meant to mean a specific amino acid in a polypeptide backbone or side chain.

Temperature-sensitive: As used herein, the phrase "temperature-sensitive" refers to an enzyme which readily catalyzes a reaction at one temperature but catalyzes the same reaction slowly or not at all at another temperature. An example of a temperature-sensitive enzyme is the replicase protein encoded by the pCYTts vector, which has readily detectable replicase activity at temperatures below 34° C. and has low or undetectable activity at 37° C.

Transcription: As used herein, the term "transcription" refers to the production of RNA molecules from DNA templates catalyzed by RNA polymerases.

Recombinant host cell: As used herein, the term "recombinant host cell" refers to a host cell into which one ore more nucleic acid molecules of the invention have been introduced.

Recombinant virus: As used herein, the phrase "recombinant virus" refers to a virus that is genetically modified by the hand of man. The phrase covers any virus known in the art. More specifically, the phrase refers to a an alphavirus genetically modified by the hand of man, and most specifically, the phrase refers to a Sinbis virus genetically modified by the hand of man.

Restrictive temperature: As used herein, the phrase "restrictive temperature" refers to temperatures at which an enzyme has low or undetectable levels of catalytic activity. Both "hot" and "cold" sensitive mutants are known and, thus, a restrictive temperature may be higher or lower than a permissive temperature.

RNA-dependent RNA replication event: As used herein, the phrase "RNA-dependent RNA replication event" refers to processes which result in the formation of an RNA molecule using an RNA molecule as a template.

RNA-Dependent RNA polymerase: As used herein, the phrase "RNA-Dependent RNA polymerase" refers to a polymerase which catalyzes the production of an RNA molecule from another RNA molecule. This term is used herein synonymously with the term "replicase."

Untranslated RNA: As used herein, the phrase "untranslated RNA" refers to an RNA sequence or molecule which does not encode an open reading frame or encodes an open reading frame, or portion thereof, but in a format in which an amino acid sequence will not be produced (e.g., no initiation codon is present). Examples of such molecules are tRNA molecules, rRNA molecules, and ribozymes.

Vector: As used herein, the term "vector" refers to an agent (e.g., a plasmid or virus) used to transmit genetic material to a host cell. A vector may be composed of either DNA or RNA.

one, a, or an: When the terms "one," "a," or "an" are used in this disclosure, they mean "at least one" or "one or more," unless otherwise indicated.

2. Compositions of Ordered and Repetitive Antigen or Antigenic Determinant Arrays and Methods to Make the Same The disclosed invention provides compositions comprising an ordered and repetitive antigen or antigenic determinant. Furthermore, the invention conveniently enables the practitioner to construct ordered and repetitive antigen or antigenic determinant arrays for various treatment purposes, which includes the prevention of infectious diseases, the treatment of allergies and the treatment of cancers.

Compositions of the invention essentially comprise two elements: (1) a non-natural molecular scaffold; and (2) an antigen or antigenic determinant with at least one second attachment site capable of association through at least one non-peptide bond to said first attachment site.

The non-natural molecular scaffold comprises (a) a core particle selected from the group consisting of (1) a core particle of non-natural origin and (2) a core particle of natural origin; and (b) an organizer comprising at least one first attachment site, wherein said organizer is connected to said core particle by at least one covalent bond.

The antigen or antigenic determinant has at least one second attachment site which is selected from the group consisting of (a) an attachment site not naturally occurring with said antigen or antigenic determinant; and (b) an attachment site naturally occurring with said antigen or antigenic determinant.

The invention provides for an ordered and repetitive antigen array through an association of the second attachment site to the first attachment site by way of at least one non-peptide bond. Thus, the antigen or antigenic determinant and the non-natural molecular scaffold are brought together through this association of the first and the second attachment site to form an ordered and repetitive antigen array.

The practioner may specifically design the antigen or antigenic determinant and the second attachment site such that the arrangement of all the antigens or antigenic determinants bound to the non-natural molecular scaffold will be uniform. For example, one may place a single second attachment site on the antigen or antigenic determinant at the carboxyl or amino terminus, thereby ensuring through design that all antigen or antigenic determinant molecules that are attached to the non-natural molecular scaffold are positioned in a uniform way. Thus, the invention provides a convenient means of placing any antigen or antigenic determinant onto a non-natural molecular scaffold in a defined order and repetition.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and may be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, $2^{nd}$ edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," *Meth. Enzymol.* 128, Academic Press San Diego (1990); Scopes, R. K., "Protein Purification Principles and Practice," $3^{rd}$ ed., Springer-Verlag, New York (1994)) are also adequately described in the literature, all of which are incorporated herein by reference.

A. Construction of a Non-natural Molecular Scaffold

One element in the composition of the invention is a non-natural, molecular scaffold comprising a core particle and an organizer. As used herein, the phrase "non-natural molecular scaffold" refers to any product made by the hand of man that may serve to provide a rigid and repetitive array of first attachment sites. More specifically, the non-natural molecular scaffold comprises (a) a core particle selected from the group consisting of (1) a core particle of non-natural origin and (2) a core particle of natural origin; and (b) an organizer comprising at least one first attachment site, wherein said organizer is connected to said core particle by at least one covalent bond.

As will be readily apparent to those skilled in the art, the core particle of the non-natural molecular scaffold of the invention is not limited to any specific form. The core particle may be organic or non-organic and may be synthesized chemically or through a biological process.

In one embodiment, a non-natural core particle may be a synthetic polymer, a lipid micelle or a metal. Such core particles are known in the art, providing a basis from which to build the novel non-natural molecular scaffold of the invention. By way of example, synthetic polymer or metal core particles are described in U.S. Pat. No. 5,770,380, which discloses the use of a calixarene organic scaffold to which is attached a plurality of peptide loops in the creation of an 'antibody mimic', and U.S. Pat. No. 5,334,394 describes nanocrystalline particles used as a viral decoy that are composed of a wide variety of inorganic materials, including metals or ceramics. Preferred metals in this embodiment include chromium, rubidium, iron, zinc, selenium, nickel, gold, silver, platinum. Preferred ceramic materials in this embodiment include silicon dioxide, titanium dioxide, aluminum oxide, ruthenium oxide and tin oxide. The core particles of this embodiment may be made from organic materials including carbon (diamond). Preferred polymers include polystyrene, nylon and nitrocellulose. For this type of nanocrystalline particle, particles made from tin oxide, titanium dioxide or carbon (diamond) are particularly preferred. A lipid micelle may be prepared by any means known in the art. For example micelles may be prepared according to the procedure of Baiselle and Millar (Baiselle, C. J. and Millar, D. B., Biophys. Chem. 4:355–361 (1975)) or Corti et al. (Corti, M., Degriorgio, V., Sonnino, S., Ghidoni R., Masserini, M. and Tettamanti, G., Chem. Phys. Lipids 38: 197–214 (1981)) or Lopez et al. (Lopez, O. de la Maza, A., Coderch, L., Lopez-Iglesias, C., Wehrli, E. and Parra, J. L., FEBS Lett. 426: 314–318 (1998)) or Topchieva and Karezin (Topchieva, I. and Karaezin, K., J. Colloid Interface Sci. 213: 29–35 (1999)) or Morein et al., (Morein, B., Sundquist, B., Hoglund, S., Dalsgaard K. and Osterhaus, A., Nature 308: 457–60 (1984)), which are all incorporated herein by reference.

The core particle may also be produced through a biological process, which may be natural or non-natural. By way of example, this type of embodiment may includes a core particle comprising a virus, virus-like particle, a phage, a viral capsid particle or a recombinant form thereof. In a more specific embodiment, the core particle may comprise recombinant proteins of Rotavirus, recombinant proteins of Norwalkvirus, recombinant proteins of Alphavirus, recombinant proteins of Foot and Mouth Disease virus, recombinant proteins of Retrovirus, recombinant proteins of Hepatitis B virus, recombinant proteins of Tobacco mosaic virus, recombinant proteins of Flock House Virus, and recombinant proteins of human Papilomavirus.

Whether natural or non-natural, the core particle of the invention is characterized by comprising organizer that is attached to the natural or non-natural core particle by at least one covalent bond. The organizer is an element bound to a core particle in a non-random fashion that provides a nucleation site for creating an ordered and repetitive antigen array. Ideally, but not necessarily, the organizer is associated with the core particle in a geometric order. Minimally, the organizer comprises a first attachment site.

As previously stated, the organizer may be any element comprising at least one first attachment site that is bound to a core particle by at least one covalent bond. An organizer may be a protein, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. In a more specific embodiment, the organizer may comprise a first attachment site comprising an antigen, an antibody or antibody fragment, biotin, avidin, strepavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfhydryl group, a chemical group reactive to a sulfhydryl group, or a combination thereof.

In a preferred embodiment, the core particle of the non-natural molecular scaffold comprises a virus, a bacteriophage, a virus-like particle, a viral capsid particle or a recombinant form thereof. Any virus known in the art having an ordered and repetitive coat and/or core protein structure may be selected as a non-natural molecular scaffold of the invention; examples of suitable viruses include: sindbis and other alphaviruses; vesicular somatitis virus; rhabdo-, (e.g. vesicular stomatitis virus), picorna-, toga-, orthomyxo-, polyoma-, parvovirus, rotavirus, norwalkvirus, foot and mouth disease virus, a retrovirus, hepatitis B virus, tobacco mosaic virus, flock house virus, human papilomavirus (for example, see Table 1 in Bachman, M. F. and Zinkemagel, R. M., *Immunol. Today* 17:553–558 (1996)).

In one embodiment, the invention utilizes genetic engineering of a virus to create a fusion between an ordered and repetitive viral envelope protein and an organizer comprising a heterologous protein, peptide, antigenic determinant or a reactive amino acid residue of choice. Other genetic manipulations known to those in the art may be included in the construction of the non-natural molecular scaffold; for example, it may be desirable to restrict the replication ability of the recombinant virus through genetic mutation. The viral protein selected for fusion to the organizer (i.e., first attachment site) protein should have an organized and repetitive structure, more preferably a paracrystalline organization optimally with a spacing of 5–15 nm on the surface of the virus. The creation of this type of fusion protein will result in multiple, ordered and repetitive organizers on the surface of the virus. Thus, the ordered and repetitive organization of the first attachment sites resulting therefrom will reflect the normal organization of the native viral protein.

As will be discussed in more detail herein, in a preferred embodiment of the invention, the scaffold is a recombinant alphavirus, and more specifically, a recombinant Sinbis virus. Alphaviruses are positive stranded RNA viruses that replicate their genomic RNA entirely in the cytoplasm of the infected cell and without a DNA intermediate (Strauss, J. and Strauss, E., *Microbiol. Rev.* 58:491–562 (1994)). Several members of the alphavirus family, Sindbis (Xiong, C. et al., *Science* 243:1188–1191 (1989); Schlesinger, S., *Trends Biotechnol.* 11:18–22 (1993)), Semliki Forest Virus (SFV) (Liljeström, P. & Garoff, H., *Bio/Technology* 9:1356–1361 (1991)) and others (Davis, N. L. et al., *Virology* 171: 189–204 (1989)), have received considerable attention for use as virus-based expression vectors for a variety of different proteins (Lundstrom, K., *Curr. Opin. Biotechnol.* 8:578–582 (1997); Liljeström, P., *Curr. Opin. Biotechnol.* 5:495–500 (1994)) and as candidates for vaccine development. Recently, a number of patents have issued directed to the use of alphaviruses for the expression of heterologous proteins and the development of vaccines (see U.S. Pat. Nos. 5,766,602; 5,792,462; 5,739,026; 5;789,245 and 5,814,482). The construction of the alphaviral scaffold of the invention may be done by means generally known in the art of recombinant DNA technology, as described by the aforementioned articles, which are incorporated herein by reference.

A variety of different recombinant host cells can be utilized to produce a viral-based core particle for antigen or antigenic determinant attachment. For example, Alphaviruses are known to have a wide host range; Sindbis virus infects cultured mammalian, reptilian, and amphibian cells, as well as some insect cells (Clark, H., *J. Natl. Cancer Inst.* 51:645 (1973); Leake, C., *J. Gen. Virol.* 35:335 (1977); Stollar, V. in THE TOGAVIRUSES, R. W. Schlesinger, Ed., Academic Press, (1980), pp. 583–621). Thus, numerous recombinant host cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 4:476 (1995); Lee K. et al. *Biotech. Bioeng.* 50:336 (1996)) to grow in serum-free medium, as well as in suspension.

Introduction of the polynucleotide vectors into host cells can be effected by methods described in standard laboratory manuals (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989), Chapter 9; Ausubel, F. et al., eds., CURRENT PROTOCOLS IN MOLECULAR BIOLOGY, John H. Wiley & Sons, Inc. (1997), Chapter 16), including methods such as electroporation, DEAE-dextran mediated transfection, transfection, microinjection, cationic lipid-mediated transfection, transduction, scrape loading, ballistic introduction, and infection. Methods for the introduction of exogenous DNA sequences into host cells are discussed in Felgner, P. et al., U.S. Pat. No. 5,580,859.

Packaged RNA sequences can also be used to infect host cells. These packaged RNA sequences can be introduced to host cells by adding them to the culture medium. For example, the preparation of non-infective alpahviral particles is described in a number of sources, including "Sindbis Expression System", Version C, (Invitrogen Catalog No. K750-1).

When mammalian cells are used as recombinant host cells for the production of viral-based core particles, these cells will generally be grown in tissue culture. Methods for growing cells in culture are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

As will be understood by those in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant of choice to the scaffold. In one embodiment, the attachment site is a protein or peptide that may be selected from those known in the art. For example, the first attachment site may selected from the following group: a ligand, a receptor, a lectin, avidin, streptavidin, biotin, an epitope such as an HA or T7 tag, Myc, Max, immunoglobulin domains and any other amino acid sequence known in the art that would be useful as a first attachment site.

It should be further understood by those in the art that with another embodiment of the invention, the first attachment site may be created secondarily to the organizer (i.e., protein or polypeptide) utilized in constructing the in-frame fusion to the capsid protein. For example, a protein may be utilized for fusion to the envelope protein with an amino acid sequence known to be glycosylated in a specific fashion, and the sugar moiety added as a result may then serve at the first attachment site of the viral scaffold by way of binding to a lectin serving as the secondary attachment site of an antigen. Alternatively, the organizer sequence may be biotinylated in vivo and the biotin moiety may serve as the first attachment site of the invention, or the organizer sequence may be subjected to chemical modification of distinct amino acid residues in vitro, the modification serving as the first attachment site.

One specific embodiment of the invention utilizes the Sinbis virus. The Sinbis virus RNA genome is packaged into a capsid protein that is surrounded by a lipid bilayer containing three proteins called E1, E2, and E3. These so-called envelope proteins are glycoproteins, and the glycosylated portions are located on the outside of the lipid bilayer, where complexes of these proteins form the "spikes" that can be seen in electron micrographs to project outward from the surface of the virus. In a preferred embodiment of the invention, the first attachment site is selected to be the JUN or FOS leucine zipper protein domain that is fused in frame to the E2 envelope protein. However, it will be clear to all individuals in the art that other envelope proteins may be utilized in the fusion protein construct for locating the first attachment site in the scaffold of the invention.

In a most preferred embodiment of the invention, the first attachment site is selected to be the JUN-FOS leucine zipper protein domain that is fused in frame to the Hepatitis B capsid (core) protein. However, it will be clear to all individuals in the art that other viral capsid proteins may be utilized in the fusion protein construct for locating the first attachment site in the scaffold of the invention.

In another preferred embodiment of the invention, the first attachment site is selected to be a lysine or cysteine residue that is fused in frame to the Hepatitis core (capsid) protein. However, it will be clear to all individuals in the art that other viral capsid or virus-like particles may be utilized in the fusion protein construct for locating the first attachment in the scaffold of the invention.

Example 1 is provided to demonstrate the construction of an in-frame fusion protein between the Sinbis virus E2 envelope protein and the JUN leucine zipper protein domain using the pTE5'2J vector of Hahn et al. (*Proc. Natl. Acad. Sci. USA* 89:2679–2683 (1992)). The JUN amino acid sequence utilized for the first attachment site is the following:

(SEQ ID NO:59)
CGGRIARLEEKVKTLKAQNSELASTANMLREQVAQLKQKVMNHVGC

In this instance, the anticipated second attachment site on the antigen would be the FOS leucine zipper protein domain and the amino acid sequence would be the following:

(SEQ ID NO:60)
CGGLTDTLQAETDQVEDEKSALQTEIANLLKEKEKLEFILAAHGGC

These sequences are derived from the transcription factors JUN and FOS, each flanked with a short sequence containing a cysteine residue on both sides. These sequences are known to interact with each other. The original hypothetical structure proposed for the JUN-FOS dimer assumed that the hydrophobic side chains of one monomer interdigitate with the respective side chains of the other monomer in a zipper-like manner (Landschulz et al., *Science* 240:1759–1764 (1988)). However, this hypothesis proved to be wrong, and these proteins are known to form an a-helical coiled coil (O'Shea et al., *Science* 243:538–542 (1989); O'Shea et al., *Cell* 68:699–708 (1992); Cohen & Parry, *Trends Biochem. Sci.* 11:245–248 (1986)), Thus, the term "leucine zipper" is frequently used to refer to these protein domains for more historical than structural reasons. Throughout this patent, the term "leucine zipper" is used to refer to the sequences depicted above or sequences essentially similar to the ones depicted above. The terms JUN and FOS are used for the respective leucine zipper domains rather than the entire JUN and FOS proteins.

In one embodiment, the invention provides for the production of a Sinbis virus E2-JUN scaffold using the pCYTts expression system (U.S. Patent Application Appl. No. 60/079,562; Filed Mar. 27, 1998). The pCYTts expression system provides novel expression vectors which permit tight regulation of gene expression in eucaryotic cells. The DNA vectors of this system are transcribed to form RNA molecules which are then replicated by a temperature-sensitive replicase to form additional RNA molecules. The RNA molecules produced by replication contain a nucleotide sequence which may be translated to produce a protein of interest or which encode one or more untranslated RNA molecules. Thus the expression system enables the production of recombinant Sinbis virus particles.

Example 2 provides details on the production of the E2-JUN Sinbis non-natural, molecular scaffold of the invention. Additionally provided in Example 3 is another method for the production of recombinant E2-JUN Sinbis virus scaffold using the pTE5'2JE2:JUN vector produced in Example 1. Thus the invention provides two means, the pCYTts expression system (Example 2) and the pTE5'2J vector system (Example 3) by which recombinant Sinbis virus E2-JUN non-natural, molecular scaffold may be produced. An analysis of viral particles produced in each system is proved in FIG. 1 and FIG. 2.

As previously stated, the invention includes viral-based core particles which comprise a virus, virus-like particle, a phage, a viral capsid particle or a recombinant form thereof. Skilled artisans have the knowledge to produce such core particles and attach organizers thereto. By way of providing other examples, the invention provides herein for the production of hepatitis B virus-like particles and measles viral capsid particles as core particles (Examples 17 to 22). In such an embodiment, the JUN leucine zipper protein domain or FOS leucine zipper protein domain may be used as an organizer, and hence as a first attachment site, for the non-natural molecular scaffold of the invention.

Examples 23–29 provide details of the production of Hepatitis B core particles carrying an in-frame fused peptide with a reactive lysine residue and antigens carrying a genetically fused cysteine residue, as first and second attachment site, respectively.

B. Construction of an Antigen or Antigenic Determinant with a Second Attachment Site The second element in the composition of the invention is an antigen or antigenic determinant possessing at least one second attachment site capable of association through at least one non-peptide bond to the first attachment site of the non-natural molecular scaffold. The invention provides for compositions that vary according to the antigen or antigenic determinant selected in consideration of the desired therapeutic effect. Other compositions are provided by varying the molecule selected for the second attachment site.

Antigens of the invention may be selected from the group consisting of the following: (a) proteins suited to induce an immune response against cancer cells; (b) proteins suited to induce an immune response against infectious diseases; (c) proteins suited to induce an immune response against allergens, and (d) proteins suited to induce an immune response in farm animals.

In one specific embodiment of the invention, the antigen or antigenic determinant is one that is useful for the prevention of infectious disease. Such treatment will be useful to treat a wide variety of infectious diseases affecting a wide range of hosts, e.g., human, cow, sheep, pig, dog, cat, other mammalian species and non-mammalian species as well. Treatable infectious diseases are well known to those skilled in the art, examples include infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc. Thus, antigens or antigenic determinants selected for the compositions of the invention will be well known to those in the medical art; examples of antigens or antigenic determinants include the following: the HIV antigens gp140 and gp160; the influenaza antigens hemagglutinin and neuraminidase, hepatitis B surface antigen, circumsporozoite protein of malaria.

In another specific embodiment, the compositions of the invention are an immunotherapeutic that may be used for the treatment of allergies or cancer.

The selection of antigens or antigenic determinants for the composition and method of treatment for allergies would be known to those skilled in the medical art treating such disorders; representative examples of this type of antigen or antigenic determinant include the following: bee venom phospholipase $A_2$, Bet v I (birch pollen allergen), 5 Dol m V (white-faced hornet venom allergen), Der p I (House dust mite allergen).

The selection of antigens or antigenic determinants for the composition and method of treatment for cancer would be known to those skilled in the medical art treating such disorders; representative examples of this type of antigen or antigenic determinant include the following: Her2 (breast cancer), GD2 (neuroblastoma), EGF-R (malignant glioblastoma), CEA (medullary thyroid cancer), CD52 (leukemia).

In a particular embodiment of the invention, the antigen or antigenic determinant is selected from the group consisting of: (a) a recombinant protein of HIV, (b) a recombinant protein of Influenza virus, (c) a recombinant protein of Hepatitis C virus, (d) a recombinant protein of Toxoplasma, (e) a recombinant protein of Plasmodium falciparum, (f) a recombinant protein of Plasmodium vivax, (g) a recombinant protein of Plasmodium ovale, (h) a recombinant protein of Plasmodium malariae, (i) a recombinant protein of breast cancer cells, (j) a recombinant protein of kidney cancer cells, (k) a recombinant protein of prostate cancer cells, (l) a recombinant protein of skin cancer cells, (m) a recombinant protein of brain cancer cells, (n) a recombinant protein of leukemia cells, (o) a recombinant profiling, (p) a recombinant protein of bee sting allergy, (q) a recombinant proteins of nut allergy, (r) a recombinant proteins of food allergies, recombinant proteins of asthma, and a recombinant protein of Chlamydia.

Once the antigen or antigenic determinant of the composition is chosen, at least one second attachment site may be added to the molecule in preparing to construct the organized and repetitive array associated with the non-natural molecular scaffold of the invention. Knowledge of what will constitute an appropriate second attachment site will be known to those skilled in the art. Representative examples of second attachment sites include, but are not limited to, the following: an antigen, an antibody or antibody fragment, biotin, avidin, strepavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfhydryl group, a chemical group reactive to a sulfhydryl group, or a combination thereof.

The association between the first and second attachment sites will be determined by the characteristics of the respective molecules selected but will comprise at least one non-peptide bond. Depending upon the combination of first and second attachment sites, the nature of the association may be covalent, ionic, hydrophobic, polar, or a combination thereof.

In one embodiment of the invention, the second attachment site may be the FOS leucine zipper protein domain or the JUN leucine zipper protein domain.

In a most specific embodiment of the invention, the second attachment site selected is the FOS leucine zipper protein domain, which associates specifically with the JUN leucine zipper protein domain of the non-natural molecular scaffold of the invention. The association of the JUN and FOS leucine zipper protein domains provides a basis for the formation of an organized and repetitive antigen or antigenic determinant array on the surface of the scaffold. The FOS leucine zipper protein domain may be fused in frame to the antigen or antigenic determinant of choice at either the amino terminus, carboxyl terminus or internally located in the protein if desired.

Several FOS fusion constructs are provided for exemplary purposes. Human growth hormone (Example 4), bee venom phospholipase $A_2$ (PLA) (Example 9), ovalbumin (Example 10) and HIV gp140 (Example 12).

In order to simplify the generation of FOS fusion constructs, several vectors are disclosed that provide options for antigen or antigenic determinant design and construction (see Example 6). The vectors pAV1–4 were designed for the expression of FOS fusion in *E. coli*; the vectors pAV5 and pAV6 were designed for the expression of FOS fusion proteins in eukaryotic cells. Properties of these vectors are briefly described:

1. pAV1: This vector was designed for the secretion of fusion proteins with FOS at the C-terminus into the *E. coli* periplasmic space. The gene of interest (g.o.i.) may be ligated into the StuI/NotI sites of the vector.

2. pAV2: This vector was designed for the secretion of fusion proteins with FOS at the N-terminus into the *E. coli* periplasmic space. The gene of interest (g.o.i.) ligated into the NotI/EcoRV (or NotI/HindIII) sites of the vector.

3. pAV3: This vector was designed for the cytoplasmic production of fusion proteins with FOS at the C-terminus in *E. coli*. The gene of interest (g.o.i.) may be ligated into the EcoRV/NotI sites of the vector.

4. pAV4: This vector is designed for the cytoplasmic production of fusion proteins with FOS at the N-terminus in *E. coli*. The gene of interest (g.o.i.) may be ligated into the NotI/EcoRV (or NotI/HindIII) sites of the vector. The N-terminal methionine residue is proteolytically removed upon protein synthesis (Hirel et al., *Proc. Natl. Acad. Sci. USA* 86:8247–8251 (1989)).

5. pAV5: This vector was designed for the eukaryotic production of fusion proteins with FOS at the C-terminus. The gene of interest (g.o.i.) may be inserted between the sequences coding for the hGH signal sequence and the FOS domain by ligation into the Eco47III/NotI sites of the vector. Alternatively, a gene containing its own signal sequence may be fused to the FOS coding region by ligation into the StuI/NotI sites.

6. pAV6: This vector was designed for the eukaryotic production of fusion proteins with FOS at the N-terminus. The gene of interest (g.o.i.) may be ligated into the NotI/StuI (or NotI/HindIII) sites of the vector.

As will be understood by those skilled in the art, the construction of a FOS-antigen or -antigenic determinant fusion protein may include the addition of certain genetic elements to facilitate production of the recombinant protein. Example 4 provides guidance for the addition of certain *E. coli* regulatory elements for translation, and Example 7 provides guidance for the addition of a eukaryotic signal sequence. Other genetic elements may be selected, depending on the specific needs of the practioner.

The invention is also seen to include the production of the FOS-antigen or FOS-antigenic determinant fusion protein either in bacterial (Example 5) or eukaryotic cells (Example 8). The choice of which cell type in which to express the fusion protein is within the knowledge of the skilled artisan, depending on factors such as whether post-translational modifications are an important consideration in the design of the composition.

As noted previously, the invention discloses various methods for the construction of a FOS-antigen or FOS-antigenic determinant fusion protein through the use of the pAV vectors. In addition to enabling prokaryotic and eukaryotic expression, these vectors allow the practitioner to choose between - and C-terminal addition to the antigen of the FOS leucine zipper protein domain. Specific examples are provided wherein - and C-terminal FOS fusions are made to PLA (Example 9) and ovalbumin (Example 10). Example 11 demonstrates the purification of the PLA and ovalbumin FOS fusion proteins.

In a most specific embodiment, the invention is drawn to an antigen or antigenic determinant encoded by the HIV genome. More specifically, the HIV antigen is gp140. As provided for in Examples 11–15, HIV gp140 may be created with a FOS leucine zipper protein domain and the fusion protein synthesized and purified for attachment to the non-natural molecular scaffold of the invention. As one skilled in the art would know, other HIV antigens or antigenic determinants may be used in the creation of a composition of the invention.

In a most specific embodiment of the invention, the second attachment site selected is a cysteine residue, which associates specifically with a lysine residue of the non-natural molecular scaffold of the invention. The chemical linkage of the lysine residue (Lys) and cysteine residue (Cys) provides a basis for the formation of an organized and repetitive antigen or antigenic determinant array on the surface of the scaffold. The cysteine residue may be engineered in frame to the antigen or antigenic determinant of choice at either the amino terminus, carboxyl terminus or internally located in the protein if desired. By way of example, PLA and HIV gp140 are provided with a cysteine residue for linkage to a lysine residue first attachment site.

C. Preparation of the AlphaVaccine Particles

The invention provides novel compositions and methods for the construction of ordered and repetitive antigen arrays. As one of skill in the art would know, the conditions for the assembly of the ordered and repetitive antigen array depend to a large extent on the specific choice of the first attachment site of the non-natural scaffold and the specific choice of the second attachment site of the antigen or antigenic determinant. Thus, practitioner choice in the design of the composition (i.e., selection of the first and second attachment sites, antigen and non-natural scaffold) will determine the specific conditions for the assembly of the AlphaVaccine particle (the ordered and repetitive antigen array and non-natural molecular scaffold combined). Information relating to assembly of the AlphaVaccine particle is well within the working knowledge of the practitioner, and numerous references exist to aid the practitioner (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Celis, J., ed., CELL BIOLGY, Academic Press, $2^{nd}$ edition, (1998); Harlow, E. and Lane, D., "Antibodies: A Laboratory Manual," Cold Spring Harbor Laboratory, Cold Spring Harbor, N.Y. (1988), all of which are incorporated herein by reference.

In a specific embodiment of the invention, the JUN and FOS leucine zipper protein domains are utilized for the first and second attachment sites of the invention, respectively. In the preparation of AlphaVaccine particles, antigen must be produced and purified under conditions to promote assembly of the ordered and repetitive antigen array onto the non-natural scaffold. In the particular JUN/FOS leucine zipper protein domain embodiment, the FOS-antigen or FOS-antigenic determinant should be treated with a reducing agent (e.g., Dithiothreitol (DTT)) to reduce or eliminate the incidence of disulfide bond formation (Example 15).

For the preparation of the non-natural scaffold (i.e., recombinant Sinbis virus) of the JUN/FOS leucine zipper protein domain embodiment, recombinant E2-JUN viral particles should be concentrated, neutralized and treated with reducing agent (see Example 16).

Assembly of the ordered and repetitive antigen array in the JUN/FOS embodiment is done in the presence of a redox shuffle. E2-JUN viral particles are combined with a 240 fold molar excess of FOS-antigen or FOS-antigenic determinant for 10 hours at 4° C. Subsequently, the AlphaVaccine particle is concentrated and purified by chromatography (Example 16).

In another embodiment of the invention, the coupling of the non-natural molecular scaffold to the antigen or antigenic determinant may be accomplished by chemical crosslinking. In a most preferred embodiment, the chemical agent is a hetero-bifunctional crosslinking agent such as ε-maleimidocaproic acid N-hydroxysuccinimide ester (Tanimori et al., *J. Pharm. Dyn.* 4:812 (1981); Fujiwara et al., *J. Immunol. Meth.* 45:195 (1981), which contains (1) a succinimide group reactive with amino groups and (2) a maleimide group reactive with SH groups. A heterologous protein or polypeptide of the first attachment site may be engineered to contain one or more lysine residues that will serve as a reactive moiety for the succinimide portion of the hetero-bifunctional crosslinking agent. Once chemically coupled to the first attachment sites of the non-natural molecular scaffold, the maleimide group of the hetero-bifunctional crosslinking agent will be available to react with the SH group of a cysteine residue on the antigen or antigenic determinant. Antigen or antigenic determinant preparation in this instance may require the engineering of a cysteine residue into the protein or polypeptide chosen as the second attachment site so that it may be reacted to the free maleimide function on the crosslinking agent bound to the non-natural molecular scaffold first attachment sites.

3. Compositions, Vaccines, and the Administration Thereof, and Methods of Treatment In one embodiment, the invention provides vaccines for the prevention of infectious diseases in a wide range of species, particularly mammalian species such as human, monkey, cow, dog, cat, horse, pig, etc. Vaccines may be designed to treat infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

In another embodiment, the invention provides vaccines for the prevention of cancer in a wide range of species, particularly mammalian species such as human, monkey, cow, dog, cat, horse, pig, etc. Vaccines may be designed to treat all types of cancer: lymphomas, carcinomas, sarcomas, melanomas, etc.

In another embodiment of the invention, the compositions of the invention may be used in the design of vaccines for the treatment of allergies. Antibodies of the IgE isotype are important components in allergic reactions. Mast cells bind IgE antibodies on their surface and release histamines and other mediators of allergic response upon binding of specific antigen to the IgE molecules bound on the mast cell surface. Inhibiting production of IgE antibodies, therefore, is a promising target to protect against allergies. This should be possible by attaining a desired T helper cell response. T helper cell responses can be divided into type 1 ($T_H1$) and type 2 ($T_H2$) T helper cell responses (Romagnani, *Immunol. Today* 18:263–266 (1997)). $T_H1$ cells secrete interferon-gamma and other cytokines which trigger B cells to produce IgG1–3 antibodies. In contrast, a critical cytokine produced by $T_H2$ cells is IL-4, which drived B cells to produce IgG4 and IgE. In many experimental systems, the development of $T_H1$ and $T_H2$ responses is mutually exclusive since $T_H1$ cells suppress the induction of $T_H2$ cells and vice versa. Thus, antigens that trigger a strong $T_H1$ response simultaneously suppress the development of $T_H2$ responses and hence the production of IgE antibodies. Interestingly, virtually all viruses induce a $T_H1$ response in the host and fail to trigger the production of IgE antibodies (Coutelier et al., *J. Exp. Med.* 165:64–69 (1987)). This isotype pattern is not restricted to live viruses but has also been observed for inactivated or recombinant viral particles (Lo-Man et al., *Eur. J. Immunol.* 28:1401–1407 (1998)). Thus, by using the processes of the invention (e.g., AlphaVaccine Technology), viral particles can be decorated with various allergens and used for immunization. Due to the resulting "viral structure" of the allergen, a $T_H1$ response will be elicited, "protective" IgG1–3 antibodies will be produced, and the production of IgE antibodies which cause allergic reactions will be prevented. Since the allergen is presented by viral particles which are recognized by a different set of helper T cells than the allergen itself, it is likely that the allergen-specific IgG1–3 antibodies will be induced even in allergic individuals harboring pre-existing $T_H2$ cells specific for the allergen. The presence of high concentrations of IgG antibodies may prevent binding of allergens to mast cell bound IgE, thereby inhibiting the release of histamine. Thus, presence of IgG antibodies may protect from IgE mediated allergic reactions. Typical substances causing allergies include: grass, ragweed, birch or mountain cedar pollens, house dust, mites, animal danders, mold, insect venom or drugs (e.g. penicillin). Thus, immunization of individuals with allergen-decorated viral particles should be beneficial not only before but also after the onset of allergies.

As would be understood by one of ordinary skill in the art, when the compositions of the invention are administered to an individual, they may be in a composition which contains salts, buffers, adjuvants, or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1980)).

The compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

In addition to vaccine technologies, other embodiments of the invention are drawn to methods of medical treatment for cancer and allergies.

All patents and publications referred to herein are expressly incorporated by reference.

EXAMPLES

Enzymes and reagents used in the experiments that follow included: T4 DNA ligase obtained from New England Biolabs; Taq DNA Polymerase, QIAprep Spin Plasmid Kit, QIAGEN Plasmid Midi Kit, QiaExII Gel Extraction Kit, QIAquick PCR Purification Kit obtained from QIAGEN; QuickPrep Micro mRNA Purification Kit obtained from Pharmacia; SuperScript One-step RT PCR Kit, fetal calf serum (FCS), bacto-tryptone and yeast extract obtained from Gibco BRL; Oligonucleotides obtained from Microsynth (Switzerland); restriction endonucleases obtained from Boehringer Mannheim, New England Biolabs or MBI Fermentas; Pwo polymerase and dNTPs obtained from Boehringer Mannheim. HP-1 medium was obtained from Cell culture technologies (Glattbrugg, Switzerland). All standard chemicals were obtained from Fluka-Sigma-Aldrich, and all cell culture materials were obtained from TPP.

DNA manipulations were carried out using standard techniques. DNA was prepared according to manufacturer instruction either from a 2 ml bacterial culture using the QIAprep Spin Plasmid Kit or from a 50 ml culture using the QIAGEN Plasmid Midi Kit. For restriction enzyme digestion, DNA was incubated at least 2 hours with the appropriate restriction enzyme at a concentration of 5–10 units (U) enzyme per mg DNA under manufacturer recommended conditions (buffer and temperature). Digests with more than one enzyme were performed simultaneously if reaction conditions were appropriate for all enzymes, otherwise consecutively. DNA fragments isolated for further manipulations were separated by electrophoresis in a 0.7 to 1.5% agarose gel, excised from the gel and purified with the QiaExII Gel Extraction Kit according to the instructions provided by the manufacturer. For ligation of DNA fragments, 100 to 200 pg of purified vector DNA were incubated overnight with a threefold molar excess of the insert fragment at 16° C. in the presence of 1 U T4 DNA ligase in the buffer provided by the manufacturer (total volume: 10–20

μl). An aliquot (0.1 to 0.5 μl) of the ligation reaction was used for transformation of *E. coli* XL1-Blue (Stratagene). Transformation was done by electroporation using a Gene Pulser (BioRAD) and 0.1 cm Gene Pulser Cuvettes (BioRAD) at 200 Ω, 25 μF, 1.7 kV. After electroporation, the cells were incubated with shaking for 1 h in 1 ml S.O.B. medium (Miller, 1972) before plating on selective S.O.B. agar.

Example 1

Insertion of the JUN Amphiphatic Helix Domain within E2

In the vector pTE5'2J (Hahn et al., *Proc. Natl. Acad. Sci. USA* 89:2679–2683, (1992)), MluI and a BstEII restriction enzyme sites were introduced between codons 71 (Gln) and 74 (Thr) of the structural protein E2 coding sequence, resulting in vector pTE5'2JBM. Introduction of these restriction enzymes sites was done by PCR using the following oligonucleotides:

```
Oligo 1:
E2insBstEII/BssHII:
5'-ggggACGCGTGCAGCAggtaaccaccgTTAAAGAAGGCACC-3'
(SEQ ID NO:1)
```

```
Oligo 2:
E2insMluIStuI:
5'-cggtggttaccTGCTGCACGCGTTGCTTAAGCGACATGTAGCGG-3'
(SEQ ID NO:2)
```

```
Oligo 3:
E2insStuI:
5'-CCATGAGGCCTACGATACCC-3'
(SEQ ID NO:3)
```

```
Oligo4:
E2insBssHII:
5'-GGCACTCACGGCGCGCTTTACAGGC-3'
(SEQ ID NO:4)
```

For the PCR reaction, 100 pmol of each oligo was used with 5 ng of the template DNA in a 100 μl reaction mixture containing 4 units of Taq or Pwo polymerase, 0.1 mM dNTPs and 1.5 mM MgSO$_4$. All DNA concentrations were determined photometrically using the GeneQuant apparatus (Pharmacia). Polymerase was added directly before starting the PCR reaction (starting point was 95° C.). Temperature cycling was done in the following manner and order: 95° C. for 2 minutes; 5 cycles of 95° C. (45 seconds), 53° C. (60 seconds), 72° C. (80 seconds); and 25 cycles of 95° C. (45 seconds), 57° C. (60 seconds), 72° C. (80 seconds).

The two PCR fragments were analyzed and purified by agarose gelelectrophoresis. Assembly PCR of the two PCR fragments using oligo 3 and 4 for amplification was carried out to obtain the final construct.

For the assembly PCR reaction, 100 pmol of each oligo was used with 2 ng of the purified PCR fragments in a 100 μl reaction mixture containing 4 units of Taq or Pwo polymerase, 0.1 mM dNTPs and 1.5 mM MgSO$_4$. All DNA concentrations were determined photometrically using the GeneQuant apparatus (Pharmacia). Polymerase was added directly before starting the PCR reaction (starting point was 95° C.). Temperature cycling was done in the following manner and order: 95° C. for 2 minutes; 5 cycles of 95° C. (45 seconds), 57° C. (60 seconds), 72° C. (90 seconds); and 25 cycles of 95° C. (45 seconds), 59° C. (60 seconds), 72° C. (90 seconds).

The final PCR product was purified using Qia spin PCR columns (Qiagen) and digested in an appropriate buffer using 10 units each of BssHII and StuI restriction endonucleases for 12 hours at 37° C. The DNA fragments were gel-purified and ligated into BssHII/StuI digested and gel-purified pTE5'2J vector (Hahn et al., *Proc. Natl. Acad. Sci. USA* 89:2679–2683). The correct insertion of the PCR product was first analyzed by BstEII and MluI restriction analysis and then by DNA sequencing of the PCR fragment.

The DNA sequence coding for the JUN amphiphatic helix domain was PCR-amplified from vector pJuFo (Crameri and Suter, *Gene* 137:69 (1993)) using the following oligonucleotides:

```
Oligo 5:
JUNBstEII:
5'-CCTTCTTTAAcggtggttaccTGCTGGCAACCAACGTGGTTCATGAC-3'   (SEQ ID NO:5)
```

```
Oligo 6:
MluIJUN:
5'-AAGCATGCTGCacgcgtgTGCGGTGGTCGGATCGCCCGGC-3'          (SEQ ID NO:6)
```

For the PCR reaction, 100 pmol of each oligo was used with 5 ng of the template DNA in a 100 μl reaction mixture containing 4 units of Taq or Pwo polymerase, 0.1 mM dNTPs and 1.5 mM MgSO$_4$. All DNA concentrations were determined photometrically using the GeneQuant apparatus (Pharmacia). Polymerase was added directly before starting the PCR reaction (starting point was 95° C.). Temperature cycling was done in the following order and manner: 95° C. for 2 minutes; 5 cycles of 95° C. (45 seconds), 60° C. (30 seconds), 72° C. (25 seconds); and 25 cycles of 95° C. (45 seconds), 68° C. (30 seconds), 72° C. (20 seconds).

The final PCR product was gel-purified and ligated into EcoRV digested and gel-purified pBluescript II(KS$^-$). From the resulting vector, the JUN sequence was isolated by cleavage with MluI/BstEII purified with QiaExII and ligated into vector pTE5'2JBM (previously cut with the same restriction enzymes) to obtain the vector pTE5'2J:E2JUN.

Example 2

Production of Viral Particles Containing E2-JUN Using the pCYTts System

The structural proteins were PCR amplified using pTE5'2J:E2JUN as template and the oligonucleotides XbaI-Struct (ctatcaTCTAGAATGAATA GAGGATTCTTTAAC) (SEQ ID NO: 12) and StructBsp1201 (tcgaatGGGCC CTCATCTTCGTGTGCTAGTCAG) (SEQ ID NO: 87). For the PCR 100 pmol of each loligo was used and 5 ng of the template DNA was used in the 100 μl reaction mixture, containing 4 units of Tac or Pwo polymerase, 0.1 mM dNTPs and 1.5 mM MgSO$_4$. All DNA concentrations were determined photometrically using the GeneQuant apparatus (Pharmacia). The polymerase was added directly before starting the PCR reaction (starting point was 95° C.). The temperature cycles were as follows: 95° C. for 3 minutes, followed by 5 cycles of 92° C. (30 seconds), 54° C. (35 seconds), 72° C. (270 seconds) and followed by 25 cycles of 92° C. (30 seconds), 63° C. (35 seconds), 72° C. (270 seconds. The PCR product was gel purified and digested with the restriction enzymes XbaI/Bsp120I and ligated into vector pCYTts previously cleaved with the same enzymes (U.S. Patent Application Appl. No. 60/079,562; Filed Mar. 27, 1998)

Twenty µg of pCYTtsE2:JUN were incubated with 30 U of ScaI in an appropriate buffer for at least 4 hours at 37° C. The reaction was stopped by phenol/chloroform extraction, followed by an isopropanol precipitation of the linerized DNA. The restriction reaction was checked by agarose gel eletrophoresis. For the transfection, 5.4 µg of linearized pCYTtsE2:JUN was mixed with 0.6 µg of linearized pSV2Neo in 30 µl H$_2$O and 30 µl of 1 M CaCl$_2$ solution were added. After addition of 60 µl phosphate buffer (50 mM HEPES, 280 mM NaCl, 1.5 mM Na$_2$ HPO$_4$, pH 7.05), the solution was vortexed for 5 seconds, followed by an incubation at room temperature for 25 seconds. The solution was immediately added to 2 ml HP-1 medium containing 2% FCS (2% FCS medium). The medium of an 80% confluent BHK21 cell culture in a 6-well plate was then replaced with the DNA containing medium. After an incubation for 5 hours at 37° C. in a CO$_2$ incubator, the DNA containing medium was removed and replaced by 2 ml of 15% glycerol in 2% FCS medium. The glycerol containing medium was removed after a 30 second incubation phase, and the cells were washed by rinsing with 5 ml of HP-1 medium containing 10% FCS. Finally 2 ml of fresh HP-1 medium containing 10% FCS was added.

Stably transfected cells were selected and grown in selection medium (HP-1 medium, supplemented with G418) at 37° C. in a CO$_2$ incubator. When the mixed population was grown to confluency, the culture was split to two dishes, followed by a 12 hours growth period at 37° C. One dish of the cells was shifted to 30° C. to induce the expression of the viral particles; the other dish was kept at 37° C.

The expression of viral particles was determined by Western blotting (FIG. 1). Culture medium (0.5 ml) was methanol/chloroform precipitated, and the pellet was resuspended in SDS-PAGE sample buffer. Samples were heated for 5 minutes at 95° C. before being applied to 15% acrylamide gel. After SDS-PAGE, proteins were transferred to Protan nitrocellulose membranes (Schleicher & Schuell, Germany) as described by Bass and Yang, in Creighton, T. E., ed., *Protein Function: A Practical Approach*, 2nd Edn., IRL Press, Oxford (1997), pp. 29–55. The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with an anti-E1/E2antibody (polyclonal serum) for 1 hour. The blot was washed 3 times for 10 minutes with TBS-T (TBS with 0.05% Tween20), and incubated for 1 hour with an alkaline-phosphatase-anti-rabbit IgG conjugate (0.1 µg/ml, Amersham Life-Science, England). After washing 2 times for 10 minutes with TBS-T and 2 times for 10 minutes with TBS, the development reaction was carried out using alkaline phosphatase detection reagents (10 ml AP buffer (100 mM Tris/HCl, 100 mM NaCl, pH 9.5) with 50 µl NBT solution (7.7% Nitro Blue Tetrazolium (Sigma) in 70% dimethylformamide) and 37 µl of X-Phosphate solution (5% of 5-bromo-4-chloro-3-indolyl phosphate in dimethylformamide).

The production of viral particles is shown in FIG. 1. The Western Blot pattern showed that E2-JUN (lane 1) migrated to a higher molecular weight in SDS-PAGE compared to wild type E2 (lane 2) and the BHK21 host cell line did not show any background.

Example 3

Production of Viral Particles Containing E2-JUN Using the pTE5'2JE2:JUN Vector

RNase-free vector (1.0 µg) was linearized by PvuI digestion. Subsequently, in vitro transcription was carried out using an SP6 in vitro transcription kit (InvitroscripCAP by InvitroGen, Invitrogen BV, NV Leek, Netherlands). The resulting 5'-capped mRNA was analyzed on a reducing agarose-gel.

In vitro transcribed mRNA (5 µg) was electroporated into BHK 21 cells (ATCC: CCL10) according to Invitrogen's manual (Sindbis Expression system, Invitrogen BV, Netherlands). After 10 hours incubation at 37° C., the FCS containing medium was exchanged by HP-1 medium without FCS, followed by an additional incubation at 37° C. for 10 hours. The supernatant was harvested and analyzed by Western blot analysis for production of viral particles exactly as described in Example 2.

Figure 2:
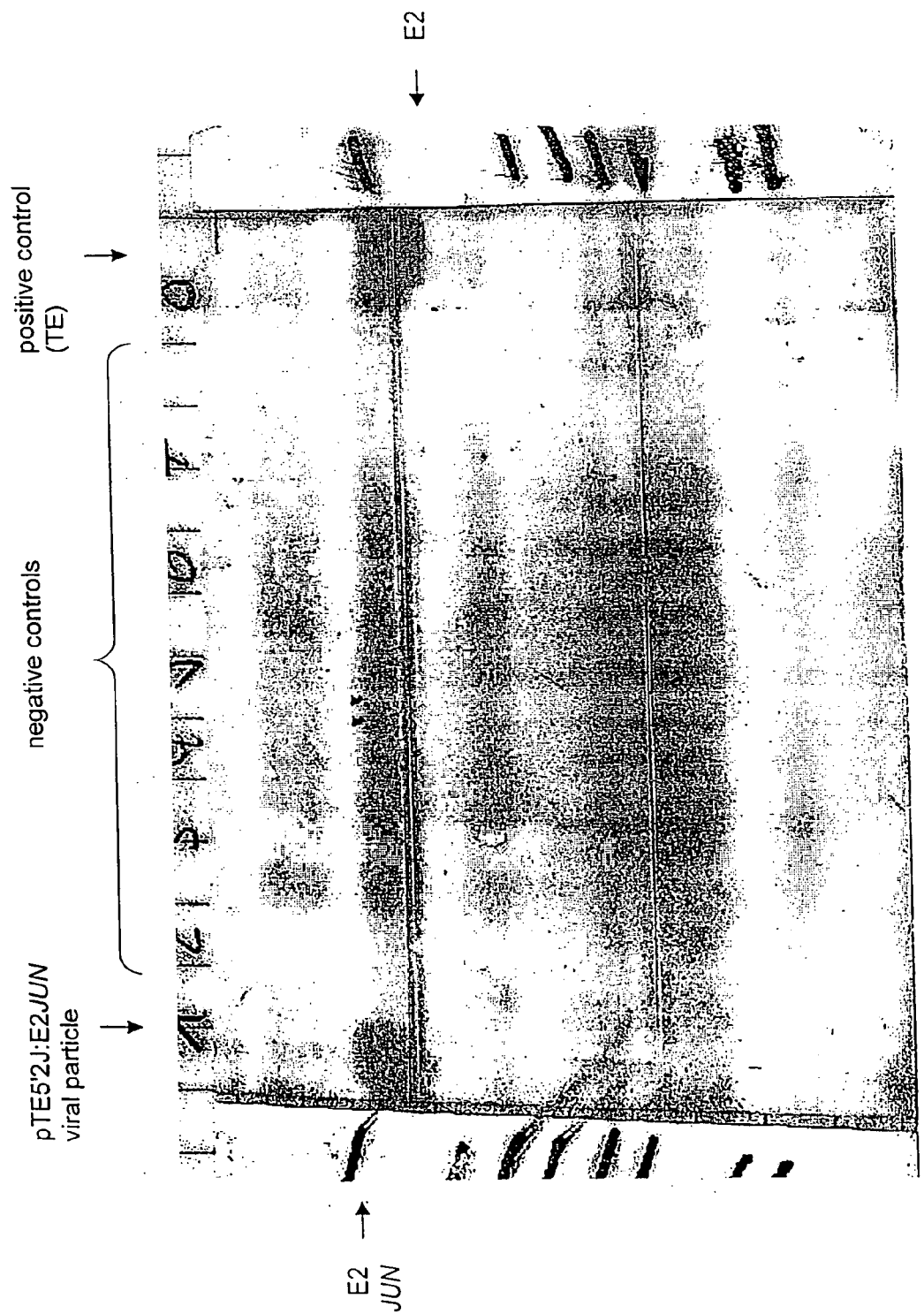
FIG. 2 Western blot demonstrating the production of viral particles containing the E2-JUN fusion protein expressed from pTE5'2J::E2JUN expression vector.

The obtained result was identical to the one obtained with pCYTtsE2:JUN as shown in FIG. 2.

Example 4

Fusion of Human Growth Hormone (hGH) to the FOS Leucine Zipper Domain (OmpA Signal Sequence)

The hGH gene without the human leader sequence was amplified from the original plasmid (ATCC 31389) by PCR. Oligo 7 with an internal XbaI site was designed for annealing at the 5' end of the hGH gene, and oligo 9 with an internal EcoRI site primed at the 3' end of the hGH gene. For the PCR reaction, 100 pmol of each oligo and 5 ng of the template DNA was used in the 75 µl reaction mixture (4 units of Taq or Pwo polymerase, 0.1 mM dNTPs and 1.5 mM MgSO$_4$).

PCR cycling was performed in the following manner: 30 cycles with an annealing temperature of 60° C. and an elongation time of 1 minute at 72° C.

The gel purified and isolated PCR product was used as a template for a second PCR reaction to introduce the ompA signal sequence and the Shine-Dalgarno sequence. For the PCR reaction, 100 pmol of oligo 8 and 9 and 1 ng of the template PCR fragment was used in the 75 µl reaction mixture (4 units of Taq or Pwo polymerase, 0.1 mM dNTPs and 1.5 mM MgSO$_4$). The annealing temperature for the first five cycles was 55° C. with an elongation time of 60 seconds at 72° C.; another 25 cycles were performed with an annealing temperature of 65° C. and an elongation time of 60 seconds at 72° C.

```
Oligo 7:
gggtctagattcccaaccattcccttatccaggcttttttgacaacgctatgctccgcgcccatcgtctgcaccagct    (SEQ ID NO:7)

ggcctttgacacc

Oligo 8:
gggtctagaaggaggtaaaaaacgatgaaaaagacagctatcgcgattgcagtggcactggctggtttcgcta    (SEQ ID NO:8)

ccgtagcgcaggccttcccaaccattcccttatcc

Oligo 9:
cccgaattcctagaagccacagctgccctcc    (SEQ ID NO:9)
```

The resulting recombinant hGH gene was subcloned into pBluescript via XbaI/EcoRI. The correct sequence of both strands was confirmed by DNA sequencing.

The DNA sequence coding for the FOS amphiphatic helix domain was PCR-amplified from vector pJuFo (Crameri & Suter Gene 137:69 (1993)) using the oligonucleotides:

```
omp-FOS:
5'-ccTGCGGTGGTCTGACCGACACCC-3'
(SEQ ID NO:10)

FOS-hgh:
5'-ccgcggaagagccaccGCAACCACCGTGTGCCGCCAGGATG-3'
(SEQ ID NO:11)
```

For the PCR reaction, 100 pmol of each oligo and 5 ng of the template DNA was used in the 75 μl reaction mixture (4 units of Taq or Pwo polymerase, 0.1 mM dNTPs and 1.5 mM MgSO$_4$). The temperature cycles were as follows:

95° C. for 2 minutes, followed by 5 cycles of 95° C. (45 seconds), 60° C. (30 seconds), 72° C. (25 seconds) and followed by 25 cycles of 95° C. (45 seconds), 68° C. (30 seconds), 72° C. (20 seconds).

The PCR product was purified, isolated and cloned into the StuI digested pBluescript-ompA-hGH. The hybrid gene was then cloned into the pKK223-3 Plasmid (Pharmacia).

Example 5

Bacterial Expression of FOS-hGH

The ompA-FOS-hGH in pkk223-3 was expressed under the control of the inducible IPTG-dependend promoter using JM101 as E. coli host strain. Expression was performed in shaker flask. Cells were induced with 1 mM IPTG (final concentration) at an OD600 of 0.5. Expression was continued for 10 hours at 37° C. Cells were harvested by centrifugation at 3600 at 10° C. for 15 min. The cell pellet was frozen (−20° C. or liq. N$_2$) and stored for 16 hours. The pellet was then thawed at 4° C. and resuspended in 10 ml 10 mM Tris-HCl, pH 7.4 containing 600 mM sucrose. After stirring for 15 min at 4° C., periplasmic proteins were released by an osmotic shock procedure. Chilled (4° C.) deionized H$_2$O was added, and the suspension was stirred for 30 min at 4° C. The sludge was diluted, resuspended, and lysozyme was added to degrade the cell wall of the bacteria. The cells and the periplasmic fraction spheroplasts were separated by centrifugation for 20 min at 11000 g at 4° C. The FOS-hGH-containing supernatant was analyzed by reducing and non-reducing SDS-Page and Dot Blot. Dot Blot was carried out as described in Example 8, using an anti-hGH antibody (Sigma) as the first antibody and an alkaline phosphatase (AP)-anti-mouse antibody conjugate as the second antibody.

Figure 3:
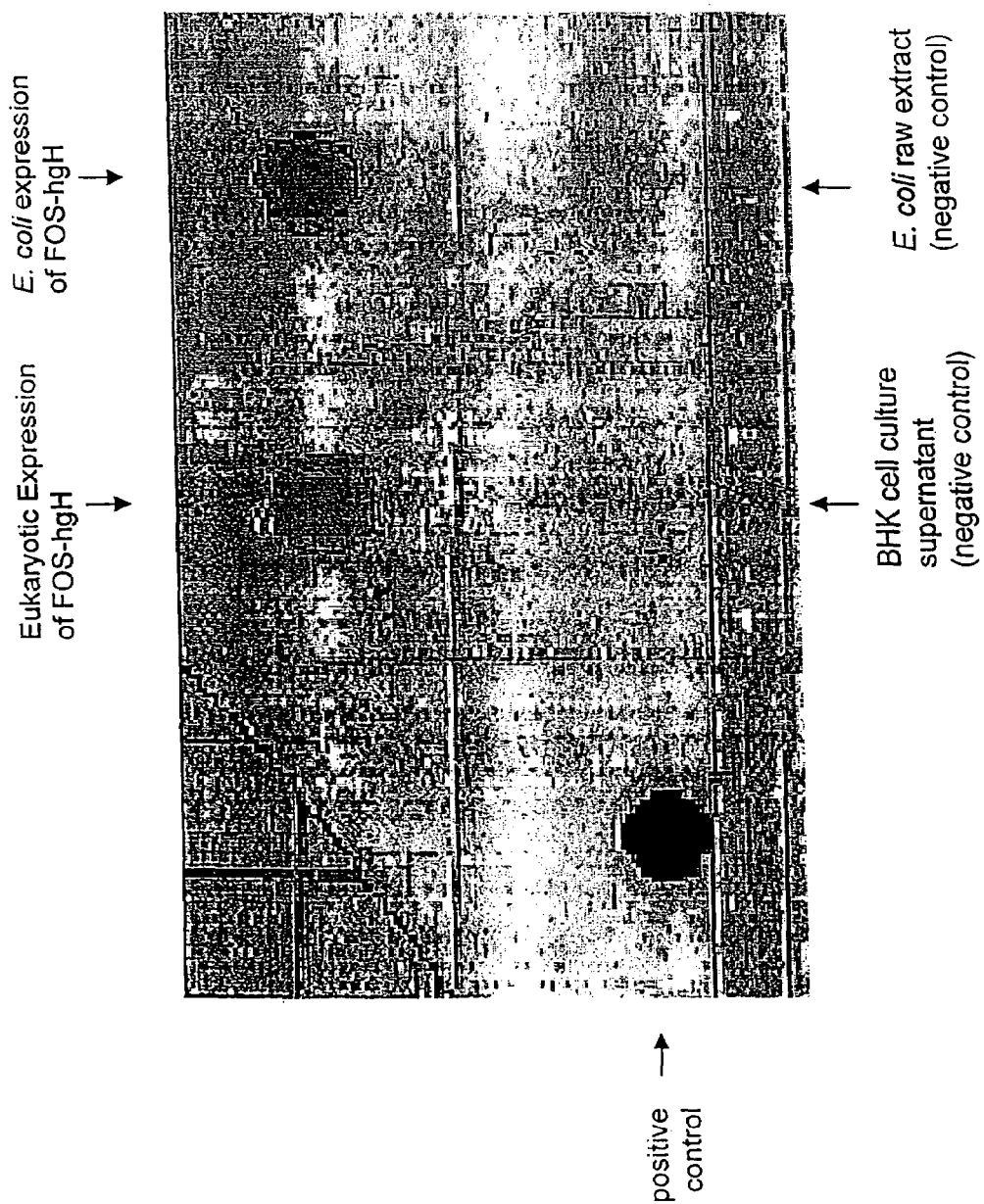
FIG. 3 Western dot blot demonstrating bacterial and eukaryotic expression of the FOS-hgh antigen.

Full length, correctly processed FOS-hGH could be detected under reducing and non-reducing conditions. Part of FOS-hGH was bound to other, non-identified proteins due to the free cysteines present in the FOS amphiphatic helix. However, more than 50% of expressed FOS-hGH occurred in its native monomeric conformation (FIG. 3).

Purified FOS-hGH will be used to perform first doping experiments with JUN containing viral particles.

Example 6

Construction of the pAV Vector Series for Expression of FOS Fusion Proteins

A versatile vector system was constructed that allowed either cytplasmic production or secretion of - or C-terminal FOS fusion proteins in E. coli or production of - or C-terminal FOS fusion proteins in eukaryotic cells. The vectors pAV1–pAV4 which was designed for production of FOS fusion proteins in E. coli, encompasses the DNA cassettes listed below, which contain the following genetic elements arranged in different orders: (a) a strong ribosome binding site and 5'-untranslated region derived from the E. coli ompA gene (aggaggtaaaaaacg) (SEQ ID NO:13); (b) a sequence encoding the signal peptide of E. coli outer membrane protein OmpA (MKKTAIAIAVALAGFATVAQA) (SEQ ID NO:14); (c) a sequence coding for the FOS dimerization domain flanked on both sides by two glycine residues and a cystein residue (CGGLTDTLQAETDQVEDEKSALQTEIANLLKEKEKLEFILAAHGGC) (SEQ ID NO:15); and (d) a region encoding a short peptidic linker (AAASGG (SEQ ID NO:16) or GGSAAA (SEQ ID NO:17)) connecting the protein of interest to the FOS dimerization domain. Relevant coding regions are given in upper case letters. The arrangement of restriction cleavage sites allows easy construction of FOS fusion genes with or without a signal sequence. The cassettes are cloned into the EcoRI/HindIII restriction sites of expression vector pKK223-3 (Pharmacia) for expression of the fusion genes under control of the strong tac promotor.

pAV1

This vector was designed for the secretion of fusion proteins with FOS at the C-terminus into the E. coli periplasmic space. The gene of interest (g.o.i.) may be ligated into the StuI/NotI sites of the vector.

```
EcoRI                          31/11
gaa ttc agg agg taa aaa acg ATG AAA AAG ACA GCT ATC GCG ATT GCA GTG
GCA CTG GCT
                            M   K   K   T   A   I   A   I   A   V   A
L   A
61/21              StuI           NotI
GGT TTC GCT ACC GTA GCG CAG GCC tgg gtg ggg GCG GCC GCT TCT GGT GGT
TGC GGT GGT
G   F   A   T   V   A   Q   A   (goi)     A   A   A   S   G   G   C
G   G
121/41                        151/51
CTG ACC GAC ACC CTG CAG GCG GAA ACC GAC CAG GTG GAA GAC GAA AAA TCC
GCG CTG CAA
L   T   D   T   L   Q   A   E   T   D   Q   V   E   D   E   K   S   A
L   Q
181/61                        211/71
ACC GAA ATC GCG AAC CTG CTG AAA GAA AAA GAA AAG CTG GAG TTC ATC CTG
GCG GCA CAC
T   E   I   A   N   L   L   K   E   K   E   K   L   E   F   I   L   A
A   H
241/81       HindIII
GGT GGT TGC taa gct t     (SEQ ID NO:18)
G   G   C   *   A        (SEQ ID NO:14 and SEQ ID NO:19)
``` pAV2

This vector was designed for the secretion of fusion proteins with FOS at the N-terminus into the *E. coli* periplasmic space. The gene of interest (g.o.i.) ligated into the NotI/EcoRV (or NotI/HindIII) sites of the vector.

```
EcoRI                          31/11
gaa ttc agg agg taa aaa acg ATG AAA AAG ACA GCT ATC GCG ATT GCA GTG
GCA CTG GCT
                            M   K   K   T   A   I   A   I   A   V   A
L   A
61/21              StuI        91/31
GGT TTC GCT ACC GTA GCG CAG GCC TGC GGT GGT CTG ACC GAC ACC CTG CAG
GCG GAA ACC
G   F   A   T   V   A   Q   A   C   G   G   L   T   D   T   L   Q   A
E   T
```

```
                                    -continued
121/41                                151/51
GAC CAG GTG GAA GAC GAA AAA TCC GCG CTG CAA ACC GAA ATC GCG AAC CTG

CTG AAA GAA

D   Q   V   E   D   K   S   A   L   Q   T   E   I   A   N   L   L

K   E

181/61                                                         211/71
                 NotI
AAA GAA AAG CTG GAG TTC ATC CTG GCG GCA CAC GGT GGT TGC GGT GGT TCT

GCG GCC GCT

K   E   K   L   E   F   I   L   A   A   H   G   G   C   G   G   S   A

A   A

241/81       EcoRV   HindIII
ggg tgt ggg gat atc aag ctt    (SEQ ID NO:20)

(goi)                        (SEQ ID NO:21)
``` pAV3

This vector was designed for the cytoplasmic production of fusion proteins with FOS at the C-terminus in *E. coli*. The gene of interest (g.o.i.) may be ligated into the EcoRV/NotI sites of the vector.

```
   EcoRI             EcoRV            NotI
gaa ttc agg agg taa aaa gat atc ggg tgt ggg GCG GCC GCT TCT GGT GGT

TGC GGT GGT (goi)     A   A   A   S   G   G   C

G   G

61/21                                  91/31
CTG ACC GAC ACC CTG CAG GCG GAA ACC GAC CAG GTG GAA GAC GAA AAA TCC

GCG CTG CAA

L   T   D   T   L   Q   A   E   T   D   Q   V   E   D   K   S   A

L   Q

121/41                                 151/51
ACC GAA ATC GCG AAC CTG CTG AAA GAA AAA GAA AAG CTG GAG TTC ATC CTG

GCG GCA CAC

T   E   I   A   N   L   L   K   E   K   E   K   L   E   F   I   L   A

A   H

181/61       HindIII
GGT GGT TGC taa gct t    (SEQ ID NO:22)

G   G   C   *           (SEQ ID NO:23)
``` pAV4

This vector is designed for the cytoplasmic production of fusion proteins with FOS at the N-terminus in *E. coli*. The gene of interest (g.o.i.) may be ligated into the NotI/EcoRV (or NotI/HindIII) sites of the vector. The N-terminal methionine residue is proteolytically removed upon protein synthesis (Hirel et al., *Proc. Natl. Acad. Sci. USA* 86:8247–8251 (1989)).

(c) a region encoding a short peptidic linker (AAASGG (SEQ ID NO:16) or GGSAAA (SEQ ID NO:17)) connecting the protein of interest to the FOS dimerization domain. Relevant coding regions are given in upper case letters. The arrangement of restriction cleavage sites allows easy construction of FOS fusion genes. The cassettes are cloned into the EcoRI/HindIII restriction sites of the expression vector pMPSVEH (Artelt et al., *Gene* 68:213–219 (1988)).

```
EcoRI                           31/11
gaa ttc agg agg taa aaa acg ATG GCT TGC GGT GGT CTG ACC GAC ACC CTG
CAG GCG GAA
 E   F   R   R   *   K   T   M   A   C   G   G   L   T   D   T   L   Q
 A   E 61/21                                    91/31
ACC GAC CAG GTG GAA GAC GAA AAA TCC GCG CTG CAA ACC GAA ATC GCG AAC
CTG CTG AAA
 T   D   Q   V   E   D   E   K   S   A   L   Q   T   E   I   A   N   L
 L   K 121/41                                                        151/51
NotI
GAA AAA GAA AAG CTG GAG TTC ATC CTG GCG GCA CAC GGT GGT TGC GGT GGT
TCT GCG GCC
 E   K   E   K   L   E   F   I   L   A   A   H   G   G   C   G   G   S
 A   A 181/61          EcoRV     HindIII
GCT ggg tgt ggg gat atc aag ctt      (SEQ ID NO:24)
 A      (goi)                        (SEQ ID NO:88 and SEQ ID NO:25)
```

The vectors pAV5 and pAV6, which are designed for eukaryotic production of FOS fusion proteins, encompasses the following genetic elements arranged in different orders: (a) a region coding for the leader peptide of human growth hormone (MATGSRTSLLLAFGLLCLPWLQEGSA) (SEQ ID NO:26); (b) a sequence coding for the FOS dimerization domain flanked on both sides by two glycine residues and a cysteine residue (CGGLTDTLQAETDQVEDEKSALQTE-IANLLKEKEKLEFILAAHGGC) (SEQ ID NO:15); and pAV5

This vector is designed for the eukaryotic production of fusion proteins with FOS at the C-terminus. The gene of interest (g.o.i.) may be inserted between the sequences coding for the hGH signal sequence and the FOS domain by ligation into the Eco47III/NotI sites of the vector. Alternatively, a gene containing its own signal sequence may be fused to the FOS coding region by ligation into the StuI/NotI sites.

```
      EcoRI   StuI                      31/11
      gaa ttc agg cct ATG GCT ACA GGC TCC CGG ACG TCC CTG CTC CTG GCT TTT GCC CTG CTC
                      M   A   T   G   S   R   T   S   L   L   L   A   F   G   L   L 61/21                        Eco47III          NotI
      TGC CTG CCC TGG CTT CAA GAG GGC AGC GCT ggg tgt ggg GCG GCC GCT TCT GGT GGT TGC
       C   L   P   W   L   Q   E   G   S   A   (goi)     A   A   A   S   G   G   C 121/41                                151/51
      GGT GGT CTG ACC GAC ACC CTG CAG GCG GAA ACC GAC CAG GTG GAA GAC GAA AAA TCC GCG
       G   G   L   T   D   T   L   Q   A   E   T   D   Q   V   E   D   E   K   S   A

181/61                       211/71
```

-continued
```
CTG CAA ACC GAA ATC GCG AAC CTG CTG AAA GAA AAA GAA AAG CTG GAG TTC ATC CTG GCG
 L   Q   T   E   I   A   N   L   L   K   E   K   E   K   L   E   F   I   L   A 241/81            HindIII
GCA CAC GGT GGT TGC taa gct t (SEQ ID NO:27)
 A   H   G   G   C   *     (SEQ ID NO:26 and SEQ ID NO:28)
``` pAV6

This vector is designed for the eukaryotic production of fusion proteins with FOS at the N-terminus. The gene of interest (g.o.i.) may be ligated into the NotI/StuI (or NotI/HindIII) sites of the vector.

```
EcoRI                           31/11
gaa ttc ATG GCT ACA GGC TCC CGG ACG TCC CTG CTC CTG GCT TTT GGC CTG CTC TGC CTG
        M   A   T   G   S   R   T   S   L   L   L   A   F   G   L   L   C   L 61/21                 Eco47III         91/31
CCC TGG CTT CAA GAG GGC AGC GCT TGC GGT GGT CTG ACC GAC ACC CTG CAG GCG GAA ACC
 P   W   L   Q   E   G   S   A   C   G   G   L   T   D   T   L   Q   A   E   T 121/41                            151/51
GAC CAG GTG GAA GAC GAA AAA TCC GCG CTG CAA ACC GAA ATC GCG AAC CTG CTG AAA GAA
 D   Q   V   E   D   E   K   S   A   L   Q   T   E   I   A   N   L   L   K   E 181/61                                                        211/71
NotI
AAA GAA AAG CTG GAG TTC ATC CTG GCG GCA CAC GGT GGT TGC GGT GGT TCT GCG GCC GCT
 K   E   K   L   E   F   I   L   A   A   H   G   G   C   G   G   S   A   A   A 241/81       StuI      HindIII
ggg tgt ggg agg cct aag ctt (SEQ ID NO:29)
  (goi)  (SEQ ID NO:30)
```

Construction of Expression Vectors pAV1–pAV6

The following oligonucleotides have been synthesized for construction of expression vectors pAV1–pAV6:

(SEQ ID NO:31)
FOS-FOR1:
CCTGGGTGGGGCGGCCGCTTCTGGTGGTTGCGGTGGTCTGACC;

(SEQ ID NO:32)
FOS-FOR2:
GGTGGGAATTCAGGAGGTAAAAAGATATCGGGTGTGGGGCGGCC;

(SEQ ID NO:33)
FOS-FOR3:
GGTGGGAATTCAGGAGGTAAAAAACGATGGCTTGCGGTGGTCTGACC;

(SEQ ID NO:34)
FOS-FOR4:
GCTTGCGGTGGTCTGACC;

(SEQ ID NO:35)
FOS-REV1:
CCACCAAGCTTAGCAACCACCGTGTGC;

(SEQ ID NO:36)
FOS-REV2:
CCACCAAGCTTGATATCCCCACACCCAGCGGCCGCAGAACCACCGCAACCACCG;

(SEQ ID NO:37)
FOS-REV3:
CCACCAAGCTTAGGCCTCCCACACCCAGCGGC;

(SEQ ID NO:38)
OmpA-FOR1:
GGTGGGAATTCAGGAGGTAAAAAACGATG;

(SEQ ID NO:39)
hGH-FOR1:
GGTGGGAATTCAGGCCTATGGCTACAGGCTCC;

and (SEQ ID NO:40)
hGH-FOR2:
GGTGGGAATTCATGGCTACAGGCTCCC.

For the construction of vector pAV2, the regions coding for the OmpA signal sequence and the FOS domain were amplified from the ompA-FOS-hGH fusion gene in vector pKK223-3 (see Example 5) using the primer pair OmpA-FOR1/FOS-REV2. The PCR product was digested with EcoRI/HindIII and ligated into the same sites of vector pKK223-3 (Pharmacia).

For the construction of vector pAV1, the FOS coding region was amplified from the ompA-FOS-hGH fusion gene in vector pKK223-3 (see Example 5) using the primer pair FOS-FOR1/FOS-REV1. The PCR product was digested with HindIII and ligated into StuI/HindIII digested vector pAV2.

For the construction of vector pAV3, the region coding for the FOS domain was amplified from vector pAV1 using the primer pair FOS-FOR2/FOS-REV1. The PCR product was digested with EcoRI/HindIII and ligated into the same sites of the vector pKK223-3 (Pharmacia).

For the construction of vector pAV4, the region coding for the FOS domain was amplified from the ompA-FOS-hGH fusion gene in vector pKK223-3 (see Example 5) using the primer pair FOS-FOR3/FOS-REV2. The PCR product was digested with EcoRI/HindIII and ligated into the same sites of the vector pKK223-3 (Pharmacia).

For the construction of vector pAV5, the region coding for the hGH signal sequence is amplified from the hGH-FOS-hGH fusion gene in vector pSINrep5 (see Example 7) using the primer pair hGH-FOR1/hGHREV1. The PCR product is digested with EcoRI/NotI and ligated into the same sites of the vector pAV1. The resulting cassette encoding the hGH signal sequence and the FOS domain is then isolated by EcoRI/HindIII digestion and cloned into vector pMPSVEH (Artelt et al., *Gene* 68:213–219 (1988)) digested with the same enzymes.

For the construction of vector pAV6, the FOS coding region is amplified from vector pAV2 using the primer pair FOS-FOR4/FOSREV3. The PCR product is digested with HindIII and cloned into Eco47III/HindIII cleaved vector pAV5. The entire cassette encoding the hGH signal sequence and the FOS domain is then reamplified from the resulting vector using the primer pair hGH-FOR2/FOSREV3, cleaved with EcoRI/HindIII and ligated into vector pMPSVEH (Artelt et al., *Gene* 68:213–219 (1988)) cleaved with the same enzymes.

Example 7

Construction of FOS-hGH with Human (hGH) Signal Sequence

For eukaryotic expression of the FOS-hGH fusion protein, the OmpA-FOS-hGH fusion gene was isolated from pBluescript::OmpA-FOS-hGH (see Example 4) by digestion with XbaI/Bsp120I and cloned into vector pSINrep5 (Invitrogen) cleaved with the same enzymes. The hGH signal sequence was synthesized by PCR (reaction mix: 50 pmol of each primer, dATP, dGTP, dTTP, dCTP (200 μM each), 2.5 U Taq DNA polymerase (Qiagen), 50 μl total volume in the buffer supplied by the manufacturer; amplification: 92° C. for 30 seconds, 55° C. for 30 seconds, 72° C. for 30 seconds, 30 cycles) using the overlapping oligonucleotides Sig-hGH-FOR (GGGTCTAGAATGGCTACAGGCTCCCGGACGTCCCTGCTCCTGGCTT TTGGCCTGCTCTG) (SEQ ID NO:41) and Sig-hGH-REV (CGCAGGCCTCGGCACTGCCCTCTTGAAGCCAGGGCAGGCAGAGCAGGCCAAAAGCCAG) (SEQ ID NO:42). The PCR product was purified using the QiaExII Kit, digested with StuI/XbaI and ligated into vector pSINrep5::OmpA-FOS-hGH cleaved with the same enzymes.

Example 8

Eukaryotic Expression of FOS-hGH

RNase-free vector (1.0 μg) (pSINrep5::OmpA-FOS-hGH) and 1.0 μg of DHEB (Bredenbeek et al., *J. Virol.* 67:6439–6446 (1993)) were linearized by ScaI restriction digest. Subsequently, in vitro transcription was carried out using an SP6 in vitro transcription kit (InvitroscripCAP by InvitroGen, Invitrogen BV, NV Leek, Netherlands). The resulting 5'-capped mRNA was analyzed on reducing agarose-gel.

In vitro, transcribed mRNA 5 μg was electroporated into BHK 21 cells (ATCC: CCL10) according to Invitrogen's manual (Sindbis Expression system, Invitrogen BV, Netherlands). After 10 hours incubation at 37° C. the FCS containing medium was exchanged by HP-1 medium without FCS, followed by an additional incubation at 37° C. for 10 hours. The supernatant was harvested and analyzed by dot-blot analysis for production of FOS-hgh.

Culture media (2.5 μl) was spotted on a nitrocellulose membrane and dried for 10 minutes at room temperature. The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with 2 μg rabbit anti-human hGH antibody (Sigma) in 10 ml TBS-T (TBS with 0.05% Tween20) for 1 hour. The blot was washed 3 times for 10 minutes with TBS-T and incubated for 1 hour with alkaline phosphatase conjugated anti-rabbit IgG (Jackson ImmunoResearch Laboratories, Inc.) diluted 1:5000 in TBS-T. After washing 2 times for 10 minutes with TBS-T and 2 times for 10 minutes with TBS, the blot was developed by AP staining as described in Example 2. Results are shown in FIG. 3.

Example 9

Construction of FOS-PLA (N- and C-Terminal)

The following gene is constructed by chemical gene synthesis coding for a catalytically inactive variant (Förster et al., *J. Allergy Clin. Immunol.* 95: 1229–1235 (1995)) of bee venom phospholipase $A_2$ (PLA).

```
1/1                                             31/11
ATC ATC TAC CCA GGT ACT CTG TGG TGT GGT CAC GGC AAC AAA TCT TCT GGT CCG AAC GAA
 I   I   Y   P   G   T   L   W   C   G   H   G   N   K   S   S   G   P   N   E

61/21                                           91/31
CTC GGC CGC TTT AAA CAC ACC GAC GCA TGC TGT CGC ACC CAG GAC ATG TGT CCG GAC GTC
 L   G   R   F   K   H   T   D   A   C   C   R   T   Q   D   M   C   P   D   V

121/41                                          151/51
ATG TCT GCT GGT GAA TCT AAA CAC GOG TTA ACT AAC ACC GCT TCT CAC ACG CGT CTC AGC
 M   S   A   G   E   S   K   H   G   L   T   N   T   A   S   H   T   R  10   L   S

181/61                                          211/71
TGC GAC TGC GAC GAC AAA TTC TAC GAC TGC CTT AAG AAC TCC GCC GAT ACC ATC TCT TCT
 C   D   C   D   D   K   F   Y   D   C   L   K   N   S   A   D   T   I   S   S

241/81                                          271/91
TAC TTC GTT GGT AAA ATG TAT TTC AAC CTG ATC GAT ACC AAA TGT TAC AAA CTG GAA CAC
```

```
                                     -continued
Y   F   V   G   K   M   Y   F   N   L   I   D   T   K   C   Y   K   L   E   H 301/101                                   331/111
CCG GTA ACC GGC TGC GGC GAA CGT ACC GAA GGT CGC TGC CTG CAC TAC ACC GTT GAC AAA
 P   V   T   G   C   G   E   R   T   E   G   R   C   L   H   Y   T   V   D   K 361/121                                   391/131
TCT AAA CCG AAA GTT TAC CAG TGG TTC GAC CTG CGC AAA TAC (SEQ ID NO:43)
 S   K   P   K   V   Y   Q   W   F   D   L   R   K   Y  (SEQ ID NO:44)
```

For fusion of PLA to the N-terminus of the FOS dimerization domain, the region is amplified using the oligonucleotides PLA-FOR1 (CCATCATCTACCCAGGTAC) (SEQ ID NO:45) and PLA-REV1 (CCC ACACCCAGCGGC-CGCGTATTTGCGCAGGTCG) (SEQ ID NO:46). The PCR product is cleaved with NotI and ligated into vector pAV1 previously cleaved with the restriction enzymes StuI/NotI. For fusion of PLA to the C-terminus of the FOS dimerization domain, the region is amplified using the oligonucleotides PLA-FOR2 (CGGTGGTTCTGCGGC-CGCTATCATCTAC CCAGGTAC) (SEQ ID NO:47) and PLA-REV2 (TTAGTATTTGCGCAGG TCG) (SEQ ID NO:48). The PCR product is cleaved with NotI and ligated into vector pAV2 previously cleaved with the restriction enzymes NotI/EcoRV.

Example 10

Construction of FOS-Ovalbumin Fusion Gene (N- and C-terminal)

For cloning of the ovalbumin coding sequence, mRNA from chicken oviduct tissue is prepared using the Quick-Prep™ Micro mRNA Purification Kit (Pharmacia) according to manufacturer instructions. Using the SuperScript™ One-step RT PCR Kit (Gibco BRL), a cDNA encoding the mature part of ovalbumin (corresponding to nucleotides 68–1222 of the mRNA (McReynolds et al., Nature 273: 723–728 (1978)) is synthesized using the primers Ova-FOR1 (CCGGCTCCATCGGTGCAG) (SEQ ID NO:49) and Ova-REV1 (ACCACCAGAAGCGGCCGCAGGG-GAAACACATCTGCC) (SEQ ID NO:50). The PCR product is digested with NotI and cloned into StuI/NotI digested vector pAV1 for expression of the fusion protein with the FOS dimerization domain at the C terminus. For production of a fusion protein with the FOS dimerization domain at the N terminus, the Ovalbumin coding region is amplified from the constructed vector (pAV1::Ova) using the primers Ova-FOR2 (CGGTGGTTCTGCGGCCGCTGGCTC-CATCGGTGCAG) (SEQ ID NO:51) and Ova-REV2 (TTAAGGGGAAACACATCTGCC) (SEQ ID NO:52). The PCR product is digested with NotI and cloned into the NotI/EcoRV digested vector pAV2. Cloned fragments are verified by DNA sequence analysis.

Example 11

Production and Purification of FOS-PLA and FOS Ovalbumin Fusion Proteins

For cytoplasmic production of FOS fusion proteins, an appropriate E. coli strain was transformed with the vectors pAV3::PLA, pAV4::PLA, pAV3::Ova or pAV4::Ova. The culture was incubated in rich medium in the presence of ampicillin at 37° C. with shaking. At an optical density (550 nm) of 1, 1 mM IPTG was added and incubation was continued for another 5 hours. The cells were harvested by centrifugation, resuspended in an appropriate buffer (e.g. tris-HCl, pH 7.2, 150 mM NaCl) containing DNase, RNase and lysozyme, and disrupted by passage through a french pressure cell. After centrifugation (Sorvall RC-5C, SS34 rotor, 15000 rpm, 10 min, 4° C.), the pellet was resuspended in 25 ml inclusion body wash buffer (20 mM tris-HCl, 23% sucrose, 0.5% Triton X-100, 1 mM EDTA, pH8) at 4° C. and recentrifuged as described above. This procedure was repeated until the supernatant after centrifugation was essentially clear. Inclusion bodies were resuspended in 20 ml solubilization buffer (5.5 M guanidinium hydrochloride, 25 mM tris-HCl, pH 7.5) at room temperature and insoluble material was removed by centrifugation and subsequent passage of the supernatant through a sterile filter (0.45 µm). The protein solution was kept at 4° C. for at least 10 hours in the presence of 10 mM EDTA and 100 mM DTT and then dialyzed three times against 10 volumes of 5.5 M guanidinium hydrochloride, 25 mM tris-HCl, 10 mM EDTA, pH 6. The solution was dialyzed twice against 5 liters of 2 M urea, 4 mM EDTA, 0.1 M NH$_4$Cl, 20 mM sodium borate (pH 8.3) in the presence of an appropriate redox shuffle (oxidized glutathione/reduced glutathione; cystine/cysteine). The refolded protein was then applied to an ion exchange chromatography. The protein was stored in an appropriate buffer with a pH above 7 in the presence of 2–10 mM DTT to keep the cysteine residues flanking the FOS domain in a reduced form. Prior to coupling of the protein with the alphavirus particles, DTT was removed by passage of the protein solution through a Sephadex G-25 gel filtration column.

Example 12

Constructions of Gp140-FOS

The gp140 gene (Swiss-Prot:P03375) without the internal protease cleavage site was amplified by PCR from the original plasmid pAbT4674 (ATCC 40829) containing the full length gp160 gene using the following oligonucleotides:

```
HIV-1:                                                              (SEQ ID NO: 53)
5'-ACTAGTCTAGAatgagagtgaaggagaaatatc-3';

HIV-end:                                                            (SEQ ID NO: 54)
5'-TAGCATGCTAGCACCGAAtttatctaattccaataattcttg-3';

HIV-Cleav:                                                          (SEQ ID NO:55)
5'-gtagcacccaccaaggcaaagCTGAAAGCTACCCAGCTCGAGAAACTGgca-3';
and HIV-Cleav2:                                                         (SEQ ID NO:56)
5'-caaagctcctattcccactgcCAGTTTCTCGAGCTGGGTAGCTTTCAG-3'.
```

For PCR I, 100 pmol of oligo HIV-1 and HIV-Cleav2 and 5 ng of the template DNA were used in the 75 µl reaction mixture (4 units of Taq or Pwo polymerase, 0.1 mM dNTPs and 1.5 mM $MgSO_4$). PCR cycling was done in the following manner: 30 cycles with an annealing temperature of 60° C. and an elongation time of 2 minutes at 72° C.

For PCR II, 100 pmol of oligo HIV-end and HIV-Cleav and 5 ng of the template DNA were used in the 75 µl reaction mixture, (4 units of Taq or Pwo polymerase, 0.1 mM dNTPs and 1.5 mM $MgSO_4$). PCR cycling was done in the following manner: 30 cycles with an annealing temperature of 60° C. and an elongation time of 50 seconds at 72° C.

Both PCR fragments were purified, isolated and used in an assembly PCR reaction. For the assembly PCR reaction, 100 pmol of oligo HIV-1 and HIV-end and 2 ng of each PCR fragment (PCRI and PCR II) were used in the 75 µl (4 units of Taq or Pwo polymerase, 0.1 mM dNTPs and 1.5 mM $MgSO_4$). PCR cycling was done in the following manner: 30 cycles with an annealing temperature of 60° C. and an elongation time of 2.5 minutes at 72° C. The assembly PCR product was digested XbaI and NheI. The FOS amphiphatic helix was fused in frame to the C-terminal end of gp-140.

The DNA sequence coding for the FOS amphiphatic helix domain was PCR-amplified from vector pJuFo (Crameri & Suter Gene 137: 69 (1993)) using the oligonucleotides:

```
FOS-HIV: 5'-ttcggtgctagcggtggcTGCGGTGGTCTGACCGAC-3'; (SEQ ID NO:57)
and

FOS-Apa: 5'-gatgctgggcccttaaccGCAACCACCGTGTGCCGCC-3'. (SEQ ID NO:58)
```

For the PCR reaction, 100 pmol of each oligo and 5 ng of the template DNA was used in the 75 µl reaction mixture (4 units of Taq or Pwo polymerase, 0.1 mM dNTPs and 1.5 mM $MgSO_4$). Temperature cycling was done as follows:

95° C. for 2 minutes, followed by 5 cycles of 95° C. (45 seconds), 60° C. (30 seconds), 72° C. (25 seconds) and followed by 25 cycles of 95° C. (45 seconds), 68° C. (30 seconds), 72° C. (20 seconds). The obtained PCR fragment was digested with NheI and Bsp120L.

The final expression vector for GP140-FOS was obtained in a 3 fragment ligation of both PCR fragments into pSinRep5. The resultant vector pSinRep5-GP140-FOS was evaluated by restriction analysis and DNA sequencing.

GP140-FOS was also cloned into pCYTts via XbaI and Bsp120L to obtain a stable, inducible GP140-FOS expressing cell line.

Example 13

Expression of GP140FOS Using pSinRep5-GP140FOS

RNase-free vector (1.0 µg) (pSinRep5-GP140-FOS) and 1.0 µg of DHEB (Bredenbeek et al., *J. Virol.* 67:6439–6446 (1993)) were linearized by restriction digestion. Subsequently, in vitro transcription was carried out using an SP6 in vitro transcription kit (InvitroscripCAP by InvitroGen, Invitrogen BV, NV Leek, Netherlands). The resulting 5'-capped mRNA was analyzed on a reducing agarose-gel.

In vitro transcribed mRNA (5 µg) was electroporated into BHK 21 cells (ATCC: CCL10) according to Invitrogen's manual (Sindbis Expression System, Invitrogen BV, Netherlands). After 10 hours incubation at 37° C., the FCS containing medium was exchanged by HP-1 medium without FCS, followed by an additional incubation at 37° C. for 10 hours. The supernatant was harvested and analyzed by Western blot analysis for production of soluble GP140-FOS exactly as described in Example 2.

Example 14

Expression of GP140FOS Using pCYTts-GP140FOS pCYT-GP140-FOS 20 µg was linearized by restriction digestion. The reaction was stopped by phenol/chloroform extraction, followed by an isopropanol precipitation of the linearized DNA. The restriction digestion was evaluated by agarose gel eletrophoresis. For the transfection, 5.4 µg of linearized pCYTtsGP140-FOS was mixed with 0.6 µg of linearized pSV2Neo in 30 µl $H_2O$ and 30 µl of 1 M $CaCl_2$ solution was added. After addition of 60 µl phosphate buffer (50 mM HEPES, 280 mM NaCl, 1.5 mM $Na_2$ $HPO_4$, pH 7.05), the solution was vortexed for 5 seconds, followed by an incubation at room temperature for 25 seconds. The solution was immediately added to 2 ml HP-1 medium containing 2% FCS (2% FCS medium). The medium of an 80% confluent BHK21 cell culture (6-well plate) was then-replaced by the DNA containing medium. After an incubation for 5 hours at 37° C. in a $CO_2$ incubator, the DNA containing medium was removed and replaced by 2 ml of 15% glycerol in 2% FCS medium. The glycerol containing medium was removed after a 30 second incubation phase, and the cells were washed by rinsing with 5 ml of HP-1 medium containing 10% FCS. Finally 2 ml of fresh HP-1 medium containing 10% FCS was added.

Stably transfected cells were selected and grown in selection medium (HP-1 medium supplemented with G418) at 37° C. in a $CO_2$ incubator. When the mixed population was grown to confluency, the culture was split to two dishes, followed by a 12 h growth period at 37° C. One dish of the cells was shifted to 30° C. to induce the expression of soluble GP140-FOS. The other dish was kept at 37° C.

The expression of soluble GP140-FOS was determined by Western blot analysis. Culture media (0.5 ml) was methanol/chloroform precipitated, and the pellet was resuspended in SDS-PAGE sample buffer. Samples were heated for 5 minutes at 95° C. before being applied to a 15% acrylamide gel. After SDS-PAGE, proteins were transferred to Protan nitrocellulose membranes (Schleicher & Schuell, Germany) as described by Bass and Yang, in Creighton, T. E., ed., *Protein Function: A Practical Approach*, 2nd Edn., IRL Press, Oxford (1997), pp. 29–55. The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with an anti-GP140 or GP-160 antibody for 1 hour. The blot was washed 3 times for 10 minutes with TBS-T (TBS with 0.05% Tween20), and incubated for 1 hour with an alkaline-phosphatase-antimouse/rabbit/monkey/human IgG conjugate. After washing 2 times for 10 minutes with TBS-T and 2 times for 10 minutes with TBS, the development reaction was carried out using alkaline phosphatase detection reagents (10 ml AP buffer (100 mM Tris/HCl, 100 mM NaCl, pH 9.5) with 50 µl NBT solution (7.7% Nitro Blue Tetrazolium (Sigma) in 70% dimethylformamide) and 37 µl of X-Phosphate solution (5% of 5-bromo-4-chloro-3-indolyl phosphate in dimethylformamide).

Example 15

Production and Purification of GP140FOS

An anti-gp120 antibody was covalently coupled to a NHS/EDC activated dextran and packed into a chromatography column. The supernatant, containing GP140FOS is loaded onto the column and after sufficient washing, GP140FOS was eluted using 0.1 M HCl. The eluate was directly neutralized during collection using 1 M Tris pH 7.2 in the collection tubes.

Disulfide bond formation might occur during purification, therefore the collected sample is treated with 10 mM DTT in 10 mM Tris pH 7.5 for 2 hours at 25° C.

DTT is remove by subsequent dialysis against 10 mM Mes; 80 mM NaCl pH 6.0. Finally GP140FOS is mixed with alphavirus particles containing the JUN leucine zipper in E2 as described in Example 16.

Example 16

Preparation of the AlphaVaccine Particles

Viral particles (see Examples 2 and 3) were concentrated using Millipore Ultrafree Centrifugal Filter Devices with a molecular weight cut-off of 100 kD according to the protocol supplied by the manufacturer. Alternatively, viral particles were concentrated by sucrose gradient centrifugation as described in the instruction manual of the Sindbis Expression System (Invitrogen, San Diego, Calif.). The pH of the virus suspension was adjusted to 7.5 and viral particles were incubated in the presence of 2–10 mM DTT for several hours. Viral particles were purified from contaminating protein on a Sephacryl S-300 column (Pharmacia) (viral particles elute with the void volume) in an appropriate buffer.

Purified virus particles were incubated with at least 240 fold molar excess of FOS-antigen fusion protein in an appropriate buffer (pH 7.5–8.5) in the presence of a redox shuffle (oxidized glutathione/reduced glutathione; cystine/cysteine) for at least 10 hours at 4° C. After concentration of the particles using a Millipore Ultrafree Centrifugal Filter Device with a molecular weight cut-off of 100 kD, the mixture was passed through a Sephacryl S-300 gel filtration column (Pharmacia). Viral particles were eluted with the void volume.

Example 17

Fusion of JUN Amphipathic Helix to the Amino Terminus of HBcAg(1–144)

The JUN helix was fused to the amino terminus of the HBcAg amino acid sequence 1 to 144 (JUN-HBcAg construct). For construction of the JUN-HBcAg DNA sequence, the sequences encoding the JUN helix and HBcAg(1–144) were amplified separately by PCR. The JUN sequence was amplified from the pJuFo plasmid using primers EcoRI-JUN(s) and JUN-SacII(as). The EcoRI-JUN(s) primer introduced an EcoRI site followed by a start ATG codon. The JUN-SacII(as) primer introduced a linker encoding the amino acid sequence GAAGS. The HBcAg (1–144) sequence was amplified from the pEco63 plasmid (obtained from ATCC No. 31518) using primers JUN-HBcAg(s) and HBcAg(1–144)Hind(as). JUN-HBcAg(s) contained a sequence corresponding to the 3' end of the sequence encoding the JUN helix followed by a sequence encoding the GAAGS linker and the 5' end of the HBcAg sequence. HBcAg(1–144)Hind(as) introduces a stop codon and a HindIII site after codon 144 of the HBcAg gene. For the PCR reactions, 100 pmol of each oligo and 50 ng of the template DNAs were used in the 50 µl reaction mixtures with 2 units of Pwo polymerase, 0.1 mM dNTPs and 2 mM $MgSO_4$. For both reactions, temperature cycling was carried out as follows: 94° C. for 2 minutes; and 30 cycles of 94° C. (1 minute), 50° C. (1 minute), 72° C. (2 minutes).

| | |
|---|---|
| EcoRI-JUN(s): (5'-CCGGAATTCATGTGCGGTGGTCGGATCGCCCGG-3'); | (SEQ ID NO:61) |
| JUN-SacII(as): (5'-GTCGCTACCCGCGGCTCCGCAACCAACGTGGTTCATGAC-3'); | (SEQ ID NO:62) |

-continued

```
JUN-HBcAg(s):    (5'-GTTGGTTGCGGAGCCGCGGGTAGCGACATTGACCCTTATAAAGAATTTGG-3');  (SEQ ID NO:63)

HBcAg(1-144)Hind(as):  (5'-CGCGTCCCAAGCTTCTACGGAAGCGTTGATAGGATAGG-3').         (SEQ ID NO:64)
```

Fusion of the two PCR fragments was performed by PCR using primers EcoRI-JUN(s) and HBcAg(1–144)Hind(as). 100 pmol of each oligo was used with 100 ng of the purified PCR fragments in a 50 μl reaction mixture containing 2 units of Pwo polymerase, 0.1 mM dNTPs and 2 mM MgSO₄. PCR cycling conditions were: 94° C. for 2 minutes; and 35 cycles of 94° C. (1 minute), 50° C. (1 minute), 72° C. (2 minutes). The final PCR product was analyzed by agarose gel electrophoresis, purified and digested for 16 hours in an appropriate buffer with EcoRI and HindIII restriction enzymes. The digested DNA fragment was ligated into EcoRI/HindIII-digested pKK vector to generate pKK-JUN-HBcAg expression vector. Insertion of the PCR product was analyzed by EcoRI/HindIII restriction analysis and by DNA sequencing of the insert.

Example 18

Fusion of JUN Amphipathic Helix to the Carboxy Terminus of HBcAg(1–144)

The JUN helix was fused to the carboxy terminus of the HBcAg amino acid sequence 1 to 144 (HBcAg-JUN construct). For construction of the HBcAg-JUN DNA sequence, the sequences encoding the JUN helix and HBcAg(1–144) were amplified separately by PCR. The JUN sequence was amplified from the pJuFo plasmid with primers SacII-JUN(s) and JUN-HindIII(as). SacII-JUN(s) introduced a linker encoding amino acids LAAG. This sequence also contains a SacII site. JUN-HindIII(as) introduced a stop codon (TAA) followed by a HindIII site. The HBcAg (1–144) DNA sequence was amplified from the pEco63 plasmid using primers EcoRI-HBcAg(s) and HBcAg (1–144)-JUN(as). EcoRI-HBcAg(s) introduced an EcoRI site prior to the Start ATG of the HBcAg coding sequence. HBcAg(1–144)-JUN(as) introduces a sequence encoding the peptide linker (LAAG), which also contains a SacII site. For the PCR reactions, 100 pmol of each oligo and 50 ng of the template DNAs were used in the 50 μl reaction mixtures with 2 units of Pwo polymerase, 0.1 mM dNTPs and 2 mM MgSO₄. Temperature cycling was carried out as follows: 94° C. for 2 minutes; and 30 cycles of 94° C. (1 minute), 50° C. (1 minute), 72° C. (2 minutes).

Primer sequences minutes; and 35 cycles of 94° C. (1 minute), 50° C. (1 minute), 72° C. (2 minutes). The final PCR product was analyzed by agarose gel electrophoresis, and digested for 16 hours in an appropriate buffer with EcoRI and HindIII restriction enzymes. The DNA fragment was gel purified and ligated into EcoRI/HindIII-digested pKK vector to generate pKK-HBcAg-JUN expression vector. Insertion of the PCR product was analyzed by EcoRI/HindIII restriction analysis and by DNA sequencing of the insert.

Example 19

Insertion of JUN Amphipathic Helix into the c/e1 Epitope of HBcAg(1–144)

The c/e1 epitope (residues 72 to 88) of HBcAg is known to be located in the tip region on the surface of the hepatitis B virus capsid. A part of this region (residues 76 to 82) of the protein was genetically replaced by the JUN helix to provide an attachment site for antigens (HBcAg-JUNIns construct). The HBcAg-JUNIns DNA sequence was generated by PCRs: The JUN helix sequence and two sequences encoding HBcAg fragments (amino acid residues 1 to 75 and 83 to 144) were amplified separately by PCR. The JUN sequence was amplified from the pJuFo plasmid with primers BamHI-JUN(s) and JUN-SacII(as). BamHI-JUN(s) introduced a linker sequence encoding the peptide sequence GSGGG that also contains a BamHI site. JUN-SacII(as) introduced a sequence encoding the peptide linker GAAGS followed by a sequence complementary to the 3' end of the JUN coding sequence. The HBcAg(1–75) DNA sequence was amplified from the pEco63 plasmid using primers EcoRIHBcAg(s) and HBcAg75-JUN(as). EcoRIHBcAg(s) introduced an EcoRI site followed by a sequence corresponding to the 5' end of the HBcAg sequence. HBcAg75-JUN(as) introduced a linker encoding the peptide GSGGG after amino acid 75 of HBcAg followed by a sequence complementary to the 5' end of the sequence encoding the JUN helix. The HBcAg (83–144) fragment was amplified using primers JUN-HBcAg83(s) and HBcAg(1–144)Hind (as). JUN-HBcAg83(s) contained a sequence corresponding to the 3' end of the JUN-encoding sequence followed by a linker encoding the peptide, GAAGS and a sequence corresponding to the 5' end of the sequence encoding HBcAg (83–144). HBcAg(1–144)Hind(as) introduced a stop codon and a HindIII site after codon 144 of the HBcAg gene. For the PCR reactions, 100 pmol of each oligo and 50 ng of the template DNAs were used in the 50 μl reaction mixtures (2 units of Pwo polymerase, 0.1 mM dNTPs and 2 mM $MgSO_4$). Temperature cycling was performed as follows:

94° C. for 2 minutes; and 35 cycles of 94° C. (1 minute), 50° C. (1 minute), 72° C. (2 minutes).

Primer Sequences:

```
BamHI-JUN(s):     (5'-CTAATGGATCCGGTGGGGGCTGCGGTGGTCGGATCGCCCGGCTCGAG-3');      (SEQ ID NO:69)

JUN-SacII(as):    (5'-GTCGCTACCCGCGGCTCCGCAACCAACGTGGTTCATGAC-3');               (SEQ ID NO:70)

EcoRIHBcAg(s):    (5'-CCGGAATTCATGGACATTGACCCTTATAAAG-3');                       (SEQ ID NO:71)

HBcAg75-JUN (as): (5'-CCGACCACCGCAGCCCCCACCGGATCCATTAGTACCCACCCAGGTAGC-3');     (SEQ ID NO:72)

JUN-HRcAg83(s):   (5'-GTTGGTTGCGGAGCCGCGGGTAGCGACCTAGTAGTCAGTITATGTC-3');        (SEQ ID NO:73)
and HBcAg(1-144)Hind(as): (5'-CGCGTCCCAAGCTTCTACGGAAGCGTTGATAGGATAGG-3').             (SEQ ID NO:74)
```

Fusion of the three PCR fragments was performed as follows. First, the fragment encoding HBcAg 1–75 was fused with the sequence encoding JUN by PCR using primers EcoRIHBcAg(s) and JUN-SacII(as). Second, the product obtained was fused with the HBcAg(83–144) fragment by PCR using primers EcoRI HBcAg(s) and HBcAg HindIII(as). For PCR fusions, 100 pmol of each oligo was used with 100 ng of the purified PCR fragments in a 50 µl reaction mixture containing 2 units of Pwo polymerase, 0.1 mM dNTPs and 2 mM MgSO$_4$. The same PCR cycles were used as for generation of the individual fragments. The final PCR product was digested for 16 hours in an appropriate buffer with EcoRI and HindIII restriction enzymes. The DNA fragment was ligated into EcoRI/HindIII-digested pKK vector, yielding the pKK-HBcAg-JUNIns vector. Insertion of the PCR product was analyzed by EcoRI/HindIII restriction analysis and by DNA sequencing of the insert.

Example 20

Fusion of the JUN Amphipathic helix to the Carboxy Terminus of the Measles Virus Nucleocapsid (N) Protein The JUN helix was fused to the carboxy terminus of the truncated measles virus N protein fragment comprising amino acid residues 1 to 473 ($N_{473}$-JUN construct). For construction of the DNA sequence encoding N473-JUN the sequence encoding the JUN helix and the sequence encoding N473-JUN were amplified separately by PCR. The JUN sequence was amplified from the pJuFo plasmid with primers SacII-JUN(s) and JUN-HindIII(as). SacII-JUN(s) introduced a sequence encoding peptide linker LAAG. This sequence also contained a SacII site. The JUN-HindIII(as) anti-sense primer introduced a stop codon (TAA) followed by a HindIII site. The N (1–473) sequence was amplified from the pSC-N plasmid containing the complete measles virus N protein coding sequence (obtained from M. Billeter, Zurich) using primers EcoRI-Nmea(s) and Nmea-JUN(as). EcoRI-N(mea)(s) introduced an EcoRI site prior to the Start ATG of the N coding sequence. N(mea)-JUN(as) was complementary to the 3' end of the N(1–473) coding sequence followed by a sequence complementary to the coding sequence for the peptide linker (LAAG). For the PCR reactions, 100 pmol of each oligo and 50 ng of the template DNAs were used in the 50 µl reaction mixtures with 2 units of Pwo polymerase, 0.1 mM dNTPs and 2 mM MgSO$_4$. Temperature cycling was performed as follows: 94° C. for 2 minutes; and 35 cycles of 94° C. (1 minute), 55° C. (1 minute), 72° C. (2 minutes).

Primer Sequences:

```
SacII-JUN(s):     (5'-CTAGCCGCGGGTTGCGGTGGTCGGATCGCCCGG-3');         (SEQ ID NO:75)

JUN-HindIII(as):  (5'-CGCGTCCCAAGCTTTTAGCAACCAACGTGGTTCATGAC -3');   (SEQ ID NO:76)

EcoRI-Nmea(s):    (5'-CCGGAATTCATGGCCACACTTTTAAGGAGC-3');            (SEQ ID NO:77)
and Nmea-JUN(as):     (5'-CGCGTCCCAAGCTTTTAGCAACCAACGTGGTTCATGAC-3').    (SEQ ID NO:78)
```

Fusion of the two PCR fragments was performed in a further PCR using primers EcoRI-Nmea(s) and Nmea-JUN (as). For the PCR fusion, 100 pmol of each oligo was used with 100 ng of the purified PCR fragments in a 50 µl reaction mixture containing 2 units of Pwo polymerase, 0.1 mM dNTPs and 2 mM MgSO$_4$. Temperature cycling was performed as follows: 94° C. for 2 minutes; and 35 cycles of 94° C. (1 minute), 50° C. (1 minute), 72° C. (2 minutes). The PCR product was digested for 16 hours in an appropriate buffer with EcoRI and HindIII restriction enzymes. The DNA fragment was gel purified and ligated into EcoRI/HindIII-digested pKK vector, yielding the pKK-N473-JUN plasmid. Insertion of the PCR product was analyzed by EcoRI/HindIII restriction analysis and by DNA sequencing of the insert.

Example 21

Expression and Partial Purification of HBcAg-JUN

Figure 4:
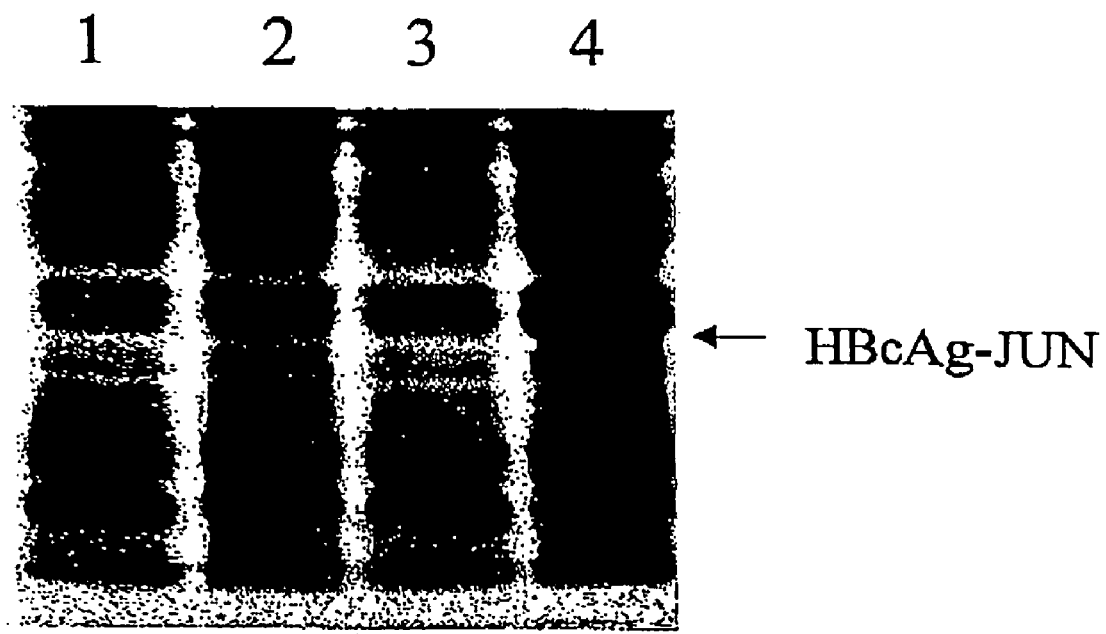
FIG. 4 Expression of HBcAg-JUN in $E.\ coli$ cells.

*E. coli* strain XL-1 blue was transformed with pKK-HBcAg-JUN. 1 ml of an overnight culture of bacteria was used to innoculate 100 ml of LB medium containing 100 µg/ml ampicillin. This culture was grown for 4 hours at 37° C. until an OD at 600 nm of approximately 0.8 was reached. Induction of the synthesis of HBcAg-JUN was performed by addition of IPTG to a final concentration of 1 mM. After induction, bacteria were further shaken at 37° C. for 16 hours. Bacteria were harvested by centrifugation at 5000×g for 15 minutes. The pellet was frozen at −20° C. The pellet was thawed and resuspended in bacteria lysis buffer (10 mM Na$_2$HPO$_4$, pH 7.0, 30 mM NaCl, 0.25% Tween-20, 10 mM EDTA, 10 mM DTT) supplemented with 200 µg/ml lysosyme and 10 µl of Benzonase (Merck). Cells were incubated for 30 minutes at room temperature and disrupted using a French pressure cell. Triton X-100 was added to the lysate to a final concentration of 0.2%, and the lysate was incubated for 30 minutes on ice and shaken occasionally. FIG. 4 shows HBcAg-JUN protein expression in *E. coli* upon induction with IPTG. *E. coli* cells harboring pKK-HBcAg-JUN expression plasmid or a control plasmid were used for induction of HBcAg-JUN expression with IPTG. Prior to the addition of IPTG, a sample was removed from the bacteria culture carrying the pKK-HBcAg-JUN plasmid (lane 3) and from a culture carrying the control plasmid (lane 1). Sixteen hours after addition of IPTG, samples were again removed from the culture containing pKK-HBcAg-JUN (lane 4) and from the control culture (lane 2). Protein expression was monitored by SDS-PAGE followed by Coomassie staining.

Figure 5:
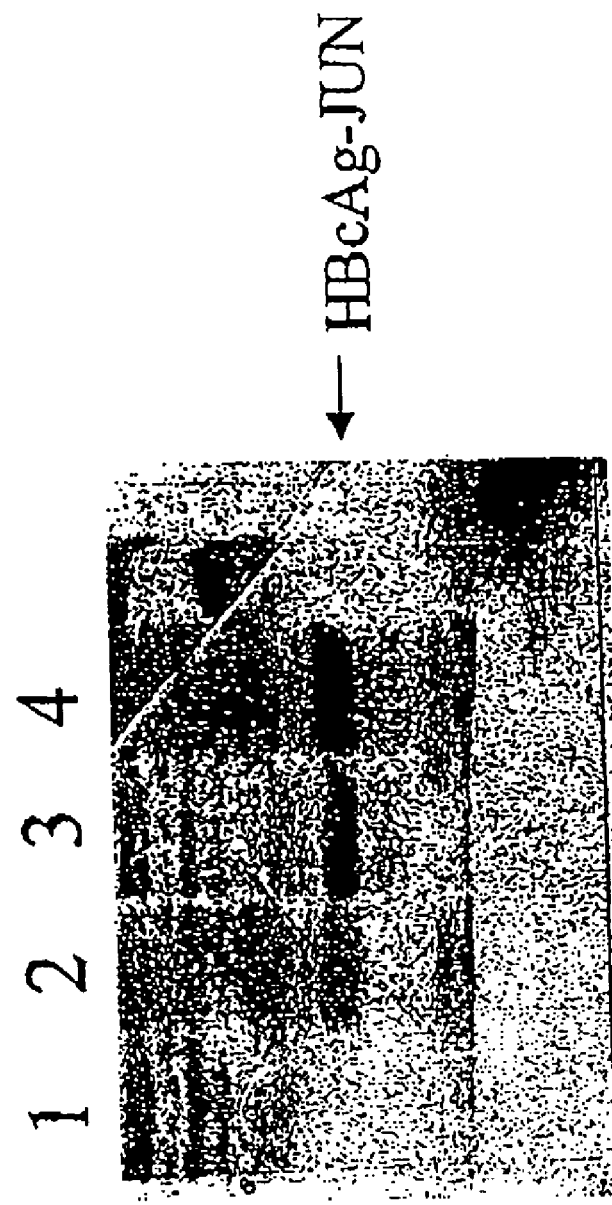
FIG. 5 Western blot demonstrating that HBcAg-JUN is soluble in $E.\ coli$ lysates.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., USA), indicating that a significant amount of HBcAg-JUN protein was soluble (FIG. 5). Briefly, lysates from *E. coli* cells expressing HBcAg-JUN and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841. Lane 1: soluble fraction, control cells; lane 2: insoluble fraction, control cells; lane 3: soluble fraction, cells expressing HBcAg-JUN; lane 4: insoluble fraction, cells expressing HbcAg-JUN.

Figure 6:
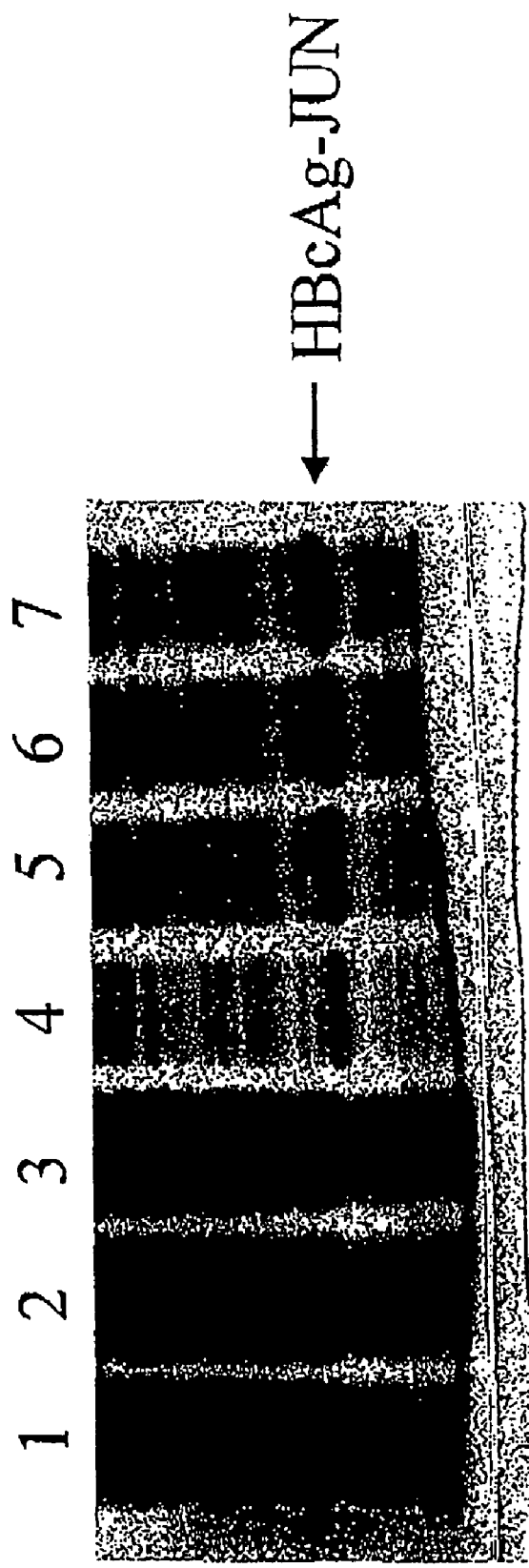
FIG. 6 SDS-PAGE analysis of enrichment of HBcAg-JUN capsid particles on a sucrose density gradient.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. (FIG. 6). Lane 1: total *E. coli* lysate prior to centrifugation. Lane 1 and 2: fractions 1 and 2 from the top of the gradient. Lane 4 to 7: fractions 5 to 8 (15% sucrose). The HBcAg-JUN protein was detected by Coomassie staining.

The HBcAg-JUN protein was enriched at the interface between 15 and 65% sucrose indicating that it had formed a capsid particle. Most of the bacterial proteins remained in the sucrose-free upper layer of the gradient, therefore step-gradient centrifugation of the HBcAg-JUN particles led both to enrichment and to a partial purification of the particles.

Example 22

Covalent Coupling of hGH-FOS to HBcAg-JUN

Figure 7:
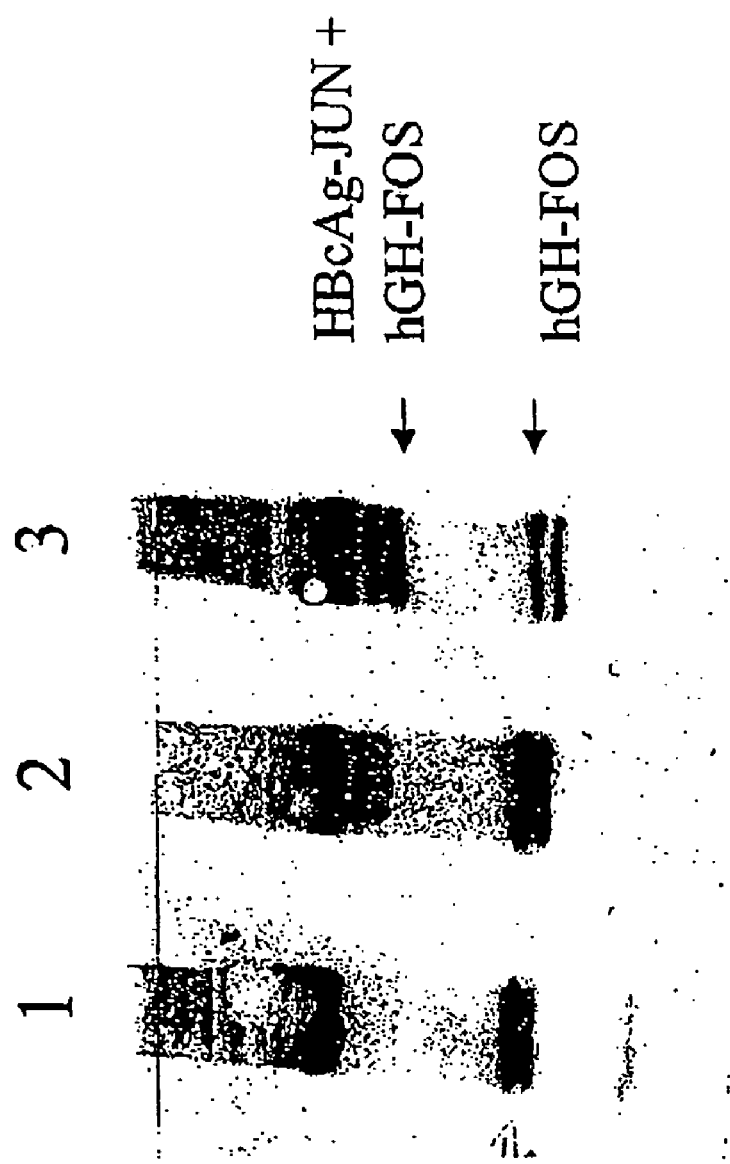
FIG. 7 Non-reducing SDS-PAGE analysis of the coupling of hGH-FOS and HBcAg-JUN particles.

In order to demonstrate binding of a protein to HBcAg-JUN particles, we chose human growth hormone (hGH) fused with its carboxy terminus to the FOS helix as a model protein (hGH-FOS). HBcAg-JUN particles were mixed with partially purified hGH-FOS and incubated for 4 hours at 4° C. to allow binding of the proteins. The mixture was then dialyzed overnight against a 3000-fold volume of dialysis buffer (150 mM NaCl, 10 mM Tris-HCl solution, pH 8.0) in order to remove DTT present in both the HBcAg-JUN solution and the hGH-FOS solution and thereby allow covalent coupling of the proteins through the establishment of disulphide bonds. As controls, the HBcAg-JUN and the hGH-FOS solutions were also dialyzed against dialysis buffer. Samples from all three dialyzed protein solutions were analyzed by SDS-PAGE under non-reducing conditions. Coupling of hGH-FOS to HBcAg-JUN was detected in an anti-hGH immunoblot (FIG. 7). hGH-FOS bound to HBcAg-JUN should migrate with an apparent molecular mass of approximately 53 kDa, while unbound hGH-FOS migrates with an apparent molecular mass of 31 kDa. The dialysate was analyzed by SDS-PAGE in the absence of reducing agent (lane 3) and in the presence of reducing agent (lane 2) and detected by Coomassie staining. As a control, hGH-FOS that had not been mixed with capsid particles was also loaded on the gel in the presence of reducing agent (lane 1).

A shift of hGH-FOS to a molecular mass of approximately 53 kDa was observed in the presence of HBcAg-JUN capsid protein, suggesting that efficient binding of hGH-FOS to HBcAg-JUN had taken place.

Example 23

Insertion of a Peptide Containing a Lysine Residue into the c/e1 Epitope of HBcAg(1–149)

The c/e1 epitope (residues 72 to 88) of HBcAg is located in the tip region on the surface of the hepatitis B virus capsid (HBcAg). A part of this region (Proline 79 and Alanine 80) was genetically replaced by the peptide Gly-Gly-Lys-Gly-Gly (HBcAg-Lys construct). The introduced Lysine residue contains a reactive amino group in its side chain that can be used for intermolecular chemical crosslinking of HBcAg particles with any antigen containing a free Cysteine group.

The HBcAg-Lys DNA sequence was generated by PCRs: The two fragments encoding HBcAg fragments (amino acid residues 1 to 78 and 81 to 149) were amplified separately by PCR. The primers used for these PCRs also introduced a DNA sequence encoding the Gly-Gly-Lys-Gly-Gly peptide. The HBcAg (1 to 78) fragment was amplified from pEco63 using primers EcoRIHBcAg(s) and Lys-HBcAg(as). The HBcAg (81 to 149) fragment was amplified from pEco63 using primers Lys-HBcAg(s) and HBcAg(1–149)Hind(as). Primers Lys-HBcAg(as) and Lys-HBcAg(s) introduced complementary DNA sequences at the ends of the two PCR products allowing fusion of the two PCR products in a subsequent assembly PCR. The assembled fragments were amplified by PCR using primers EcoRIHBcAg(s) and HbcAg(1–149)Hind(as).

For the PCRs, 100 pmol of each oligo and 50 ng of the template DNAs were used in the 50 µl reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (1 minute), 50° C. (1 minute), 72° C. (2 minutes).

Primer Sequences:

```
EcoRIHBcAg(s):
(5'-CCGGAATTCATGGACATTGACCCTTATAAAG-3');           (SEQ ID NO:79)

Lys-HBcAg(as):
(5'-CCTAGAGCCACCTTTGCCACCATCTTCTAAATTAGTACCCACCCAGGTAGC-    (SEQ ID NO:80)
3');

Lys-HBcAg(s):
(5'-GAAGATGGTGGCAAAGGTGGCTCTAGGGACCTAGTAGTCAGTTATGTC-3');   (SEQ ID NO:81)

HBcAg(1-149)Hind(as):
(5'-CGCGTCCCAAGCTTCTAAACAACAGTAGTCTCCGGAAG-3').             (SEQ ID NO:82)
```

For fusion of the two PCR fragments by PCR 100 pmol of primers EcoRIHBcAg(s) and HBcAg(1–149)Hind(as) were used with 100 ng of the two purified PCR fragments in a 50 µl reaction mixture containing 2 units of Pwo polymerase, 0.1 mM dNTPs and 2 mM MgSO$_4$. PCR cycling conditions were: 94° C. for 2 minutes; 30 cycles of 94° C. (1 minute), 50° C. (1 minute), 72° C. (2 minutes). The assembled PCR product was analyzed by agarose gel electrophoresis, purified and digested for 19 hours in an appropriate buffer with EcoRI and HindIII restriction enzymes. The digested DNA fragment was ligated into EcoRI/HindIII-digested pKK vector to generate pKK-HBcAg-Lys expression vector. Insertion of the PCR product into the vector was analyzed by EcoRI/HindIII restriction analysis and DNA sequencing of the insert.

Example 24

Expression and Partial Purification of HBcAg-Lys

*E. coli* strain XL-1 blue was transformed with pKK-HBcAg-Lys. 1 ml of an overnight culture of bacteria was used to innoculate 100 ml of LB medium containing 100 µg/ml ampicillin. This culture was grown for 4 hours at 37° C. until an OD at 600 nm of approximately 0.8 was reached. Induction of the synthesis of HBcAg-Lys was performed by addition of IPTG to a final concentration of 1 mM. After induction, bacteria were further shaken at 37° C. for 16 hours. Bacteria were harvested by centrifugation at 5000×g for 15 minutes. The pellet was frozen at −20° C. The pellet was thawed and resuspended in bacteria lysis buffer (10 mM Na$_2$HPO$_4$, pH 7.0, 30 mM NaCl, 0.25% Tween-20, 10 mM EDTA, 10 mM DTT) supplemented with 200 µg/ml lysosyme and 10 µl of Benzonase (Merck). Cells were incubated for 30 minutes at room temperature and disrupted using a French pressure cell. Triton X-100 was added to the lysate to a final concentration of 0.2%, and the lysate was incubated for 30 minutes on ice and shaken occasionally. *E. coli* cells harboring pKK-HBcAg-Lys expression plasmid or a control plasmid were used for induction of HBcAg-Lys expression with IPTG. Prior to the addition of IPTG, a sample was removed from the bacteria culture carrying the pKK-HBcAg-Lys plasmid and from a culture carrying the control plasmid. Sixteen hours after addition of IPTG, samples were again removed from the culture containing pKK-HBcAg-Lys and from the control culture. Protein expression was monitored by SDS-PAGE followed by Coomassie staining.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., USA), indicating that a significant amount of HBcAg-Lys protein was soluble. Briefly, lysates from *E. coli* cells expressing HBcAg-Lys and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. The HBcAg-Lys protein was detected by Coomassie staining.

The HBcAg-Lys protein was enriched at the interface between 15 and 65% sucrose indicating that it had formed a capsid particle. Most of the bacterial proteins remained in the sucrose-free upper layer of the gradient, therefore step-gradient centrifugation of the HBcAg-Lys particles led both to enrichment and to a partial purification of the particles.

Example 25

Chemical Coupling of FLAG Peptide to HBcAg-Lys Using the Heterobifunctional Crosslinker SPDP Synthetic FLAG peptide with a Cysteine residue at its amino terminus (amino acid sequence CGGDYKDDDDK) was coupled chemically to purified HBcAg-Lys particles in order to elicit an immune response against the FLAG peptide. 600 µl of a 95% pure solution of HBcAg-Lys particles (2 mg/ml) were incubated for 30 minutes at room temperature with the heterobifunctional crosslinker N-Succinimidyl 3-(2-pyridyldithio) propionate (SPDP) (0.5 mM). After completion of the reaction, the mixture was dialysed overnight against 1 liter of 50 mM Phosphate buffer (pH 7.2) with 150 mM NaCl to remove free SPDP. Then 500 µl of derivatized HBcAg-Lys capsid (2 mg/ml) were mixed with 0.1 mM FLAG peptide (containing an amino-terminal cysteine) in the presence of 10 mM EDTA to prevent metal-catalyzed sufhydryl oxidation. The reaction was monitored through the increase of the optical density of the solution at 343 nm due to the release of pyridine-2-thione from SPDP upon reaction with the free cysteine of the peptide. The reaction of derivatised Lys residues with the peptide was complete after approximately 30 minutes.

The FLAG decorated particles were injected into mice.

Example 26

Construction of pMPSV-gp140cys

The gp140 gene was amplified by PCR from pCytTSgp140FOS using oligos gp140CysEcoRI and SalIgp140. For the PCRs, 100 pmol of each oligo and 50 ng of the template DNAs were used in the 50 μl reaction mixtures with 0.2 units of Pwo polymerase, 0.1 mM dNTPs and 2 mM MgSO4. For both reactions, temperature cycling was carried out as follows: 94° C. for 2 minutes; 30 cycles of 94° C. (0.5 minutes), 55° C. (0.5 minutes), 72° C. (2 minutes).

The PCR product was purified using QiaEXII kit, digested with SalI/EcoRI and ligated into vector pMPSVHE cleaved with the same enzymes.

Oligo Sequences:

```
Gp140CysEcoRI:
5'-GCCGAATTCCTAGCAGCTAGCACCGAATTTATCTAA-3';    (SEQ ID NO:83)

SalIgp140
5'-GGTTAAGTCGACATGAGAGTGAAGGAGAAATAT-3'.    (SEQ ID NO:84)
```

Example 27

Expression of pMPSVgp140Cys pMPSVgp140Cys (20 μg) was linearized by restriction digestion. The reaction was stopped by phenol/chloroform extraction, followed by an isopropanol precipitation of the linearized DNA. The restriction digestion was evaluated by agarose gel eletrophoresis. For the transfection, 5.4 μg of linearized pMPSVgp140-Cys was mixed with 0.6 μg of linearized pSV2Neo in 30 μl H$_2$O and 30 μl of 1 M CaCl$_2$ solution was added. After addition of 60 μl phosphate buffer (50 mM HEPES, 280 mM NaCl, 1.5 mM Na$_2$ HPO$_4$, pH 7.05), the solution was vortexed for 5 seconds, followed by an incubation at room temperature for 25 seconds. The solution was immediately added to 2 ml HP-1 medium containing 2% FCS (2% FCS medium). The medium of an 80% confluent BHK21 cell culture (6-well plate) was then replaced by the DNA containing medium. After an incubation for 5 hours at 37° C. in a CO$_2$ incubator, the DNA containing medium was removed and replaced by 2 ml of 15% glycerol in 2% FCS medium. The glycerol containing medium was removed after a 30 second incubation phase, and the cells were washed by rinsing with 5 ml of HP-1 medium containing 10% FCS. Finally 2 ml of fresh HP-1 medium containing 10% FCS was added.

Stably transfected cells were selected and grown in selection medium (HP-1 medium supplemented with G418) at 37° C. in a CO$_2$ incubator. When the mixed population was grown to confluency, the culture was split to two dishes, followed by a 12 h growth period at 37° C. One dish of the cells was shifted to 30° C. to induce the expression of soluble GP140-FOS. The other dish was kept at 37° C.

The expression of soluble GP140-Cys was determined by Western blot analysis. Culture media (0.5 ml) was methanol/chloroform precipitated, and the pellet was resuspended in SDS-PAGE sample buffer. Samples were heated for 5 minutes at 95° C. before being applied to a 15% acrylamide gel. After SDS-PAGE, proteins were transferred to Protan nitrocellulose membranes (Schleicher & Schuell, Germany) as described by Bass and Yang, in Creighton, T. E., ed., *Protein Function: A Practical Approach,* 2nd Edn., IRL Press, Oxford (1997), pp. 29–55. The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with an anti-GP140 or GP-160 antibody for 1 hour. The blot was washed 3 times for 10 minutes with TBS-T (TBS with 0.05% Tween20), and incubated for 1 hour with an alkaline-phosphatase-anti-mouse/rabbit/monkey/human IgG conjugate. After washing 2 times for 10 minutes with TBS-T and 2 times for 10 minutes with TBS, the development reaction was carried out using alkaline phosphatase detection reagents (10 ml AP buffer (100 mM Tris/HCl, 100 mM NaCl, pH 9.5) with 50 μl NBT solution (7.7% Nitro Blue Tetrazolium (Sigma) in 70% dimethylformamide) and 37 μl of X-Phosphate solution (5% of 5-bromo-4-chloro-3-indolyl phosphate in dimethylformamide).

Example 28

Purification of gp140Cys

An anti-gp120 antibody was covalently coupled to a NHS/EDC activated dextran and packed into a chromatography column. The supernatant, containing GP140Cys is loaded onto the column and after sufficient washing, GP 140Cys was eluted using 0.1 M HCl. The eluate was directly neutralized during collection using 1 M Tris pH 7.2 in the collection tubes.

Disulfide bond formation might occur during purification, therefore the collected sample is treated with 10 mM DTT in 10 mM Tris pH 7.5 for 2 hours at 25° C.

DTT is remove by subsequent dialysis against 10 mM Mes; 80 mM NaCl pH 6.0. Finally GP140Cys is mixed with alphavirus particles containing the JUN residue in E2 as described in Example 16.

Example 29

Construction of PLA2-Cys

The PLA2 gene was amplified by PCR from pAV3PLAfos using oligos EcoRIPLA and PLA-Cys-hind. For the PCRs, 100 pmol of each oligo and 50 ng of the template DNAs were used in the 50 μl reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (0.5 minutes), 55° C. (0.5 minutes), 72° C. (2 minutes).

The PCR product was purified using QiaEXII kit, digested with EcoRI/HinDIII and ligated into vector pAV3 cleaved with the same enzymes.

Oligos
EcoRIPLA:
5'-TAACCGAATTCAGGAGGTAAAAAGATATGG-3' (SEQ ID NO:85)

PLACys-hind:
5'-GAAGTAAAGCTTTTAACCACCGCAACCACCAGAAG-3'. (SEQ ID NO:86)

Example 30

Expression and Purification of PLA-cys

For cytoplasmic production of Cys tagged proteins, *E. coli* XL-1-Blue strain was transformed with the vectors pAV3::PLA and pPLA-Cys. The culture was incubated in rich medium in the presence of ampicillin at 37° C. with shaking. At an optical density (550 nm) of, 1 mM IPTG was added and incubation was continued for another 5 hours. The cells were harvested by centrifugation, resuspended in an appropriate buffer (e.g. Tris-HCl, pH 7.2, 150 mM NaCl) containing DNase, RNase and lysozyme, and disrupted by passage through a french pressure cell. After centrifugation (Sorvall RC-5C, SS34 rotor, 15000 rpm, 10 min, 4° C.), the pellet was resuspended in 25 ml inclusion body wash buffer (20 mM tris-HCl, 23% sucrose, 0.5% Triton X-100, 1 mM EDTA, pH8) at 4° C. and recentrifuged as described above. This procedure was repeated until the supernatant after centrifugation was essentially clear. Inclusion bodies were resuspended in 20 ml solubilization buffer (5.5 M guanidinium hydrochloride, 25 mM tris-HCl, pH 7.5) at room temperature and insoluble material was removed by centrifugation and subsequent passage of the supernatant through a sterile filter (0.45 µm). The protein solution was kept at 4° C. for at least 10 hours in the presence of 10 mM EDTA and 100 mM DTT and then dialyzed three times against 10 volumes of 5.5 M guanidinium hydrochloride, 25 mM tris-HCl, 10 mM EDTA, pH 6. The solution was dialyzed twice against 5l 2 M urea, 4 mM EDTA, 0.1 M NH$_4$Cl, 20 mM sodium borate (pH 8.3) in the presence of an appropriate redox shuffle (oxidized glutathione/reduced glutathione; cystine/cysteine). The refolded protein was then applied to an ion exchange chromatography. The protein was stored in an appropriate buffer with a pH above 7 in the presence of 2–10 mM DTT to keep the cysteine residues in a reduced form. Prior to coupling of the protein with the alphavirus particles, DTT was removed by passage of the protein solution through a Sephadex G-25 gel filtration column.

What is claimed is:

1. A composition comprising:
   (a) a non-naturally occurring molecular scaffold comprising:
      (i) a core particle that comprises a virus-like particle or a recombinant form thereof
      (ii) an organizer comprising at least one first attachment site, wherein said organizer is connected to said core particle by at least one covalent bond; and
   (b) an antigen or antigenic determinant with at least one second attachment site, said second attachment site being selected from the group consisting of:
      (i) an attachment site not naturally occurring with said antigen or antigenic determinant; and
      (ii) an attachment site naturally occurring with said antigen or antigenic determinant,
   wherein said second attachment site is capable of association through at least one non-peptide bond to said first attachment site; and
   wherein said antigen or antigenic determinant and said scaffold interact through said association to form an ordered and repetitive antigen array;
   wherein said antigen is an allergenic protein.

2. The composition of claim 1, wherein:
   (a) said core particle is a virus-like particle or a recombinant form thereof; and
   (b) said organizer is a polypeptide or residue thereof; and
   (c) said second attachment site is a polypeptide or residue thereof.

3. The composition of claim 2, wherein said first and/or said second attachment sites comprise:
   (a) an antigen;
   (b) an antibody or antibody fragment;
   (c) biotin;
   (d) avidin;
   (e) streptavidin;
   (f) a receptor;
   (g) a receptor ligand;
   (h) a ligand;
   (i) a ligand-binding protein;
   (j) an interacting leucine zipper polypeptides;
   (k) an amino group;
   (l) a chemical group reactive with an amino group;
   (m) a carboxyl group;
   (n) a chemical group reactive with a carboxyl group;
   (o) a sulfhydryl group;
   (p) a chemical group reactive with a sulfhydryl group; or
   (q) a combination thereof.

4. The composition of claim 3, wherein said second attachment site does not naturally occur with said antigen or antigenic determinant.

5. The composition of claim 2, wherein said core particle is a recombinant alphavirus.

6. The composition of claim 5, wherein said recombinant alphavirus is Sindbis virus and said first attachment site and said second attachment site each comprise an interacting leucine zipper polypeptide.

7. The composition of claim 6, wherein said first attachment site and said second attachment site are the JUN and/or FOS leucine zipper polypeptides.

8. The composition of claim 2, wherein said first attachment site is an amino group and said second attachment site is a sulfhydryl group.

9. The composition of claim 2, wherein said virus-like particle is a hepatitis B virus capsid protein.

10. The composition of claim 9, wherein said first attachment site and said second attachment site each comprise an interacting leucine zipper polypeptide.

11. The composition of claim 10, wherein said first attachment site is the JUN polypeptide and said second attachment site is the FOS polypeptide.

12. The composition of claim 9, wherein said first attachment site is a lysine residue and said second attachment site is a cysteine residue.

13. The composition of claim 2, wherein said virus-like particle is a Measles virus capsid protein.

14. The composition of claim 13, wherein said first attachment site and said second attachment site each comprise an interacting leucine zipper polypeptide.

15. The composition of claim 14, wherein said first attachment site and said second attachment site are the JUN and/or FOS leucine zipper polypeptides.

16. The composition of claim 2, wherein said core particle comprises proteins selected from the group consisting of:
   (a) recombinant proteins of Rotavirus;
   (b) recombinant proteins of Norwalk virus;
   (c) recombinant proteins of Alphavirus;

(d) recombinant proteins of Foot and Mouth Disease virus;
(e) recombinant proteins of Retrovirus;
(f) recombinant proteins of Hepatitis B virus;
(g) recombinant proteins of Tobacco mosaic virus;
(h) recombinant proteins of Flock House Virus; and
(i) recombinant proteins of human Papilomavirus.

17. The composition of claim 16, wherein the first attachment site and the second attachment site each comprise an interacting leucine zipper polypeptide.

18. The composition of claim 16, wherein said first attachment site is an amino group and said second attachment site is sulfhydryl group.

19. The composition of claim 1, wherein said antigen is:
(a) a recombinant bee sting allergen;
(b) a recombinant nut allergen; or
(c) a recombinant food allergen.

20. The composition of claim 19, wherein the first attachment site and the second attachment site each comprise an interacting leucine zipper polypeptide.

21. A process for producing a non-naturally occurring, ordered and repetitive antigen array comprising:
(a) providing a non-naturally occurring molecular scaffold comprising:
  (i) a core particle that comprises a virus-like particle or a recombinant form thereof
  (ii) an organizer comprising at least one first attachment site,
wherein said organizer is connected to said core particle by at least one covalent bond; and
(b) providing an antigen or antigenic determinant with at least one second attachment site, said second attachment site being selected from the group consisting of:
  (i) an attachment site not naturally occurring with said antigen or antigenic determinant; and
  (ii) an attachment site naturally occurring with said antigen or antigenic determinant,
wherein said second attachment site is capable of association through at least one non-peptide bond to said first attachment site; and
(c) combining said non-naturally occurring molecular scaffold and said antigen or antigenic determinant;
wherein said antigen or antigenic determinant and said scaffold interact through said association to form an ordered and repetitive antigen array; and
wherein said antigen is an allergenic protein.

22. The process of claim 21, wherein
(a) said core particle is a virus-like particle or a recombinant form thereof
(b) said organizer is a polypeptide or residue thereof; and
(c) said second attachment site, is a polypeptide or residue thereof.

23. The process of claim 22, wherein said first and/or said second attachment sites comprise:
(a) an antigen;
(b) an antibody or antibody fragment;
(c) biotin;
(d) avidin;
(e) streptavidin;
(f) a receptor;
(g) a receptor ligand;
(h) a ligand;
(i) a ligand-binding protein;
(j) an interacting leucine zipper polypeptides;
(k) an amino group;
(l) a chemical group reactive with an amino group;
(m) a carboxyl group;
(n) a chemical group reactive with a carboxyl group;
(o) a sulfhydryl group;
(p) a chemical group reactive with a sulfhydryl group; or
(q) a combination thereof.

24. The process of claim 23, wherein said second attachment site does not naturally occur with said antigen or antigenic determinant.

25. A method of treatment of allergies comprising administering to a subject the composition of claim 1.

26. A pharmaceutical composition comprising:
(a) the composition of claim 1; and
(b) an acceptable pharmaceutical carrier.

27. A method of immunization for the treatment of allergies comprising administering to a subject a composition comprising:
(a) a non-naturally occurring molecular scaffold comprising:
  (i) a core particle selected from the group consisting of:
    (1) a core particle of non-natural origin; and
    (2) a core particle of natural origin; and
  (ii) an organizer comprising at least one first attachment site;
  wherein at least one said organizer is connected to said core particle by at least one covalent bond; and
(b) an antigen or antigenic determinant with at least one second attachment site, said second attachment site being selected from the group consisting of:
  (i) an attachment site not naturally occurring with said antigen or antigenic determinant; and
  (ii) an attachment site naturally occurring with said antigen or antigenic determinant;
  wherein said second attachment site is capable of association through at least one non-peptide bond to said first attachment site;
  wherein said antigen or antigenic determinant and said scaffold interact through said association to form an ordered and repetitive antigen array;
  wherein said antigen is an allergenic protein; and
  wherein said method is suitable for the treatment of allergies.

28. The method of claim 27, wherein said immunization produces an immune response.

29. The method of claim 27, wherein said immunization produces a humoral immune response.

30. The method of claim 27, wherein said immunization produces a cellular immune response.

31. The method of claim 27, wherein said immunization produces a humoral immune response and a cellular immune response.

32. The method of claim 27, wherein said immunization produces an immune response sufficient to prevent, treat or mitigate allergies.

33. An immunogenic composition for the treatment of allergies comprising:
(a) a non-naturally occurring molecular scaffold comprising:
  (i) a core particle selected from the group consisting of:
    (1) a core particle of non-natural origin; and
    (2) a core particle of natural origin; and
  (ii) an organizer comprising at least one first attachment site,
  wherein at least one said organizer is connected to said core particle by at least one covalent bond; and
(b) an antigen or antigenic determinant with at least one second attachment site, said second attachment site being selected from the group consisting of:

(i) an attachment site not naturally occurring with said antigen or antigenic determinant; and
(ii) an attachment site naturally occurring with said antigen or antigenic determinant,
wherein said second attachment site is capable of association through at least one non-peptide bond to said first attachment site;
wherein said antigen or antigenic determinant and said scaffold interact through said association to form an ordered and repetitive antigen array;
wherein said antigen is an allergenic protein;
wherein said immunogenic composition is suitable for the treatment of allergies.

34. The immunogenic composition of claim 33 further comprising an adjuvant.

35. The immunogenic composition of claim 33, wherein
(a) said core particle is selected from the group consisting of:
(i) a virus
(ii) a virus-like particle;
(iii) a bacteriophage;
(iv) a viral capsid particle; and
(v) a recombinant form of (i), (ii), (iii) or (iv); and
(b) said organizer is a polypeptide or residue thereof; and
(c) said second attachment site is a polypeptide or residue thereof.

36. The immunogenic composition of claim 35, wherein said first and/or said second attachment sites comprise:
(a) an antigen;
(b) an antibody or antibody fragment;
(c) biotin;
(d) avidin;
(e) streptavidin;
(f) a receptor;
(g) a receptor ligand;
(h) a ligand;
(i) a ligand-binding protein;
(j) an interacting leucine zipper polypeptides;
(k) an amino group;
(l) a chemical group reactive with an amino group;
(m) a carboxyl group;
(n) a chemical group reactive with a carboxyl group;
(o) a sulfhydryl group and a chemical;
(p) a chemical group reactive with a sulfhydryl group; or
(q) a combination thereof.

37. The immunogenic composition of claim 33, wherein said core particle comprises a virus-like particle.

38. The immunogenic composition of claim 37, wherein said core particle comprises a Hepatitis B virus-like particle.

39. The immunogenic composition of claim 37, wherein said core particle comprises a measles virus-like particle.

40. The immunogenic composition of claim 36, wherein said core particle comprises a virus.

41. The immunogenic composition of claim 40, wherein said core particle comprises the Sindbis virus.

42. The composition of claim 1, wherein said an antigen or antigenic determinant has a single second attachment site at its carboxyl or amino terminus.

43. The composition of claim 1, wherein said second attachment site is capable of association through at least one covalent non-peptide bond to said first attachment site.

* * * * *